US009861293B2

(12) United States Patent
Lupton et al.

(10) Patent No.: US 9,861,293 B2
(45) Date of Patent: *Jan. 9, 2018

(54) SENSORS, INCLUDING DISPOSABLE SENSORS, FOR MEASURING TISSUE

(71) Applicant: Skulpt Inc., San Francisco, CA (US)

(72) Inventors: Elmer C. Lupton, Charlestown, MA (US); Haydn Taylor, Windham, NH (US); Jose Bohorquez, San Francisco, CA (US); Ken Li, Wellesley, MA (US); Michael Rinehart, San Jose, CA (US)

(73) Assignee: Myolex Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/826,134

(22) Filed: Aug. 13, 2015

(65) Prior Publication Data

US 2016/0038053 A1 Feb. 11, 2016

Related U.S. Application Data

(60) Division of application No. 13/842,698, filed on Mar. 15, 2013, now Pat. No. 9,113,808, which is a
(Continued)

(51) Int. Cl.
*A61B 5/00* (2006.01)
*A61B 5/053* (2006.01)
*A61B 17/00* (2006.01)

(52) U.S. Cl.
CPC ............ *A61B 5/053* (2013.01); *A61B 5/4519* (2013.01); *A61B 5/486* (2013.01); *A61B 5/684* (2013.01);
(Continued)

(58) Field of Classification Search
CPC ..... A61B 5/053; A61B 5/0531; A61B 5/0537; A61B 5/4875
See application file for complete search history.

(56) References Cited

U.S. PATENT DOCUMENTS 4,783,510 A 11/1988 Saotome
5,221,722 A 6/1993 Sehm
(Continued)

FOREIGN PATENT DOCUMENTS

GB 2449904 12/2008
WO 2004048983 6/2004
(Continued)

OTHER PUBLICATIONS

Ogunnika, Olumuyiwa T et al : "A handheld Electrical Impedance Myography probe for the assessment of neuromuscular disease" Engineering in Medicine and Biology Society, 2008 EMBS 2008, 30th Annual International Conference of the IEEE, IEEE, Piscataway, NJ Aug. 20, 2008. pp. 3566-3569.
(Continued)

Primary Examiner — Max Hindenburg
(74) Attorney, Agent, or Firm — Elmer C. Lupton

(57) ABSTRACT

Embodiments of devices and methods for evaluating tissue are disclosed. In one embodiment, a method for measuring a characteristic of a tissue may include passing a current through the tissue, measuring a signal corresponding to the voltage resulting from passing the current through the tissue, analyzing current passed through the tissue and resulting voltage to determine the electrical characteristics of the tissue; and analyzing the electrical characteristics of the tissue to determine a status of the tissue. Disposable sensors are disclosed.

18 Claims, 70 Drawing Sheets

Related U.S. Application Data continuation-in-part of application No. 13/823,659, filed as application No. PCT/US2012/035658 on Apr. 27, 2012, now Pat. No. 8,892,198.

(60) Provisional application No. 61/480,127, filed on Apr. 28, 2011, provisional application No. 61/570,298, filed on Dec. 13, 2011, provisional application No. 61/775,620, filed on Mar. 10, 2013.

(52) U.S. Cl.
CPC .......... *A61B 5/6843* (2013.01); *A61B 5/7221* (2013.01); *A61B 5/7225* (2013.01); *A61B 5/7278* (2013.01); *A61B 5/742* (2013.01); *A61B 5/7405* (2013.01); *A61B 5/7475* (2013.01); *A61B 5/6833* (2013.01); *A61B 2017/0023* (2013.01); *A61B 2560/0412* (2013.01); *A61B 2560/0443* (2013.01); *A61B 2560/0468* (2013.01); *A61B 2562/04* (2013.01); *A61B 2562/046* (2013.01); *A61B 2562/14* (2013.01); *A61B 2562/164* (2013.01); *A61B 2562/166* (2013.01)

(56) References Cited

U.S. PATENT DOCUMENTS

| | | | |
|---|---|---|---|
| 5,280,429 | A | 1/1994 | Withers |
| 5,807,272 | A | 9/1998 | Kun et al. |
| 5,856,410 | A | 1/1999 | Carrico et al. |
| 5,919,142 | A | 7/1999 | Boone et al. |
| 6,122,544 | A | 9/2000 | Orgon |
| 6,371,921 | B1 | 4/2002 | Caro et al. |
| 6,587,715 | B2 | 7/2003 | Singer |
| 6,631,292 | B1 | 10/2003 | Liedtke |
| 6,723,049 | B2 | 4/2004 | Skladney et al. |
| 6,768,921 | B2 | 7/2004 | Orgon et al. |
| 6,845,264 | B1 | 1/2005 | Skladney et al. |
| 6,859,049 | B2 | 2/2005 | Khatchatrian et al. |
| 7,003,346 | B2 | 2/2006 | Singer |
| 7,136,697 | B2 | 11/2006 | Singer |
| 7,148,701 | B2 | 12/2006 | Park et al. |
| 7,184,820 | B2 | 2/2007 | Jersey-Willuhn et al. |
| 7,212,852 | B2 | 5/2007 | Smith et al. |
| 7,457,660 | B2 | 11/2008 | Smith et al. |
| 7,783,345 | B2 | 8/2010 | Skrabal et al. |
| 7,865,236 | B2 | 1/2011 | Cory et al. |
| 7,869,866 | B2 | 1/2011 | Loriga et al. |
| 8,004,291 | B2 | 8/2011 | Waki |
| 8,099,250 | B2 | 1/2012 | Essex |
| 8,103,337 | B2 | 1/2012 | Gravovac |
| 8,145,318 | B2 | 3/2012 | Van Herk |
| 8,150,507 | B2 | 4/2012 | Hamaguchi et al. |
| 8,238,996 | B2 | 8/2012 | Burnes et al. |
| 8,412,317 | B2 | 4/2013 | Mazar |
| 8,452,390 | B2 | 5/2013 | Jensen |
| 8,498,687 | B2 | 7/2013 | Karo et al. |
| 8,644,919 | B2 | 2/2014 | Zdeblick |
| 8,644,925 | B2 | 2/2014 | Volpe et al. |
| 9,113,808 | B2 | 8/2015 | Bohorquez et al. |
| 2004/0002662 | A1 | 1/2004 | Hjelt et al. |
| 2004/0073131 | A1 | 4/2004 | Organ et al. |
| 2004/0167422 | A1 | 8/2004 | Organ et al. |
| 2004/0210157 | A1 | 10/2004 | Organ et al. |
| 2004/0210158 | A1 | 10/2004 | Organ et al. |
| 2004/0243018 | A1 | 12/2004 | Organ et al. |
| 2004/0243019 | A1 | 12/2004 | Graovac et al. |
| 2005/0004490 | A1 | 1/2005 | Organ et al. |
| 2005/0197591 | A1 | 9/2005 | Pavlovic et al. |
| 2006/0151815 | A1 | 7/2006 | Gravovac et al. |
| 2007/0293918 | A1 | 12/2007 | Thompson et al. |
| 2008/0064979 | A1 | 3/2008 | Pavlovic et al. |
| 2008/0076998 | A1 | 3/2008 | Organ et al. |
| 2008/0249432 | A1 | 10/2008 | Semlyen et al. |
| 2010/0105993 | A1 | 4/2010 | Naghavi et al. |
| 2010/0222841 | A1 | 9/2010 | Mintchev |
| 2010/0256516 | A1 | 10/2010 | Kasahara |
| 2010/0292603 | A1 | 11/2010 | Shiffman |
| 2012/0245436 | A1 | 9/2012 | Rutkove et al. |
| 2012/0323136 | A1 | 12/2012 | Shiffman |
| 2013/0197389 | A1 | 8/2013 | Levin et al. |
| 2014/0249613 | A1 | 9/2014 | Kaib |
| 2014/0257429 | A1 | 9/2014 | Mohn et al. |

FOREIGN PATENT DOCUMENTS

| | | |
|---|---|---|
| WO | WO2004048983 | 6/2004 |
| WO | WO2007/035887 | 3/2007 |
| WO | WO2007/035887 A2 | 3/2007 |
| WO | WO2011/022068 | 2/2011 |
| WO | WO2011/022068 A1 | 2/2011 |
| WO | WO2012149471 A1 | 11/2012 |
| WO | WO2015031278 A1 | 3/2015 |
| WO | 2015056262 A1 | 4/2015 |

OTHER PUBLICATIONS

S.B. Rutkove et al., "Characterizing spinal muscular atrophy with electrical impedance myography", Muscle & Nerve, Dec. 2010, pp. 915-921.

M.A. Ahad et al., "The effect of subacute denervation on the electrical anisotropy of skeletal muscle: Implications for clinical diagnostic testing", Clinical Neurophysiology, 121 (2010) 882-886.

L.P. Garmirian et al. "Discriminating Neurogenic from Myopathic Disease via Measurement of Muscle Anisotrophy" Muscles & Nerve 39: Jan. 16-24, 2009.

M.A. Ahab et al., "Electrical characteristics of rat skeletal muscle in immaturity, adulthood and after sciatic nerve injury, and their relation to muscle fiber size.", Physiological Measurement, 30 (2009), 1415-1427, published Nov. 4, 2009.

S.B.Rutkove, "Electrical impedance myography as a biomarker for ALS", the Lancet, vol. 8, Mar. 2009, p. 226.

M.A. Ahad et al. "Electrical impedance myography at 50 kHz in the rat: Technique, reproducibility and the effects of sciatic injury and recovery", Clinical Neurophysiology 120 (2009) 1534-1538.

S.B. Rutkove, "Electrical Impedance Myography: Background, Current State, and Future Directions", Muscle & Nerve, 1-11, 2009.

A.B. Chin et al. "Optimizing Measurement of the Electrical Anistropy of Muscle", Muscle & Nerve, 1-6, 2008.

S.B. Rutkove et al. Reference Values for 50 kHz Eelctrical Impedance Myography, Muscle & Nerve, Sep. 2008, 1128-1132.

S.B. Rutkove et al. "Electrical Impedance Myography to Assess outome in amyotrophic laterial sclerosis clinical trials" Clinical Neurophysiology 118 (2007) 2413-2418.

G.J. Esper et al., "Assessing Neuromuscular Disease with Multifrequency Electrical Impendance Myography:" Muscle Nerve 34:595-602 (2006.).

A.W. Tarulli et al., "Electrical impedance in bovine skeletal muscle as a model for the study of neuromuscular disease" Physiol. Meas. 27 (2006) 1269-1279.

S.B. Rurkove et al. "Test-retest reproducibility of 50 kHz linear-electrical impedance myography" Clinical Neurophysiology 117 (2006 1244-1248.

Tarulli et al. "Electrical impedance myography in the bedside assessment of inflammatory myopathy" Neurology, 2005:65 451-452.

S.B. Rutkove "Electrical Impedance Myography in the Detection of Radiculopathy" Muscle Nerve 32: 335-341, 2005.

S.B. Rutkove et al. "Electrode position and size in electrical impedance myography", Clinical Neurophysiology 116 (2005) 290-299.

C.A. Shiffman et al. "Electrical impedance of muscle during isometric contraction", Physiological Measurement 24 (2003) 213-234.

S.B. Rutkove et al. "Localized bioimpedance analysis in the evaluation of neuromuscular disease." Muscle Nerve 25:390-397, 2002.

(56) References Cited

OTHER PUBLICATIONS

M.A. Ahad et al., "finite element Analysis of Electrical Impedance Myography in the Rat Hind Limb", Conf. Proc IEEE End Med Biol Soc. 2009; 1:630, 1-10.

C Lungu et al. "Quantifying Muscle Asymmetries in Cervical Dystonia with Electrical Impedance: A Preliminary Assessment", Clin. Nuerophysiol. May 2011; 122(5) 1027-1031.

A.W. Tarulli et al. "Electrical Impedance Myography in the Assessment of Disuse Atrophy", Arch Phys. Med. Rehabil. Oct. 2009; 90(10) 1806-1810.

A.W. Tarulli et al. "Localized muscle impedance abnormalities in amyotrophic lateral sclerosis", J. Clin. Neuromuscul. Dis. Mar. 2009; 10(3): 90-96.

O.T. Ogunnika et al., "A Handheld Electrical Impedance Myography Probe for the Assessment of Neuromuscular Disease" Conf. Proc. IEEE Eng Med Biol. Soc 2008: 3566-3569.

R. Nie et al., "Electrical impedance myography: Transitioning from human to animal studies" Clinical Neurophysiology 117 (2006) 1844-1849.

R. Aaron et al. "Effects of age on muscle as measured by electrical impedance myography", Physiol. Meas. 27 (2006) 953-959.

A.W. Tarulli et al. "Multifrequency Electrical Impedance Myography in Amyltrophic Lateral Sclerosis" $13^{th}$ International Conference on Electrical Bioimpedance and the $8^{th}$ Conference on electrical Impedance Tomography, IFMBE Proceedings vol. 17 2007, pp. 647-650.

L.P. Garmirian et. al. "Discriminating Neurogenic from Myopathic Disease via Measurement of Muscle Anisotropy", Muscle & Nerve 39: Jan. 16-24, 2009.

M.A.Ahab et. al., "Electrical characteristics of rat skeletal muscle in immaturity, adulthood and after sciatic nerve injury, and their relation to muscle fiber size.", Physiological Measurement, 30 (2009), 1415-1427, published Nov. 4, 2009.

M.A.Ahad et. al. "Electrical impedance myography at 50 kHz in the rat: Technique, reproducibility and the effects of sciatic injury and recovery", Clinical Neurophysiology 120 (2009) 1534-1538.

S.B.Rutkove, "Electrical Impedance Myography: Background, Current State, and Future Directions", Muscle & Nerve, 1-11, 2009.

A.B. Chin et. al. "Optimizing Measurement of the Electrical Anisotropy of Muscle", Muscle & Nerve, 1-6, 2008.

S.B. Rutkove et. al. "Reference Values for 50 kHz Electrical Impedance Myography", Muscle & Nerve, Sep. 2008, 1128-1132.

S.B. Rutkove et. al. "Electrical Impedance Myography to assess outome in amyotrophic lateral sclerosis clinical trials" Clinical Neurophysiology 118 (2007) 2413-2418.

A.W.Tartulli, et. al., "Impact of skin-subcutaneous fat layer thickness of electrical impedance myography measurements: An initial assessment" Clinical Neurophysiology 118 (2007) 2393-2397.

G. J. Esper et. al., "Assessing Neuromuscular Disease with Multifrequency Electrical Impedance Myography:" Muscle Nerve 34:595-602 (2006.).

A.W. Tarulli et. al., "Electrical impedance in bovine skeletal muscle as a model for the study of neuromuscular disease" Physiol. Meas. 27 (2006) 1269-1279.

S.B. Rurkove et. al. "Test-retest reproducibility of 50 kHz linear-electrical impedance myography" Clinical Neurophysiology 117 (2006) 1244-1248.

A. Tarulli et. al., "Electrical impedance myography in the bedside assessment of inflammatory myopathy" Neurology, 2005:65 451-452.

S.B.Rutkove et. al., "Electrode position and size in electrical impedance myography", Clinical Neurophysiology 116 (2005) 290-299.

C.A. Shiffman et. al. "Electrical impedance of muscle during isometric contraction", Physiological Measurement 24 (2003) 213-234.

S.B.Rutkove et. al. "Localized bioimpedance analysis in the evaluation of neuromuscular disease." Muscle Nerve 25:390-397, 2002.

M.A. Ahad et. al., "Finite Element Analysis of Electrical Impedance Myography in the Rat Hind Limb", Conf. Proc IEEE End Med Biol Soc. 2009; 1:630, 1-10.

C Lungu et. al. "Quantifying Muscle Asymmetries in Cervical Dystonia with Electrical Impedance: A Preliminary Assessment", Clin. Neurophysiol. May 2011; 122(5) 1027-1031.

A.W.Tarulli et. al. "Electrical Impedance Myography in the Assessment of Disuse Atrophy", Arch Phys. Med. Rehabil. Oct. 2009; 90(10) 1806-1810.

A.W. Tarulli et. al., "Localized muscle impedance abnormalities in amyotrophic lateral sclerosis", J. Clin. Neuromuscul. Dis. Mar. 2009; 10(3): 90-96.

O.T. Ogunnika et. al., "A handheld Electrical Impedance Myography Probe for the Assessment of Neuromuscular Disease" Conf. Proc. IEEE Eng Med Biol Soc 2008: 3566-3569.

R. Nie et. al., "Electrical impedance myography: Transitioning from human to animal studies" Clinical Neurophysiology 117 (2006) 1844-1849.

R. Aaron et. al. "Effects of age on muscle as measured by electrical impedance myography", Physiol. Meas. 27 (2006) 953-959.

A.W.Tarulli et. al. "Multifrequency Electrical Impedance Myography in Amyltrophic Lateral Sclerosis" 13th International Conference on Electrical Bioimpedance and the 8th Conference on Electrical Impedance Tomography, IFMBE Proceedings vol. 17 2007, pp. 647-650.

Occamschainsaw, "Skulpt Aim", Dropkicker, Jan. 7, 2014, pp. 1-7, http://drop-kicker.com/2014/01/skulpt-aim/ (downloaded Jun. 22, 2017).

Figure 9: Transimpedance amplifer for LBTI measurements.

$G_1 = 5.4$, $G_2 = 3.0$, $G_3 = 3.0$, $G_4 = 4.99$, $G_{IAMP} = 242.514$ $G_1 = 430\Omega$, $G_2 = 3.0$, $G_3 = 3.0$, $G_4 = 4.99$, $G_{TIA} = 19.3113 \text{ k}\Omega$ ADC range = $2.0 V_{p-p}$ → input range = $103.57 \ \mu A_{p-p} = 36.6 \ \mu A_{rms}$ $$Z_{cal} = G_{TIA} / G_{IAMP} = 430\Omega / 5.4 = 79.6296$$

| # | CURRENT | VOLTAGE | PURPOSE |
|---|---------|---------|---------|
| 1 | S/I 1 | V1 | INLINE, 0 DEGREES |
| 3 | S/I 2 | V2 | INLINE, 45 DEGREES |
| 7 | S/I 3 | V3 | INLINE, 90 DEGREES |
| 9 | S/I 4 | V4 | INLINE, 135 DEGREES |
| 2 | S/I 1 | V3 | ORTH., 0 DEGREES (FOR ALIGNMENT) |
| 4 | S/I 2 | V5 | WIDE INLINE, 45 DEGREES |
| 5 | S/I 2 | V4 | ORTH., 45 DEGREES |
| 6 | S/I 2 | V6 | WIDE ORTH., 45 DEGREES |
| 8 | S/I 3 | V1 | ORTH., 90 DEGREES (FOR ALIGNMENT) |
| 10 | S/I 4 | V6 | WIDE INLINE, 135 DEGREES |
| 11 | S/I 4 | V2 | ORTH., 135 DEGREES |
| 12 | S/I 4 | V5 | WIDE ORTH., 135 DEGREES |

Figure 15: OTI measurements on meat, TX-151, and meat with a layer of TX-151 placed between it and the electrodes.

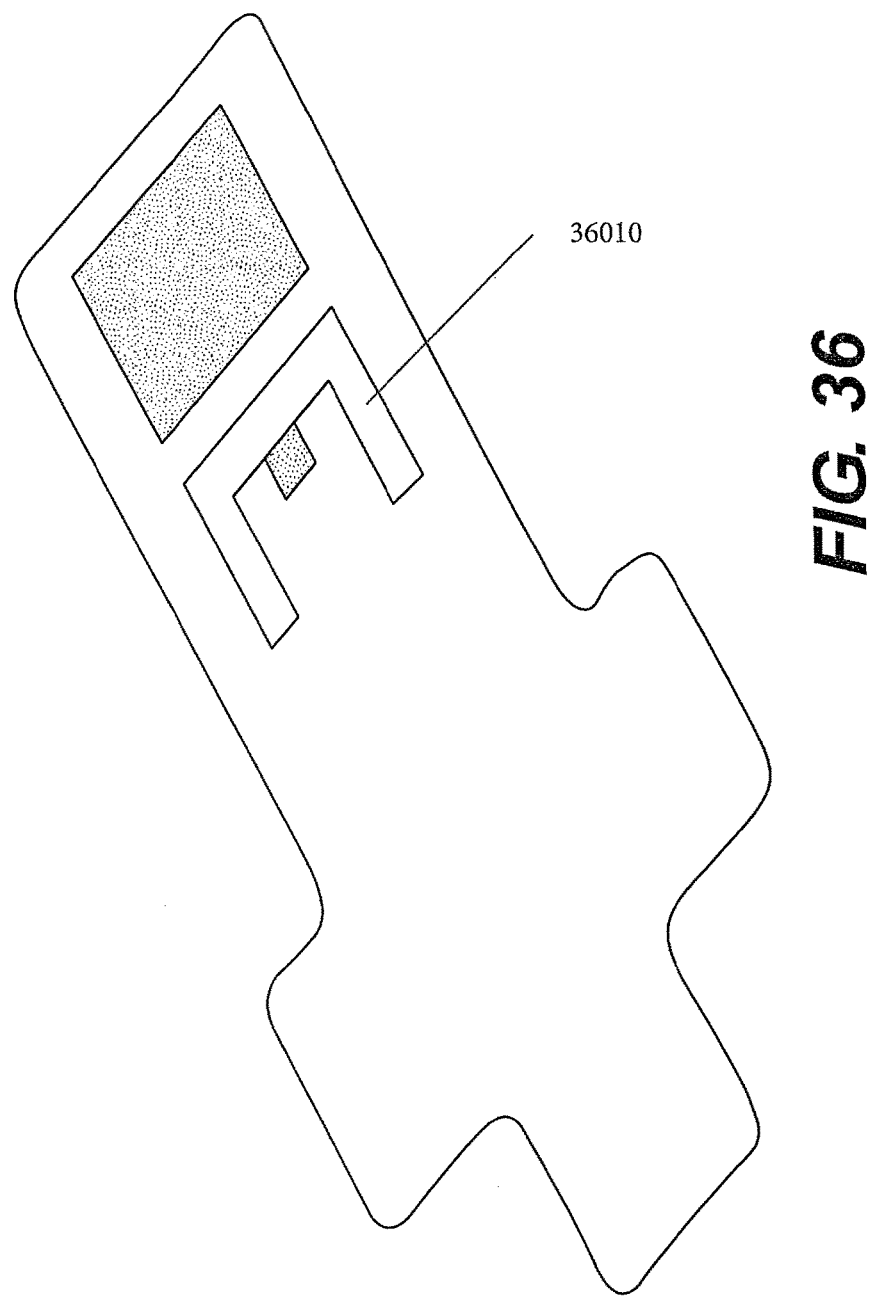

PLEASE ENTER SITE NAME AND PATIENT INFORMATION

| | COMPLETED |
|---|---|
| CHANGE DEVICE BATTERIES | ☑ |
| DISINFECT ELECTRODES | ☑ |
| INFORMED CONSENT | ☑ |
| MEDICAL RECORDS REVIEW | ☑ |
| MEDICAL HISTORY REVIEW | ☑ |
| CASE REPORT FORM | ☑ |
| MEDICAL EXAMINATION | ☑ |

SITE NAME: CONVERGENCE MEDICAL DEVICES
PATIENT #: 0001
GENDER: MALE ▽
DATE OF BIRTH: 04 / 13 / 1981
HEIGHT: 70 INCHES ▽
WEIGHT: 185 LBS ▽
SKIN TEMPERATURE: 37 DEGREES C ▽
HAND DOMINANCE: RIGHT ▽

NOTES:
SUBJECT HAS A SLIGHT LIMP ON LEFT LEG

[START EXAM]

◯ POWER ☐ BATTERY | VERSION 1.0

FIG. 57A

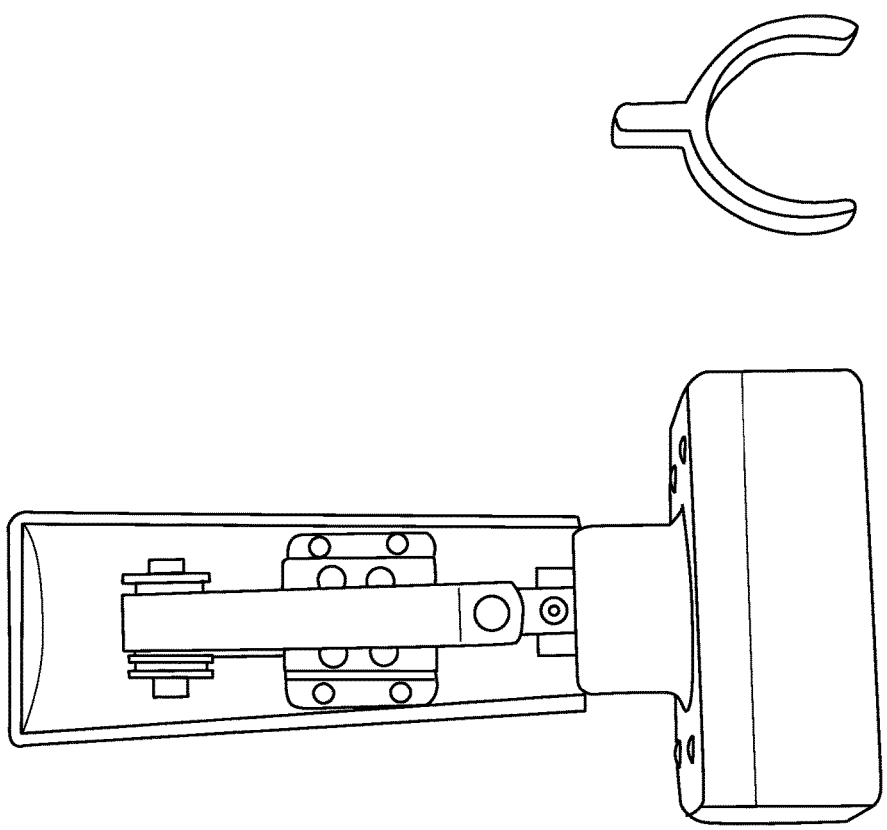

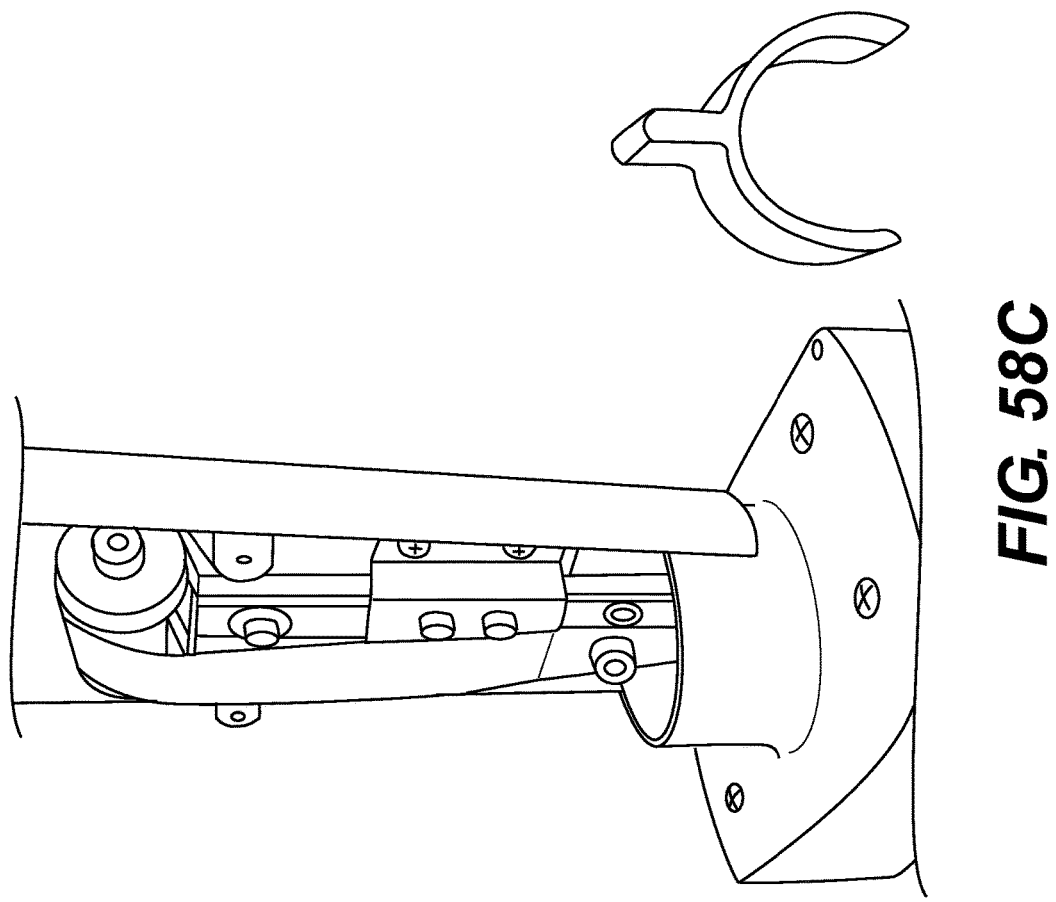

10122

| ITEM NO. | PART NUMBER | QTY. |
|---|---|---|
| 1 | Pull tab (allows pierce of pouch) | 1 |
| 2 | Foam Block Outer (Fluid barrier, closed cell foam) | 1 |
| 3 | Flex Sensor | 1 |
| 4 | Steel Washer (Magnetic latch) | 2 |
| 5 | Disposable Base Molding | 1 |
| 6 | Foam Block Inner (Fluid reservoir, open cell foam) | 1 |
| 7 | Saline pouch | 1 |

| ITEM NO. | PART NUMBER |
|---|---|
| 1 | Disposable Base Plate |
| 2 | R3-Foam-Major-R2 |
| 3 | Sensor-Flex circuit |
| 4 | Steel Washer |

SENSORS, INCLUDING DISPOSABLE SENSORS, FOR MEASURING TISSUE

CROSS-REFERENCE TO RELATED APPLICATIONS

This application is a divisional application of U.S. patent application Ser. No. 13/842,698 filed Mar. 15, 2013, (US Patent Application publication 20130338473), now U.S. Pat. No. 9,113,808, application Ser. No. 13/842,698 is a continuation-in-part application of U.S. patent application Ser. No. 13/832,659, filed Mar. 14, 2013, (US Patent Application publication 20140039341), now U.S. Pat. No. 8,892,198, which is an entry into the U.S. National stage of, and claims priority to, International Application Number PCT/US2012/035658 (Publication WO2012/149471) filed Apr. 27, 2012, which is entitled to the benefits of priority under 35 U.S.C. §§119-120 to U.S. Provisional Patent Application Nos. 61/480,127 and 61/570,298 filed on Apr. 28, 2011, and Dec. 13, 2011, respectively. The entireties of all of these applications and patents are incorporated herein by reference.

application Ser. No. 13/842,698 also claims priority to and incorporates in its entirety by reference U.S. Provisional Patent Application No. 61/775,620 titled "EIM Technology," filed Mar. 10, 2013. The entirety of this application is incorporate herein by reference.

GOVERNMENT LICENSE RIGHTS

This invention was made with U.S. government support under grant R43NS070385-01 awarded by National Institutes of Health and grant 1046826 awarded by the National Science Foundation. The government has certain rights in the invention.

FIELD OF THE INVENTION

Embodiments of the present disclosure relate generally to medical devices suitable for evaluating the health and/or status of bodily tissues. In particular, some embodiments of the present disclosure relate to devices and methods for evaluating the health and/or status of, e.g., muscular tissues for the purposes of evaluating the efficacy of one or more treatment regimens.

BACKGROUND OF THE INVENTION

Embodiments of this disclosure will describe devices and methods for conducting measurements to determine status and/or health of tissue. One area of the disclosure will address neuromuscular diseases, which are very common. In 2009, there were over 18 million outpatient physician encounters with patients diagnosed with a range of neuromuscular diseases, from ALS to myoneural disorders like myasthenia gravis. These episodes generated nearly $7B in physician charges and can only be expected to grow as the episode volume is expected to reach over 20 million by 2014 (+8.25%).

Another area our disclosure will address common medical complaints, such as, e.g., lower back and neck pain. These common medical complaints are sometimes the primary causes of disability, lost productivity, and medical costs. For example, 60-80% of adults experience at least one significant episode of back pain in their lifetime. In a single year, about 15% will have debilitating back pain, and a substantial proportion will seek medical attention. Lower back pain has been estimated as the fifth or higher leading cause of all medical visits, and the first or second leading cause for patients seeking evaluation and treatment of a condition. Stated another way, about 4-5% of all medical encounters are related to back pain. In two major health surveys (National Health Interview Survey and National Health and Nutrition Survey), from 2004-2008, 28-40% of the U.S. population experienced neck or back pain in a three-month period, with 14-21% experiencing neck pain. Of the total group, 26-33% experienced associated radicular pain in a limb. Remarkably, lumbosacral and cervical pain together caused 5% of all U.S. health care visits in the in 2006.

Costs associated with care of individuals with low back and neck pain are huge. For example, in 2006, 44.4 million patients sought medical attention for low back pain, which was the chief complaint in 45.1 million encounters; an additional 13.2 million medical encounters were for neck pain. Annual cost of back pain in the US is $20-50 billion. Direct medical costs in 2002-2004 for spine problems were $193.9 billion, with $30.3 billion attributed specifically to spine pain. Indirect costs of lost wages are estimated at $14 billion annually, and in 2008, 385 million work days were lost due to back pain. The subgroup of patients with pain radiating to the limb, as occurs with disc herniation or spinal stenosis, had the highest numbers of bedridden and lost work days. Non-physician health care visits, e.g., physical therapy and other services, numbered 173.5 million from 2002-2004. Utilization is increasing, with ambulatory physician visits up 2.5% and non-physician visits up 10.2% from 1996-1998 to 2002-2004, with total increase in health care costs for spine of 24.5% (mean) and 48.9% (aggregate) in the same time period.

Another area our disclosure will address is the muscular health of older adults, which is the fastest growing segment of the population. Health care cost are exceptionally high for older adults with declining function, accounting for a disproportionate fraction of national health care expenditures. Muscle weakness is an independent risk factor for disability and mortality among older adults. Age associated loss of muscle mass, known as sarcopenia, is an important factor identified as relevant to mortality and disability.

In a recent and important editorial on sarcopenia and muscle function, Ferrucci et. al. (L. Ferrucci, R. de Cabo, N. D. Knuth, S. Studenski "*Of Greek heroes, wiggling worms, mighty mice and old body builders*", J. Gerontol A Biol Sci Med Sci 2012; 67:13-6, [Ferrucci 2012] which is incorporated herein in its entirety by reference) advocated for a clinical approach in evaluating age associated muscle impairments, stating that after an initial mobility assessment to stratify patient risk for adverse outcomes (e.g., disability and mortality), muscle strength should be measured and a decision tree assessment used to evaluate muscle quality and function.

Both the general research community and the U.S. Food and Drug Administration (FDA) recognize the importance of improved biomarkers for neuromuscular disease research to assist with early diagnosis and track disease progression over time and response to therapy. Even more fundamentally, the concept of biomarker has expanded beyond its earlier definition that was restricted to molecular indices and now includes, but it not limited to, imaging and other methodologies. In fact, the FDA defines a biomarker as any objective test of disease status that cannot be influenced by the state of mind of the patient or examiner. The FDA recently developed biomarker definitions including diagnostic biomarkers for disease identification, response predictive biomarkers for assessing subgroups of individuals more likely to respond to a specific therapy, and prognostic biomarkers, for evaluating likelihood of disease onset or progression without any form of intervention. The FDA definitions provided herein are for discussions and references purposes only, and are not intended to limit any term contained herein. Two categories of biomarkers include response identification biomarkers (also called pharmacodynamic biomarkers) and biomarkers as surrogate endpoints in clinical trials. As a result, the FDA is revamping its approach to drug approval based on such surrogate endpoints. Previously, approval demanded evidence of change in a clinical outcome measure, such as, e.g., improved physical function or activity. In the future, however, it may be possible for a biomarker, which is established as a surrogate endpoint in a clinical trial, to obtain "qualification" status through the FDA as a surrogate endpoint, helping speed study and approval of effective therapies.

One technique for evaluating muscles is intramuscular electromyography (EMG.) EMG includes, but is not limited to, a technique for evaluating and recording the electrical activity produced by muscles, including, e.g., skeletal muscles. EMG may be performed using an instrument called an electromyograph, to produce a record called an electromyogram. An electromyograph may detect, among other things, the electrical potential generated by muscle cells when the cells are electrically or neurologically activated. The detected signals may be analyzed to detect, among other things, medical abnormalities, activation level, recruitment order or to analyze the biomechanics of human or animal movement. EMG is exceedingly intrusive in that it uses the insertion of needles through the skin and into the muscles and the use of these needles to measure electrical potential.

Electrical impedance myography (EIM) is a novel technological approach to effectively address these limitations. Unlike standard electrophysiological approaches, EIM is less directly dependent upon inherent electrical potential of muscle or nerve tissue. EIM is based on electrical bioimpedance. It measures the effect of tissue structure and properties on flow of extremely small, non-intrusive amounts of electrical current. Unlike standard bioimpedance approaches, however, measurements can be performed over small areas of muscle and incorporate sophisticated analytic tools. In EIM, electrical current, such as, e.g., high-frequency alternating current, may be applied to localized areas of muscle via electrodes (e.g., surface electrodes) and the consequent surface voltage patterns may be analyzed. Although data can be obtained with off-the-shelf bioimpedance devices, these devices are far from ideal in terms of providing useful data reliably, as discussed in more detail below.

FIG. 62A illustrates the concepts underlying EIM. Electrical current (sinusoid "a") is applied via two or more outer surface electrodes generating a voltage difference measured by the two or more inner electrodes (sinusoid "b"). The voltage may be proportional to tissue resistance (R). Myocyte membrane lipid bilayers are capacitive in nature (e.g., they briefly store and then release some or all of the stored charge) and so exhibit reactance (X), making the voltage sine wave out of phase with applied current wave. Reactance and resistance values may be combined to obtain the summary phase angle ($\theta$) via the relationship $\theta=\arctan(X/R)$. FIG. 62B shows changes seen in diseased or less than ideal muscle tissue. Here, presence of connective tissue, fat and reduced muscle mass, among other things, may increase measured resistance; muscle fiber atrophy and loss also results in reduced reactance (e.g., timing of voltage sinusoid is now only slightly shifted relative to current). Thus, phase angle, as well as the resistance and reactance may be used to measure, e.g., disease progression. As disease advances, reactance and phase angle may decrease whereas resistance may increase.

Two additional aspects to EIM may include:
a) strong frequency dependence of EIM data. Thus, performing EIM measurements across a range of frequencies may help to characterize tissue. FIG. 63 shows multifrequency data "d" from a normal subject and from a patient with advanced ALS (Emory U. stem cell study), which is denoted by "e". Note major alteration in impedance parameters across the frequency spectrum.
b) electrical anisotropy—directional dependence of current flow. Typically, electrical current flows relatively easily along muscle fibers than across them conferring a readily detectable anisotropy. Alteration in electrical anisotropy can also be used as a measure to evaluate muscle tissue to, e.g., determine a disease state, and early data show that anisotropy increases in, among other things, ALS.

Although much previous EIM work was done with off-the-shelf whole-body bioimpedance systems, for example, using these systems for localized impedance measurements may be problematic for a variety of reasons, including, but not limited to, the systems: 1) may not be calibrated for the very different impedances found in localized areas of tissue, such as, e.g., muscle tissue; 2) may be unable to effectively measure and account for muscle anisotropy; 3) rely on multiple, clumsy adhesive electrodes that may be slow to apply and result in spacing variability; and 4) may operate over a limited frequency range that may miss certain clinical information. Thus, there is a need for a handheld, rapidly applied, broadly capable, robust EIM system for bedside use.

There are some reports of the use of electrical impedance for biometric purposes. Examples of such uses may be found in: U.S. Pat. No. 6,122,544 to L. W. Orgon "Electrical Impedance Method and Apparatus for Detecting and Diagnosing Diseases" (Orgon 544); U.S. Pat. No. 6,768,921 to Leslie W. Organ, K. C. Smith, Reza Safaee-Rad, M. Graovac, G. P. Darmos, and I. Gavrilov, "Electrical impedance method and apparatus for detecting and diagnosing diseases" (Organ 921); U.S. Pat. No. 6,845,264 and PCT Application Publication No. WO 00/19894, Skladnev; Victor, Thompson; Richard L., Bath; Andrew R., "Apparatus for recognizing tissue types", (Skladnev 264); U.S. Pat. No. 6,723,049 and Australian Application No. PR5718, Skladnev; Victor Nickolaevich, Blunsden; Christopher Kingsley, Stella; Rita "Apparatus for tissue type recognition using multiple measurement techniques" (Skladev 049); U.S. Pat. No. 7,212,852 to K. C. Smith, J. S. Ironstone, F. Zhang, "Bioimpedance measurement using controller-switched current injection and multiplexer selected electrode connection", (Smith 852); U.S. Pat. No. 7,457,660 to K. C. Smith and J. I. Ironstone "Eliminating interface artifact errors in bioimpedance measurements" (Smith 660); U.S. Pat. No. 7,136,697 to Michael G. Singer "Methods for determining illness, progression to death, and/or timing of death of biological entity" (Singer 697); U.S. Pat. No. 7,003,346 to Michael G. Singer, "Method for illness and disease determination and management" (Singer 346); U.S. Pat. No. 8,103,337 to M. Gravovac, J I Marteus, Z. Pavlovic and J. Ironstone "Weighted Gradient Method and System for Diagnosing Disease" (Gravovac 337); U.S. Pat. No. 6,631,292 to R. J. Liedtke, (Liedtke 292) "Bio-electrical Impedance Analyzer"; U.S. Pat. No. 8,004,291 to Naosumi Waki, "Bioelectric impedance measuring circuit", (Waki 291); U.S. Pat. No.

7,869,866 to Giannicola Loriga; Andrea Scozzari, "Device for the monitoring of physiologic variables through measurement of body electrical impedance", (Loriga 866); U.S. Pat. No. 7,148,701 to Sin-Chong Park; In-Duk Hwang; "Apparatus for measuring electrical impedance" (Park); U.S. Patent Application Publication No. 2010/0292603 and PCT Application Publication No. WO/2007/035887 to C. A. Shiffman, R. Aaron and S. Rutkove, "Electrical Impedance Myography" (Shiffman 887); PCT Application No. WO 2011/022068 to Seward Rutkove "A Hand-held Device for Electrical Impedance Myography" (Rutkove 068); U.S. Pat. No. 5,919,142 and PCT Application No. PCT/GB96/01499 to Boone, Kevin Graham; Holder David Simon "Electrical impedance tomography method and apparatus (Boone 142); U.S. Patent Publication No. 2005/0004490 A1 to L. W. Organ, K. C. Smith, R Safaee-Rad, M. Granvac, P. Darmos and I Gavrilov, "Electrical Impedance Method and Apparatus for Detecting and Diagnosing Diseases" (Organ 490); U.S. Patent Application Publication No. 2005/0197591 to Z. Pavlovic, M Graovuc, J. S. Ironstone, "System and Method for Prebalancing Electrical Properties to Diagnose Disease" (Pavlovic 591); U.S. Patent Application Publication No. 2004/0073131 to L. W. Organ, K. C. Smith, R Sufaee-Rad, M. Graovac, G. P. Darmos and I. Gavrilov, "Electrical Impedance Method and Apparatus for Detecting and Diagnosing Diseases" (Organ 131); U.S. Patent Application Publication No. 2004/0167422 to L. W. Organ, R Sufaee-Rad, M. Graovac, K. C. Smith, J. S. Ironstone, "Breast Electrode Array and Method of Analysis for Detecting and Diagnosing Diseases", (Organ 422); U.S. Patent Application Publication No. 2004/0210157 L. W. Organ, K. C. Smith, R. Safaee-Rad, M. Graovac, G. P. Darmos and I. Gavrilov "Electrical Impedance Method and Apparatus for Detecting and Diagnosing Diseases" (Organ 157); U.S. Patent Application Publication No. 2004/0210158 to L. W. Organ, K. C. Smith, R. Safaee-Rad, M. Graovac, G. P. Darmos and I. Gavrilov "Electrical Impedance Method and Apparatus for Detecting and Diagnosing Diseases" (Organ 158); U.S. Patent Application Publication No. 2004/0243018 to L. W. Organ, K. C. Smith and J. S. Ironstone, "Apparatus and Method for Determining Adequacy of Electrode-So-Skin Contact and Electrode Quality for Bioelectrical measurements" (Organ 018); U.S. Patent Application Publication No. 2004/0243019 to M. Graovac and Z. Pavlovic, "Weighted Gradient Method and System for Diagnosing Disease" (Graovac 019); U.S. Patent Application Publication No. 2008/0064979 to Z. Pavlovic, M. Graovac and J. S. Ironstone, "System and Method for Prebalancing Electrical Properties to Diagnose Disease" (Pavlovic 979); U.S. Patent Application Publication No. 2008/0076889 to L. W. Organ, R. Safaee-Rad, M. Graovac, K. C. Smith, J. S. Ironstone, "Breast Electrode Array and Method of Analysis for Detecting and Diagnosing Diseases", (Organ 889); and U.S. Patent Application Publication No. 2008/0249432 and PCT Application No. PCT/CA04/00458 A to Semlyen and M. Graovac "Diagnosis of Disease by Determination of Electrical Network Properties of a Body Part", (Semiyen 432). All of these patents and patent applications are incorporated herein in their entirety by reference.

SUMMARY OF THE DISCLOSURE

Embodiments of the present disclosure relate to devices and methods for evaluating bodily tissue, such as, e.g., muscular tissue. Embodiments of the present disclosure include living and dead tissue as well as animal and plant tissue.

In one embodiment, a method for measuring a characteristic of a tissue includes passing a current through the tissue, measuring a signal corresponding to the voltage resulting from passing the current through the tissue, analyzing current passed through the tissue and resulting voltage to determine the electrical characteristics of the tissue, and analyzing the electrical characteristics of the tissue to determine a status of the tissue.

Various embodiments of the method may include one or more of the following features: the status is a health of the tissue; the tissue may include living human tissue; the tissue may include muscular tissue; the current may include alternating current; the frequency of the alternating current may be between 1 kHz and 10 MHz; analyzing the current passed through the tissue may be performed by a device comprising an amplifier; the amplifier may be a transimpedance amplifier; the signal to noise ratio of the measured signal may be enhanced by a device comprising premeasurement drive equalization; the direction of measuring the signal may not be collinear with the direction along which the current is passed; the direction of measurement of the signal may be between 60 degrees and 120 degrees rotated from the direction along which the current is passed; the direction of measurement of the voltage may be between 85 degrees and 95 degrees rotated from the direction along which the current is passed; the device may include a plurality of lock-in amplifiers operating in parallel; the method may further comprise measuring and calculating LBTI at a plurality of frequencies simultaneously; the method may further comprise verifying a calibration of the device prior to measuring the signal; the calibration of the device may be verified automatically and the step of measuring is not permitted to proceed if the calibration cannot be verified; the step of passing a current through tissue may be performed by an electrical component having a plurality of electrode contacts configured to provide electrical contact with a surface of the tissue; the plurality of electrodes may be contained in an electrode assembly; the electrode assembly may be disposable and is only used for a single series of measurements; the method may further comprise analyzing the electrode assembly for a prior use; the step of measuring a signal may be prohibited if the electrode assembly was previously used; analyzing the electrode assembly for a prior use may be conducted by a mechanical mechanism; analyzing the electrode assembly for a prior use may be conducted by an electrical method, and wherein the analyzing may be conducted by electronics within the electrical component; the step of analyzing the electrode assembly for a prior use may be conducted by remote electronic components; the electrical component may include at least two parts which can be detached, at least one of the parts comprising the electrode assembly; the at least two parts may be secured together by one or more magnets; the at least two parts may be secured to one another by one or both of a friction or interference fit; the step of analyzing the electrical characteristics of the tissue may comprise the use of Cole parameters; and the use of Cole parameters may further comprise calculating a semi-ellipse to which three of the four Cole parameters are related and using that relationship to reparameterize the problem into two sequential optimizations: a quadratic optimization that computes an optimal circle that fits the data, and quasi-convex optimization that uses results of the optimization to find the remaining parameter; the semi-ellipse may comprise a semi-circle.

In another embodiment, a device for measuring a characteristic of a tissue may include a plurality of electrodes; a power supply configured to be operably coupled to the plurality of electrodes to supply a signal through the tissue; analytical electronics configured to be operably coupled to the plurality of electrodes for analyzing a input current and resulting voltage to determine the electrical characteristics of the tissue; and electronics configured to communicate to a user a result of analysis performed by the analytical electronics.

Various embodiments of the device may include one or more of the following features: the signal may include controlled alternating current; a frequency of the alternating current may be between 1 kHz and 10 MHz; the analytical electronics may comprise a transimpedance amplifier; a signal to noise ratio of the measured signal may be enhanced by a device comprising premeasurement drive equalization; at least one of the plurality of electrodes may be configured to measure voltage; a direction of measurement of the voltage may not be collinear with the direction along which the current is passed; a direction of measurement of the voltage may be between 60 degrees and 120 degrees rotated from the direction along which the current is passed; a direction of measurement of the voltage may be between 85 degrees and 95 degrees rotated from the direction along which the current is passed; the device may further comprise a plurality of lock-in amplifiers operating in parallel capable of simultaneous measurement and calculation of LBTI at a plurality of frequencies; the device may be unable to measure voltage unless the device is calibrated; the device may be configured to be calibrated automatically; the plurality of electrodes may be contained in an electrode assembly; the electrode assembly may be disposable and may be only used for a single series of measurements; the device may be further configured to determine whether the electrode assembly was previously used; the device may further comprise a mechanical mechanism for determining if the electrode assembly was previously used; the device may further comprise an electrical mechanism for determining if the electrode assembly was previously used; the electrical mechanism may be disposed in the device; the electrical mechanism may be remote of the device; the device may include at least two parts detachably secured to one another, at least one of the parts comprising the electrode assembly; the at least two parts may be secured together by a magnet; the at least two parts may be secured to one another by one or both of a friction or interference fit; the analytical electronics may be configured to analyze the input current and resulting voltage with the use of Cole parameters; the use of Cole parameters may further comprise calculating a semi-ellipse to which three of the four Cole parameters are related and using that relationship to reparameterize the problem into two sequential optimizations: a quadratic optimization that computes an optimal ellipse that fits the data, and quasi-convex optimization that uses results of the optimization to find the remaining parameter; and the semi-ellipse may comprise a semi-circle.

In other embodiments, there are single subject, disposable sensors to be placed on the test subject to provide the contact to permit EIM measurements to be made. By using a single subject, disposable sensor, cross-contamination and infection are reduced or eliminated. Additional embodiments can incorporate a pouch of saline solution or a gel block in the disposable sensor to release fluid and enhance conductivity and reduce impedance during measurements. Additional embodiments can include an absorbent fluid reservoir to supply saline to the surface of the sensor and improve the connection.

Additional objects and advantages of the disclosure will be set forth in part in the description that follows, and in part will be obvious from the description, or may be learned by practice of the disclosed embodiments. The objects and advantages of the disclosure will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIG. 35 (A) shows one embodiment of a handheld probe and electrode array patch. FIG. 35 (B) shows another embodiment of a handheld probe and electrode array pad. FIG. 35 (C) shows top and bottom views of electrode array pad. FIG. 35 (D) shows a zoomed in image of electrode array with circles marked 35D10 highlighting the current electrodes and circles marked 35D20 highlighting the voltage electrodes that compose the same configuration that was proposed. The other electrodes were added to allow flexibility to select a variety of electrode configurations using multiplexers. FIG. 35 (E) shows a side view of electrode array pad showing rubber like material before it conforms to curved surface. FIG. 35 (F) shows a side view of electrode array pad conforming to curved surface.

FIG. 36 is a diagram of a flexible/adhesive patch electrode interface with electrodes arranged in an example format with an example tab (top) containing wires that connect to the electrodes.

The several views of FIG. 57 show the graphical user interface. FIG. 57A shows the startup page requesting site and patient information and requiring operator to certify that the protocol has been followed.

FIG. 58B shows a front view of handheld probe with front cover detached. The "CFA disabler" snaps onto the base to disable the CFA, allowing analysis on the effect of constant force actuation on quality data. FIG. 58C shows an isometric view of handheld probe showing the constant force spring along with the linear guide and rail used to implement constant force actuation.

The several views of FIG. 59 show the constant force actuator at different states: FIG. 59 D shows half-way displaced.

Figure 1:
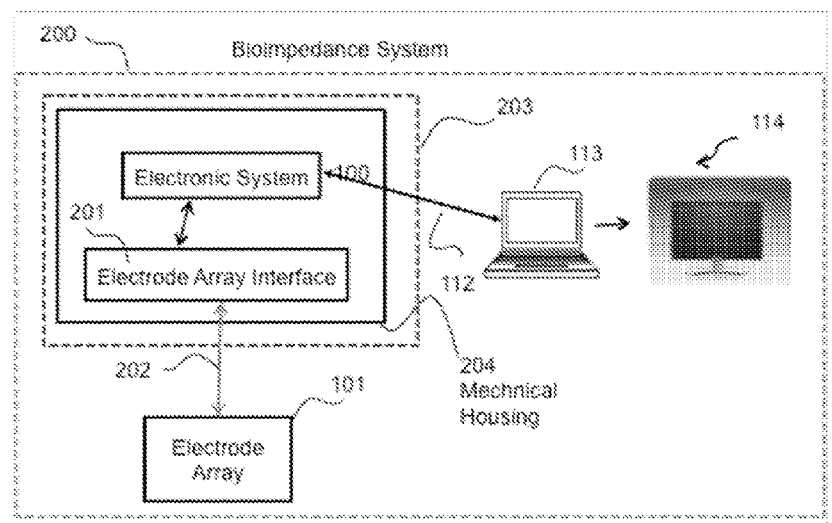
FIG. 1 is a block diagram of the bioimpedance system.

The figures also are in U.S. patent application Ser. No. 13/842,698 filed Mar. 15, 2013, (US Patent Application publication 20130338473), now U.S. Pat. No. 9,113,808 which is incorporated herein in its entirety by reference.

DETAILED DESCRIPTION OF THE DISCLOSURE

Overview of Embodiments

One aspect of the disclosure involves a method for measuring the health of a tissue, such as, e.g., muscular tissue. Another aspect involves measuring the health of living human tissue. Another aspect involves making measurements with the use of alternating current. Another aspect involves alternating current between 1 kHz and 10 MHz. Another aspect involves analysis of input current by a device with a transimpedance amplifier. Another aspect involves measurement where signal to noise ratio is enhanced by premeasurement drive equalization. Another aspect involves measurement where the direction of measurement of the voltage is not collinear with the direction along which the current is passed. Another aspect involves measurement where the direction of measurement of the voltage is between approximately 60 degrees and approximately 120 degrees rotated from the direction along which the current is passed. Another aspect involves measurement where the direction of measurement of the voltage is between approximately 85 degrees and approximately 95 degrees rotated from the direction along which the current is passed. Another aspect involves verification of calibration of the system prior to initiation of measurements. Another aspect involves verification where the calibration is verified automatically and the measurement is not permitted to proceed if the calibration cannot be verified. Another aspect involves measurement where there are electrodes to provide electrical contact with the surface of the tissue. Another aspect involves containing the electrodes in an electrode assembly. Another aspect involves an electrode assembly which is disposable and is only used for a single series of measurements. Another aspect involves the verification of the single use of the disposable electrode assembly and not permitting the measurement to proceed if the verification fails. Another aspect involves the verification of single use being a mechanical method. Another aspect involves verification of single use by an electrical method in which the verification occurs locally in the measurement device. Another aspect involves verification of single use by an electrical method in which the verification involves a remote measurement or comparison. Another aspect involves the device holding the electrodes having at least two parts which can be detached. Another aspect involves the two parts of the device holding the electrodes being held together by a magnetic mechanism. Another aspect involves the two parts of the device holding the electrodes being held together by the use of molded or machined sections frictionally held together, such as, e.g., by snap-fit. Another aspect involves analyzing tissue with the use of Cole parameters. Another aspect involves the use of Cole parameters with calculating a semicircle to which three of the four Cole parameters are related.

Still another aspect of the disclosure involves a device for measuring the health of a tissue. Another aspect involves a device using controlled alternating current. Another aspect involves a device with alternating current between approximately 1 kHz and approximately 10 MHz. Another aspect involves a device with analysis of input current by a device with a transimpedance amplifier. Another aspect involves a device with measurement where signal to noise ratio is enhanced by premeasurement drive equalization. Another aspect involves a device with measurement where the direction of measurement of the voltage is not collinear with the direction along which the current is passed. Another aspect involves a device with measurement where the direction of measurement of the voltage is between approximately 60 degrees and approximately 120 degrees rotated from the direction along which the current is passed. Another aspect involves a device for making measurements where the direction of measurement of the voltage is between approximately 85 degrees and approximately 95 degrees rotated from the direction along which the current is passed. Another aspect involves a device with verification of calibration of the system prior to initiation of measurements. Another aspect involves a device with verification where the calibration is verified automatically and the measurement is not permitted to proceed if the calibration cannot be verified. Another aspect involves a device with electrodes contained in an electrode assembly. Another aspect involves a device where an electrode assembly which is disposable and is only used for a single series of measurements. Another aspect involves a device where verification of the single use of the disposable electrode assembly and not permitting the measurement to proceed if the verification fails. Another aspect involves a device where the single use of the electrode assembly is verified by an electrical or mechanical means and the measurement is not permitted to proceed if the verification fails. Another aspect involves a device with the verification of single use being a mechanical method. Another aspect involves a device with verification of single use by an electrical method in which the verification occurs locally in the measurement device. Another aspect involves a device with verification of single use by an electrical method in which the verification involves a remote measurement or comparison. Another aspect involves the device holding the electrodes having at least two parts which can be detached. Another aspect involves the two parts of the device holding the electrodes being held together by a magnetic mechanism. Another aspect involves the two parts of the device holding the electrodes being held together by the use of molded or machined sections which snap together. Another aspect involves a device where analyzing tissue uses of Cole parameters. Another aspect involves a device where analyzing tissue uses Cole parameters with calculating a semi-circle to which three of the four Cole parameters are related.

Description of the System

FIG. 1 illustrates a system for, among other things multi-angle, multi-frequency, localized biological transfer impedance (LBTI) measurements. For purposes of discussion, transfer impedance may include, but is not limited to, the ratio of the voltage applied at one or more terminals in a network to the current measured by one or more other terminals in the network. In addition, transfer impedance may include, but is not limited to, the ratio of a voltage measured across one or more terminals in a network to the current applied to one or more different terminals.

In contrast with whole-body transfer impedance measurements (also referred to as "whole body bioimpedance"), which yield information about the entire body of a subject, LBTI measurements capture information relating to one or more particular regions of the subject, for example. Localized biological transfer impedances may include, but is not limited to, transfer impedance measurements made over one or more localized areas of biological tissue including parts of a living body. For example, an LBTI measurement performed on the surface of a patient's bicep would yield information regarding, among other things, skin, subcutaneous fat, and muscle tissue directly below and in the immediate vicinity of the electrodes used in the measurement.

LBTI measurements have been used to extract physiological information in human subjects that correlate to fluid status, body-mass index, cardiac output, and neuromuscular disease. The disclosure described here includes, but is not limited to, a system and method for taking LBTI measurements of a type which are previously unknown. The system in depicted in FIG. 1 illustrates one embodiment of the disclosure comprising a handheld probe (203), a computing device (113), a display (114), and an electrode array (101) as the primary components.

Figure 2:
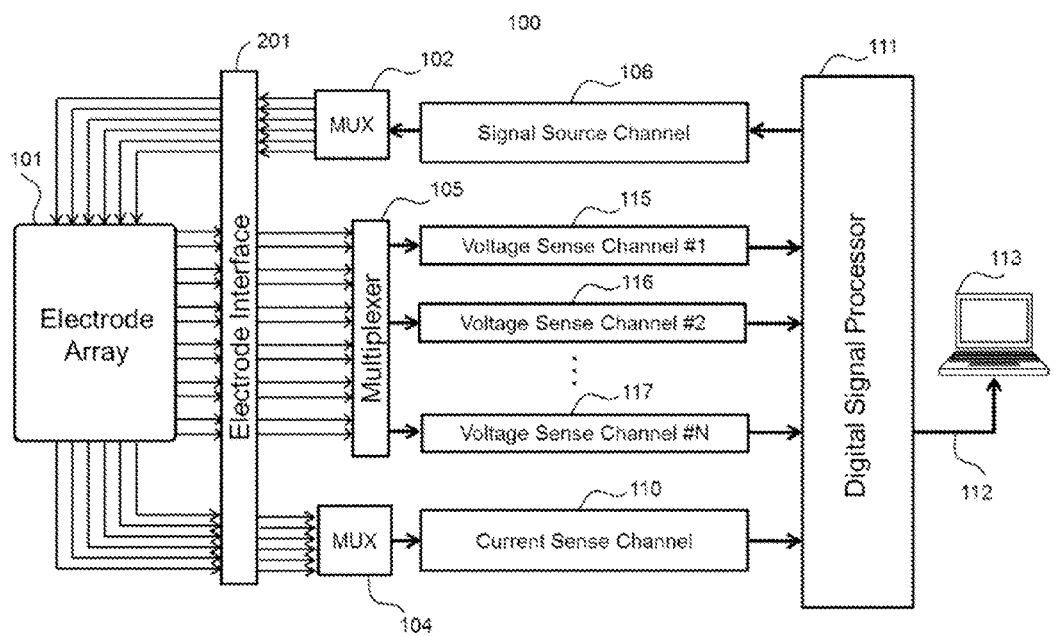
FIG. 2 is a detailed block diagram of the system.

The handheld probe (203) may include a mechanical housing (204), an electronic system (100), and an electrode array interface mechanism (201). FIG. 2 illustrates parts of the disclosure in more detail. The electrode array (101) may be used to make contact with physiological material; typically the surface of a patient's skin. The electrode array (101) may include a plurality of electrodes, some of which may be used to apply an electrical signal such as current or voltage, and others that are used to sense an electrical signal such as voltage or current. One or more of the plurality of electrodes in the electrode array (101) may be selectively activatable.

An electrode interface can be used to connect the electrodes to a suitable electronic system and may include features such as constant force actuation to control the amount of force applied by the electrodes to the material. Multiplexers, cross-point switches, relays, or other types of switching mechanisms (102, 104, 105) may be used to switch the connection between different electrodes and different components in the electronic system such as the signal source channel (106), one or more voltage sense channels (115-117), or a current sense channel. Each of these channels (106, 110, 115-117) may connect to a suitable signal processor, including, e.g., a digital signal processor (DSP, 111) that may be implemented in a field-programmable gate array (FPGA), a microprocessor, or similar. In one embodiment, the DSP may interface with a computing device (113) such as a personal computer, notebook, laptop, personal digital assistant (PDA), smart phone, or other similar device capable of executing one or more algorithms. The connection between the DSP and computing device (113) may be implemented using a cable, such as a universal serial bus (USB), or a wireless connection, including, but not limited to, WiFi, Bluetooth, and radio frequency. In another embodiment, the DSP and computing device may be combined into a single device embedded within the handheld probe (203).

Electronics for Signal Generation and Acquisition

In one embodiment of the disclosure, only a single voltage channel may be used to measure the voltage difference between two electrodes in the electrode array. However, there may be cases where measuring the voltage difference between more than one pair of electrodes simultaneously is desirable to expedite a full measurement sweep or synchronize between channels. In such cases, the voltage sense channels may be identical. However, they may also be different if, for example, the amplitude or frequency range of the signals at the input of each channel is expected to differ.

Figure 3:
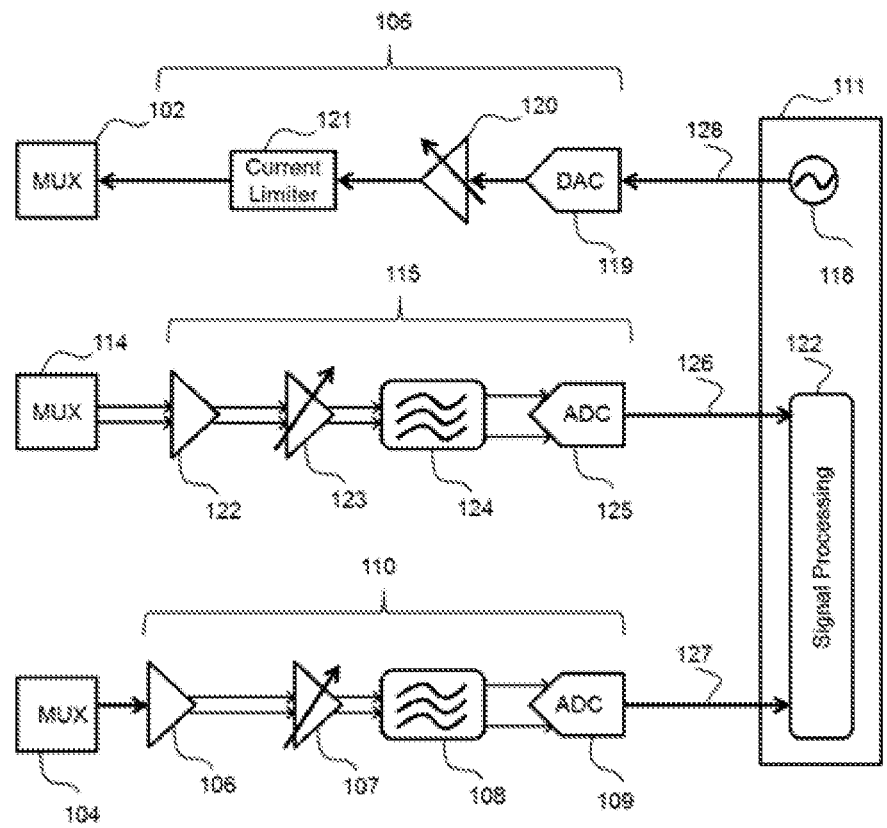
FIG. 3 is a block diagram of the signal generation and acquisition.

Without intending to be limiting, FIG. 3 shows one possible implementation of the device with a signal source channel (106), a voltage sense channel (115), and a current sense channel (110) for an implementation where a single voltage sense channel is used. Again, without intending to be limiting, one configuration of the components of the signal source channel may include a digital-to analog converter (DAC, 119), a variable-gain amplifier (VGA, 120), and a current limiter (121). The DAC may be used to generate an analog electrical signal using data received from the DSP (111). Specifically, the DSP may include a waveform generator (118) such as a direct digital synthesizer (DDS) or an arbitrary waveform generator. The analog electrical signal generated by the DAC may be amplified or otherwise conditioned using VGA (120) so that the amplitude of the signal applied to the patient can be controlled.

The amplitude setting of the VGA can be set digitally by the DSP or through any other suitable mechanism. The VGA can also take part of a feedback loop to control the amount of current applied to the patient or the amplitude of the voltage at the input of the voltage sense channel (115). The output of the VGA can be a current or a voltage, and it may be passed through a current limiter to ensure that the amount of current delivered to the subject is never greater than some threshold. This is important since safety regulations require limits on electrical signals applied to subjects, and also to ensure that other electronic components affected by this waveform do not saturate. The output of the current limiter connects to the multiplexer (102) which directs the current to one or more electrodes in the electrode array.

In one embodiment of the disclosure, the voltage sense channel (115) comprises, but is not limited to, a fully differential instrumentation amplifier (IAMP, 122) (however, any suitable amplifier may be used within the principles of the present disclosure), a fully differential VGA (123), a fully differential filter (124), and an analog-to-digital converter (ADC, 125). Any other suitable electronic components may be included. The use of fully differential signaling has the benefit of reducing the influence of common-mode noise. The main purpose of the instrumentation amplifier (IAMP) is to amplify differential voltage signals between desired pairs of electrodes in the electrode array. The design and selection of the IAMP will represent number of considerations, including, e.g., a balance and tradeoffs among at least the following characteristics: (i) low input-referred noise to minimize signal corruption; (ii) high input impedance to minimize the effects of contact impedance on the accuracy of the measurements and to minimize current measurement errors; and/or (iii) high bandwidth that is significantly higher than the desired signal's highest frequency content.

It is well known that operating an amplifier near its bandwidth can result in phase distortion. Using higher bandwidth IAMPs may result in less phase distortion. In some embodiments of the disclosure, a plurality of subsequent amplifier stages can be used. In FIG. 3, a second stage VGA (123) is used to amplify the voltage signal further with optional amplitude control. Distributing the total gain of the voltage amplification channel into multiple stages has the benefit of improving the frequency response of the system. It is well known that most amplifiers present a tradeoff between gain and bandwidth. By splitting the system gain into multiple stages, less gain can be used for each amplifier resulting in an overall higher bandwidth for the system. This results in higher amplitude and phase accuracy for the system at higher frequencies.

In one embodiment of the disclosure, a filter (124) is used in the voltage sense channel. The filter may be active or passive, and it may provide additional gain. One purpose for the filter is to provide anti-aliasing before digitizing the signal using an ADC. More generally, the filter removes unwanted noise and interference from the measured electrical signal. The ADC (125) in the voltage sense channel is used to digitize the measured waveform. Its output is connected to the DSP for digital signal processing. In one embodiment of the disclosure, the sampling rate of the ADC may be higher than the Nyquist rate (e.g., twice the frequency of the highest frequency component of the desired signal). In another embodiment, the ADC may be operated at a lower sampling rate such that the signal is "sub-sampled". This will result in aliasing which is commonly undesirable. However, under some circumstances, the desired information may still be retrieved despite aliasing. For example, if the signal is sinusoidal, aliasing will result in frequency translation of the signal to a predictable baseband frequency where information can still be recovered from it. Sub-sampling may have the benefit of reducing power consumption in the system or allowing the use of a more accurate ADC since there is often a tradeoff between the maximum sampling rate of an ADC and the accuracy (measured in signal-to-noise ratio (SNR), dynamic range, or effective number of bits).

In another embodiment of the disclosure, the current sense channel (110) comprises a transimpedance amplifier (TIA) with differential output (106), a fully differential VGA (107), a fully differential filter (108), and an ADC (109). The description of the VGA, filter, and ADC in the current sense channel 110 is the same as for the voltage sense channel 115. In one embodiment of the disclosure, components 107-109 in the current sense channel may be substantially matched to components 123-125 in the voltage sense channel. Since transfer impedances may be generally calculated by taking the ratio of a measured voltage to a measured current, it is important to minimize or match any amplitude or phase error introduced by the instrumentation. By using matched components in the two channels, phase and gain errors can be matched in the current and voltage measurements and then cancelled when ratios are taken.

Transimpedance Amplifier

A transimpedance amplifier may include, but is not limited to, an amplifier that converts an input current to an output voltage. In some embodiments, the input may include a characteristically low input impedance, which may serve to effectively shunt parasitic input capacitances. Tetrapolar impedance measurements may be made with, e.g., four electrodes: two for driving a current and two for sensing the voltage. Traditionally, the drive electrodes are driven by a true current source, which in theory has infinite impedance, but pragmatically, needs only to have a relatively (such as, e.g., >10 times) higher impedance than any other pertinent impedance in the measurement.

In practice, there are several important considerations in performing this measurement. For example, real voltage amplifiers may require a common-mode potential reference, which partially constrains voltages to within the input range of the amplifiers. Typically, this reference may be connected with a low impedance, to reduce common-mode interference from external sources that may drive the amplifier inputs outside of its range. A further consideration may be that the impedance to this reference is relatively lower (such as, e.g., <100 times) than the input impedance of the amplifier, and that input stage of the amplifier not only be biased properly, but also so that asymmetries in the input impedance will not cause an unacceptable error. The accuracy of a tetrapolar measurement relies on how well the current through the material under test can be determined. In the following illustrations, the contact impedance may be ignored to highlight the effect of a performance-dominating source impedance.

Figure 4:
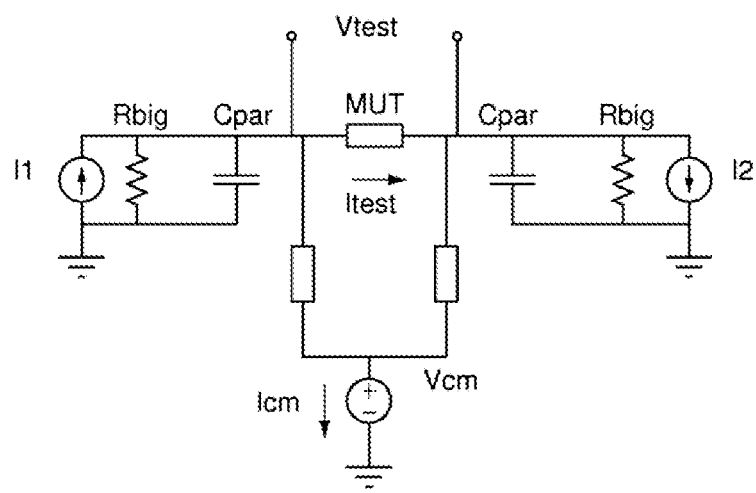
FIG. 4 is a circuit diagram of previously reported example in differential current driving for impedance measurements.
Figure 5:
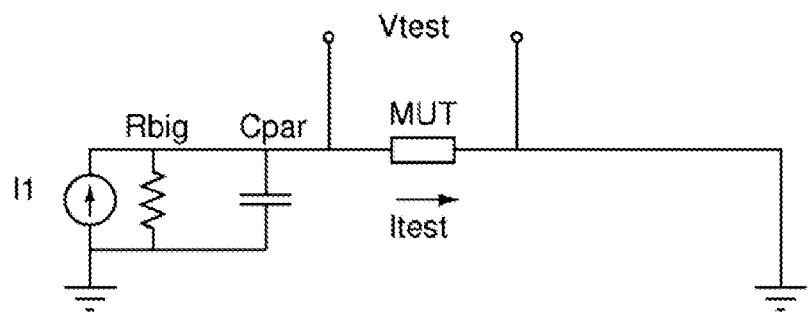
FIG. 5 is a circuit diagram of previously reported example in single-ended current driving for impedance measurements.

FIG. 4 illustrates a previously reported (Grimnes, S. and Martensen, O. G. "Bioimpedance and Bioelectricity Basics", Acad. Press, Burlington, Mass. 2008 (Grimnes 2008) which is incorporated herein in its entirety by reference) example in differential current driving for impedance measurement. Differential current driving could be part of element 100 of FIG. 1 and element 106 of FIG. 2. $I_1$ may be a current source and $I_2$ may be a current sink with equally opposite polarity. In practice, it is difficult to match these currents and resulting current offset ($I_{cm}$) appears through the potential reference ($V_{cm}$) causing errors. $R_{big}$ is the Thevenin equivalent resistance for a practical current source. MUT is the material-under-test through which current ($I_{test}$) is passed. $I_{test}$ is not necessarily $I_1$ nor $I_2$ nor a combination of these because of the current path through the parasitic capacitance ($C_{par}$), along with $I_{cm}$. This constitutes an error that increases linearly with frequency above $\frac{1}{2}*2\pi R_{big}C_{par}$. True impedance of MUT is $z=V_{test}/i_{test}$ FIG. 5 illustrates a previously reported (Grimnes 2008) single-ended current driving for impedance measurement. Because the current sink is ground or suitably low impedance, error between $I_{test}$ and $I_1$ is through a single capacitor $C_{par}$. Bandwidth penalty is half of that in a differential current drive.

Figure 6:
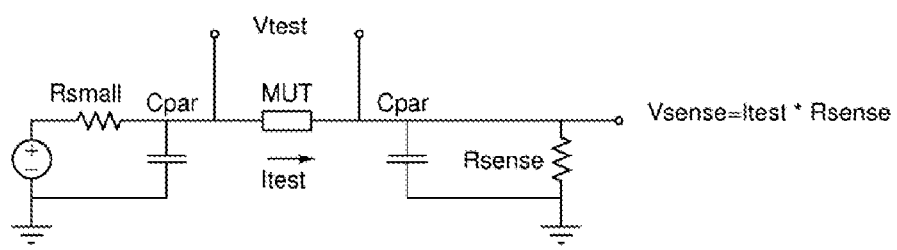
FIG. 6 is a circuit diagram of a previously reported example for impedance measurements.

FIG. 6 illustrates a previously reported design [O. T. Ogannika, M. Scharfstein, R. C. Cooper, H. Ma, J. T. Dawson and S. Rutkove, "A Handheld Electrical Impedance Myography Probe for the Assessment of Neuromuscular Disease", 30th Annual International IEEE EMBS Conference, Vancouver, BC, Canada, Aug. 20-24, 2008. (Ogannika 2008) which is incorporated here in its entirety by reference] in which a voltage signal is used to induce a current through the MUT instead of directly applying a current signal using a current source. A voltage source is defined to have a negligible Thevenin impedance ($R_{small}$), which is much smaller (<100 times) in magnitude than the impedance of MUT. The current through the material is now a derived quantity to be measured. In this case, it is the voltage across $R_{sense}$. Because $R_{small}$ is negligible, the bandwidth limitation is determined by $R_{sense}$. How small $R_{sense}$ can be is limited by the input-referred noise from the signal path following $V_{sense}$. Smaller values of $R_{sense}$ will result in better frequency response characteristics since the pole created by $C_{par}$ and $R_{sense}$ will be at a higher frequency. However, the resulting voltage $V_{sense}$ will be smaller and more susceptible to noise. A larger value of $R_{sense}$ will result in worse frequency response characteristics, but better signal-to-noise characteristics at lower frequencies.

Figure 7:
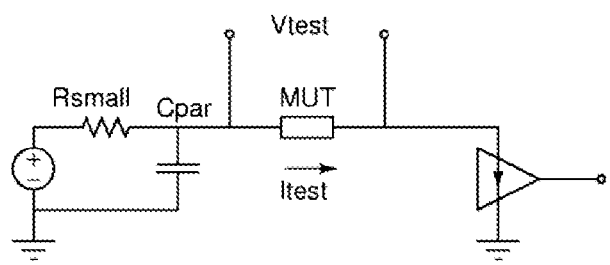
FIG. 7 is a circuit diagram of a transimpedance amplifier.

FIG. 7 illustrates an embodiment of our disclosure involving a device using a voltage drive with a transimpedance amplifier as both a low impedance sink and current measuring device. The input of a closed-loop transimpedance amplifier is designed to have a low input impedance (e.g., <100 times smaller than MUT) over the specified measurement bandwidth. Because of this, the errors caused by current shunting through parasitic capacitances ($C_{par}$) are negligible.

Figure 8:
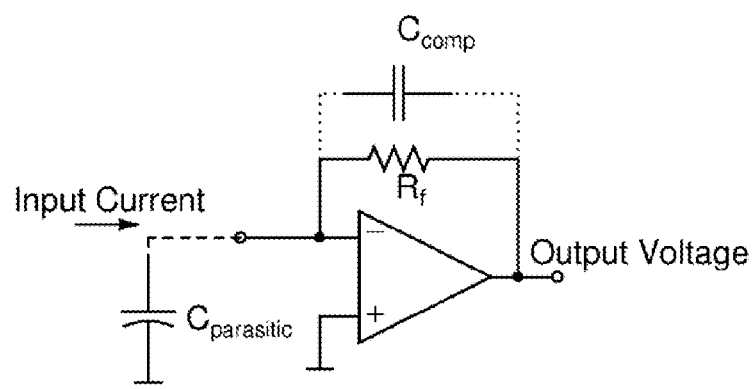
FIG. 8 is a circuit diagram of a previously reported transimpedance amplifier.

FIG. 8 illustrates a previously reported [Grimnes 2008] embodiment of a transimpedance amplifier. It consists of a voltage input operational amplifier with a feedback resistor ($R_f$) and a compensation capacitor ($C_{comp}$). These transimpedance amplifiers suffer from poor bandwidth at large transimpedance gains (Rf) and parasitic capacitances ($C_{par}$), because $C_{par}$ and $R_f$ form a pole in the feedback path, which can fall below the loop crossover and cause instability. The solution is to use a lead compensation capacitor, but this introduces a closed-loop pole that severely limits the bandwidth.

Our disclosure entails the use of a transimpedance circuit in an LBTI apparatus that converts a current to a voltage and having at least the following properties:
1. The output voltage may be an accurate and reproducible representation of the input current, although not necessarily linear;
2. The transimpedance circuit may be stable over a wide frequency range (approximately 1 kHz to approximately 10 MHz, for example) despite relatively high parasitic capacitance Cpar (up to approximately 100 pF, for example).
3. The transimpedance amplifier may be capable of converting an input current to an output voltage without introducing significant phase delay, phase error, or phase distortion over the desired frequency range (a typical target for phase error is less than approximately 1°)
4. The input to the circuit has low impedance (e.g., <100 times smaller than MUT).

Figure 9:
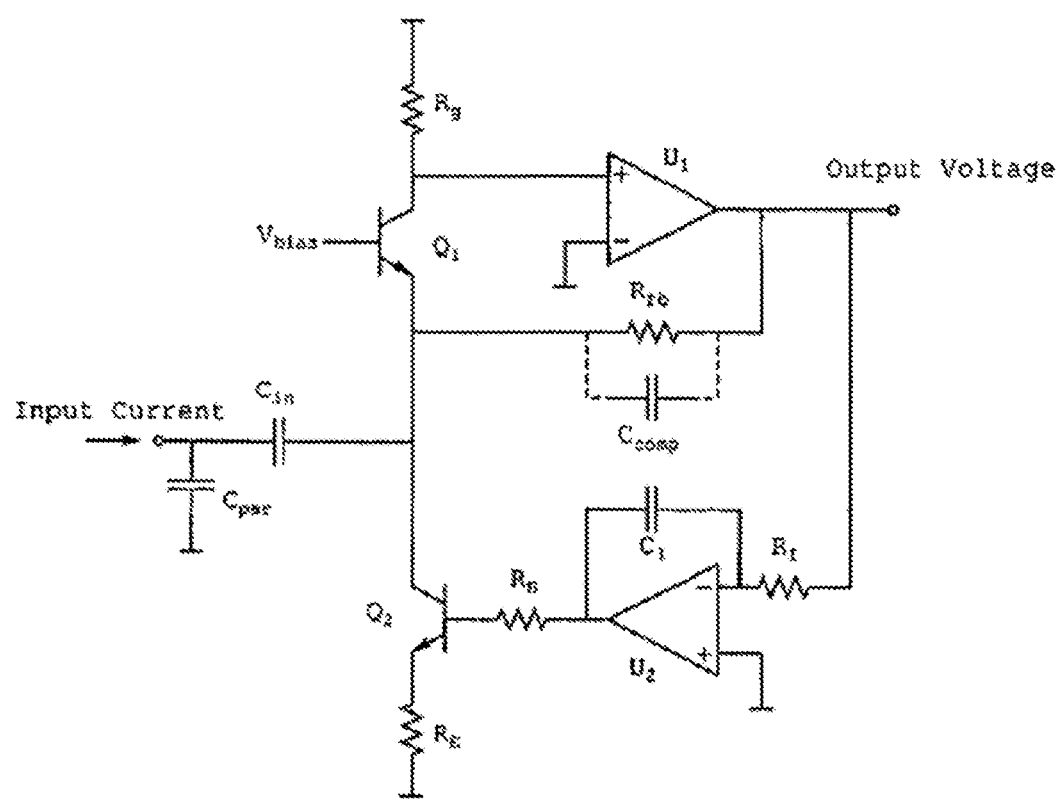
FIG. 9 is a circuit diagram of a transimpedance amplifier for LBTI measurements

FIG. 9 depicts an embodiment of a transimpedance amplifier for LBTI for wide bandwidth impedance measurement, in accordance with principles of the present disclosure. The amplifier may include a current (such as, e.g., alternative current (AC)) signal input and voltage output proportional to input. Within the amplifier passband, $V_{out}=I_{input}*R_{fb}$. $C_{in}$ is a dc blocking capacitor. $Q_1$ may be configured as a common-base input stage biased by $V_{bias}$ and current through $Q_2$. While bipolar transistors are shown for $Q_1$ and $Q_2$, many types of transistors could be used instead, including complementary metal-oxide semiconductors (CMOS) or junction gate field effect transistors (JFET). Effective open-loop input resistance at the emitter of $Q_1$ is the reciprocal of the transconductance of $Q_1$ ($g_m=I_{bias}/V_t$).

AC current through the emitter of $Q_1$ appears at its collector and results in an AC voltage drop across $R_g$ that is amplified by $U_1$. $U_1$ is a wide bandwidth voltage amplifier with open loop gain A, which must be much greater than unity in the amplifier passband. The overall open loop gain may be approximately $L=R_g/R_{fb}A$. The input current through $R_{fb}$ may be attenuated by a factor of $K=L/(1+L)$; for large L, K is nearly unity, which makes the output voltage proportional to the input current. $C_{comp}$ may be used to improve the phase margin of the overall amplifier.

The combination of $Q_2$, $R_B$, and $R_E$ behaves as a voltage-controlled current source (VCCS). $R_E$ serves the purpose of increasing the effective resistance at the collector of $Q_2$ and reducing the shot noise contributed by $Q_2$ [Avestruz, A-T, Rodriguez, J. I., Hinman, R. T., Livshin, G., Lupton, E. C. and Leeb, Sl. B., "Stability considerations and performance of wide dynamic range, ambient light active rejection circuits in photodiode receivers" Proc. Of Am. Control Conf., 2004. (Avestruz 2004) which is incorporate herein in its entirety by reference]. This VCCS is controlled by an integrator composed of $U_2$, $C_I$, and $R_I$, which in the closed-loop both sets the high pass corner frequency for the amplifier and direct current (DC) level at the output.

The following are the components for FIG. 9:

| | | |
|---|---|---|
| Q1 & Q2: BFP405 | U1: ADA4899 | U2: OPA357 | Rg = 430 Ohms |
| RE = 300 | Rfb = 430 | RI = 10k | CI = 1 uF |
| RB = 5k | Ccomp = not placed | Cin = 10 uF | |

Cpar is a parasitic capacitance, not placed by design. It is typically smaller than 100 pF. A benefit of this type of transimpedance amplifier is that the open-loop pole that is created with $C_{par}$ is a function of the effective resistance $r_{e1}=1/g_{m1}$ instead of $R_{fb}$. A typical value for $r_{e1}$ is 5 Ohms, while a typical value for $R_{fb}$ is 500 Ohms. The open-loop pole is approximately 100 times larger when the transimpedance amplifier in FIG. 9 is used, and as a result, the circuit bandwidth can be made much higher. Operational amplifier $U_1$ can be a voltage-input type or current-input type.

Digital Signal Processing

The digital signal processor (DSP) shown as element 111 of FIG. 9 and element 122 of FIG. 3 performs multiple functions. For example, one function may be to extract certain information from the digitized signals taken from the ADCs (109, 119, 125, etc.). One method for measuring transfer impedance is to apply a sinusoidal signal to tissue, and measure the resulting sinusoidal current and voltages that result at different electrodes. Transfer impedance may include, but is not limited to, the ratio of the measured differential voltage and the measured current. A sinusoid can be represented by three parameters: amplitude, frequency, and phase. When measuring transfer impedance, the material is typically assumed to be linear, and as a result, the frequency of the measured signals is the same as the frequency of the applied signal which is known. Characteristics in the system, however, will change the signal amplitude and phase. Therefore, the two exemplary parameters to extract may include, but are not limited to, amplitude and phase. In some embodiments, transfer impedance amplitude may equal to the amplitude of measured voltage and amplitude of the measured current. The transfer impedance phase may equal to the difference between measured voltage phase and current phase.

Figure 10:
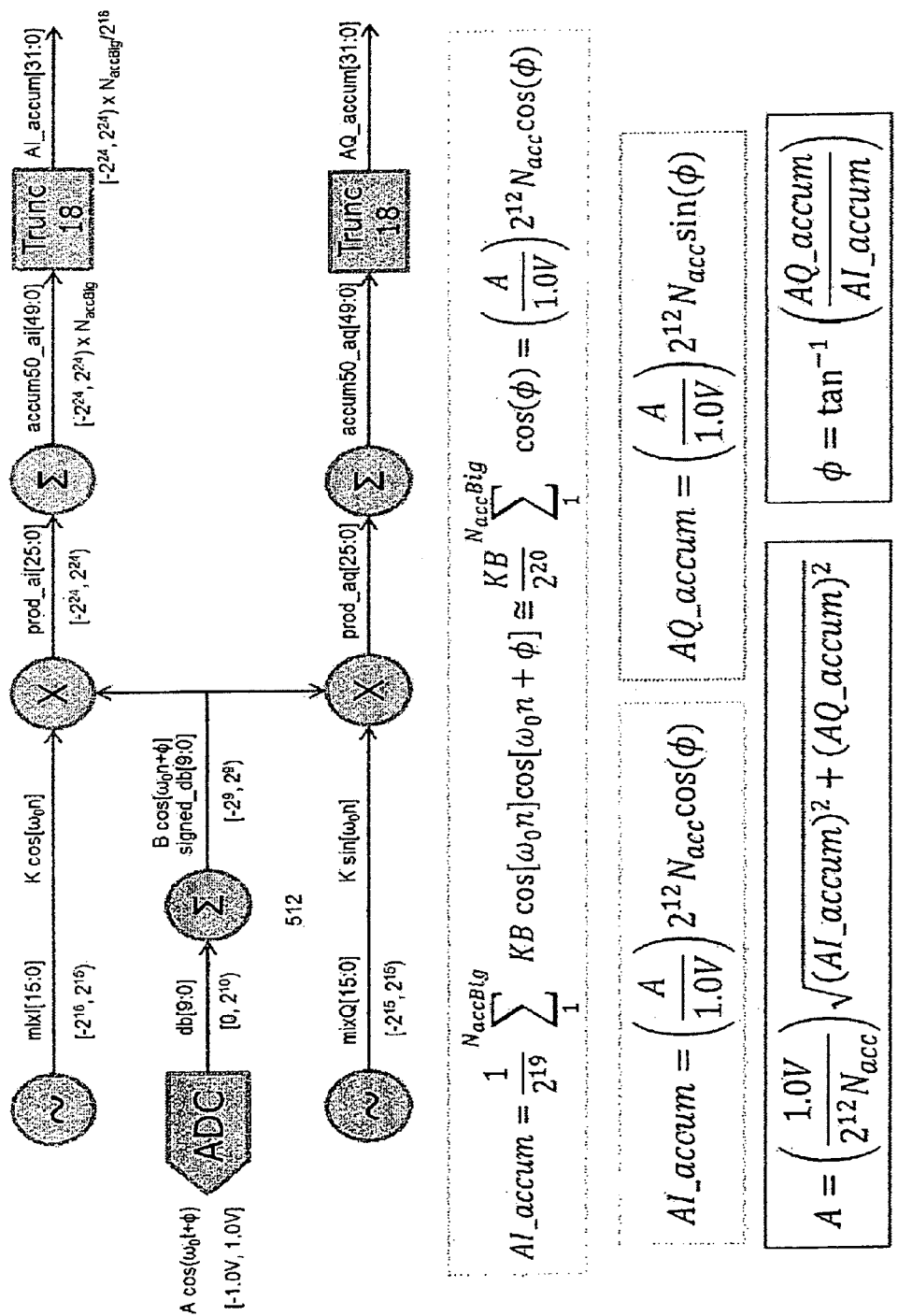
FIG. 10 is an implementation of a lock-in amplifier using digital signal processing

FIG. 10 shows one implementation of another element of our disclosure—use of a digital lock-in amplifier. Using equations shown in FIG. 10, for example, amplitude and phase of a digital sinusoidal signal at the output of an ADC can be calculated. Signal phase is relative to phase of a reference oscillator or oscillators. For example, in FIG. 10, two oscillators are shown whose outputs are 90° out of phase. Those of ordinary skill may recognize that any suitable number of oscillators may be used.

By using a lock-in amplifier like the one shown in FIG. 10 to calculate amplitude and phase of measured current and voltage, transfer impedance can be easily calculated. For example, if amplitude of measured voltage signal is $A_V$ and amplitude of measured current signal is $A_I$, then amplitude of transfer impedance is $A_Z=A_V/A_I$. Likewise, phase of transfer impedance would be $\varphi_Z=\varphi_V-\varphi_I$.

Another element of the disclosure includes multiple "lock-in" amplifiers operating in parallel so that LBTI can be measured and calculated at multiple frequencies simultaneously. In such an embodiment, the drive signal is the sum of $N_{sig}$ sinusoids at each at a different frequency. For linear materials, such as human tissue, the resulting voltage and current signals will also comprise a sum of $N_{sig}$ sinusoids, but the amplitudes and phases of each sinusoid may be different. The measured voltage and current signals are each passed through $N_{sig}$ lock-in amplifiers, with the reference oscillators of each lock-in amplifier tuned to one of the $N_{sig}$ frequencies of the drive signal. This allows the simultaneous FTI calculation at multiple frequencies which can result in faster measurements. FTI may include, but is not limited to, four-port transfer impedance which means given at least one pair of drive electrodes, and at least one pair of voltage sense electrodes, the ratio of the differential voltage to the driven current. In the alternating-current (AC) case, voltages and current are complex numbers, and so the transfer impedance is a complex number.

Drive Equalization Using a Pre-Measurement

A purpose of this element of the disclosure is to maximize signal-to-noise (SNR) of impedance at each frequency measurement point and for each electrode configuration. As outlined below, we perform a first scan (pre-scan) over frequency using a small current drive to avoid saturating any of the electronics. The scan can be performed quickly by reducing the integration window (which is an integer number of sinusoidal drive cycles), and hence increasing bandwidth and subsequent channel settling speed. To increase scan speed further, fewer frequency points can be measured if the expected transfer function response of the material-under-test is smooth; in this case, an interpolation, or other approximation method is sufficient when determining drive level for actual high resolution measurement.

The results of this pre-scan may be measured current and voltage data at specified frequencies. The voltage drive at each frequency may be determined based on, among other things, the following constraints:

maximize $V_{drive}$ such that $$\begin{cases} V_{meas} < \alpha V_{sat} \\ I_{meas} < \beta I_{sat} \end{cases}$$

where $V_{sat}$ and $I_{sat}$ are the voltage and current where the measuring system saturates, and $\alpha$ and $\beta$ are margins that depend on the expected accuracy of the pre-scan. In general, using the information from the pre-scan, two separate high resolution scans that separately maximize the SNR of the real (in-phase) and imaginary (quadrature) channel are possible.

The two figures below show a more detailed example of a portion of the voltage sense channel (FIG. 3, element 115), and the current sense channel (FIG. 3, element 110).

Figure 11:
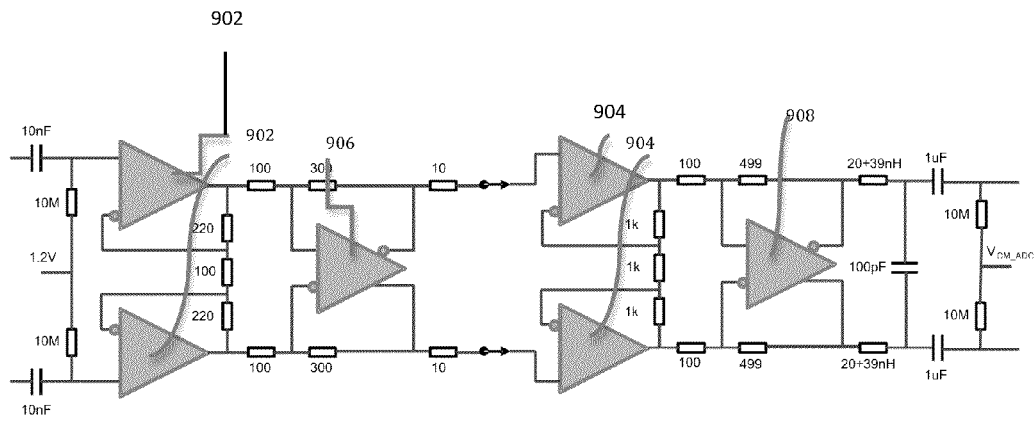
FIG. 11 is a schematic drawing of a portion of voltage sense channel.

The following components are used in FIG. 11:
902—ADA4817-2 (two opamps in one package) 904—ADA4817-2 (two opamps in one package)
906—Dual opamp: OPA2683 908—Differential opamp: ADA4938-2

Figure 12:
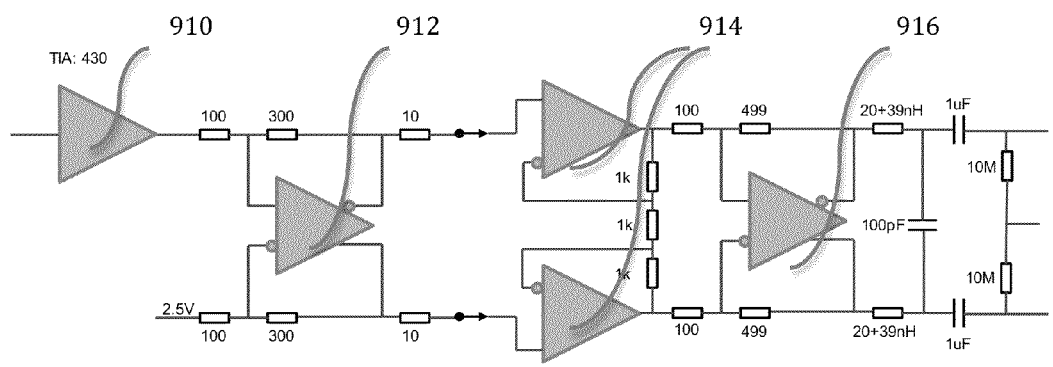
FIG. 12 is a Schematic drawing of portion of current sense channel.

The following are the component values in FIG. 12:
910—Proprietary transimpedance amplifier with a gain of 430 Ohms (shown in FIG. 9)
912—Differential opamp: ADA4938-1 914—Dual opamp: OPA2683
916—Differential opamp: ADA4938-2

The details of a specific implementation of the pre-measurement disclosure are outlined below.

The VGA that controls drive signal amplitude is digitally controlled and has a range of settings Nvga=0-4095, where a setting of Nvga=0 results in a signal amplitude of 0, and a setting of Nvga=4095 results in a maximum signal amplitude. The VGA output may be connected to a suitable resistor that limits current to a peak max of $I_{max}$. The peak-to-peak maximum amplitude at the resistor is $V_{max}$ (occurs when Nvga=4095). The peak-to-peak amplitude at the surface of the skin is a function of the current limiting resistor, the contact impedances, the tissue impedance, and any other impedance in the signal path.

The upper bound of the dynamic range of the voltage sense channel and current channel are set by the ADC input range. The largest input voltage "$V_{sat}$" is equal to the largest input voltage to the voltage ADC divided by the gain of the voltage channel. Specifically, if the ADC range is $V_{ADC}$ and the gain of the voltage chain is $G_V$, the largest input voltage signal is $V_{ADC}/G_V$. Likewise, the current channel gain is $G_I$, so the largest input current is "$I_{sat}$" which is equal to $V_{ADC}/G_I$. The ratio of $V_{sat}$ to $I_{sat}$ creates an impedance value defined as $Z_{sat}=V_{sat}/I_{sat}$. When the measured FTI value is larger than $Z_{sat}$, the voltage channel sets the maximum current that can be applied to the tissue, since the voltage at the input of the voltage channel ADC is larger than for the current channel ADC. If the measured FTI is smaller than $Z_{sat}$, the current channel sets the limit of the applied current.

Exemplary Method:
1. Set Nvga0=100
2. Select one electrode configuration and one frequency and apply signal to tissue.

3. Set the integration window of the "lock-in" amplifier to a desirable value that can be smaller than the typical setting.
4. Measure the differential voltage between the two voltage electrodes ($V_{meas}$), and the current into the TIA ($I_{meas}$).
5. Calculate $Z_{meas}=V_{meas}/I_{meas}$
6. If $Z_{meas}>Z_{sat}$, then set Nvga=Nvga0*$V_{meas}/V_{sat}$*α
7. If Zm<Zcal, then set Nvga=Nvga0*lm/l_lim*alpha, where alpha is some "backoff" value like 0.9.
8. Either store the new Nvga value in a table for subsequent use, or use that value immediately to modify the VGA setting and run a new measurement.
9. Adjust the integration window for the desired data quality
10. Measure Vm and Im again with the new VGA setting and integration window
11. Calculate FTI parameters (amplitude, phase, R, X, etc)
12. Repeat these steps for every electrode configuration and frequency. Since the purpose of this is to approximately maximize SNR without saturating the ADCs, data quality of the first sweep does not need to be very high. To expedite overall measurement, the integration window can be made substantially shorter during the first sweep (step 4), and then larger during the second sweep (steps 9-11).

Electrode Array

Figure 13:
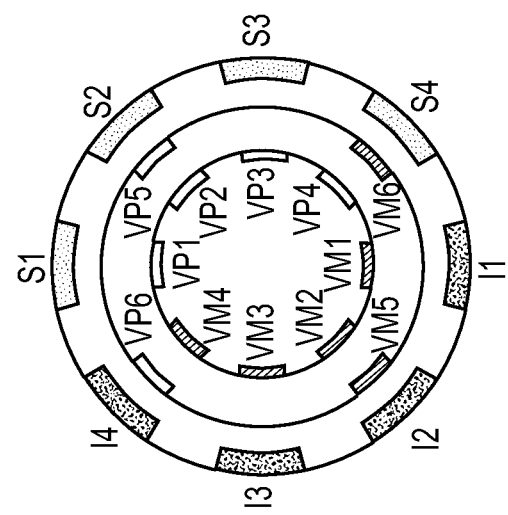
FIG. 13 is an example of an LBTI electrode array for CTI and OTI measurements.
Figure 14:
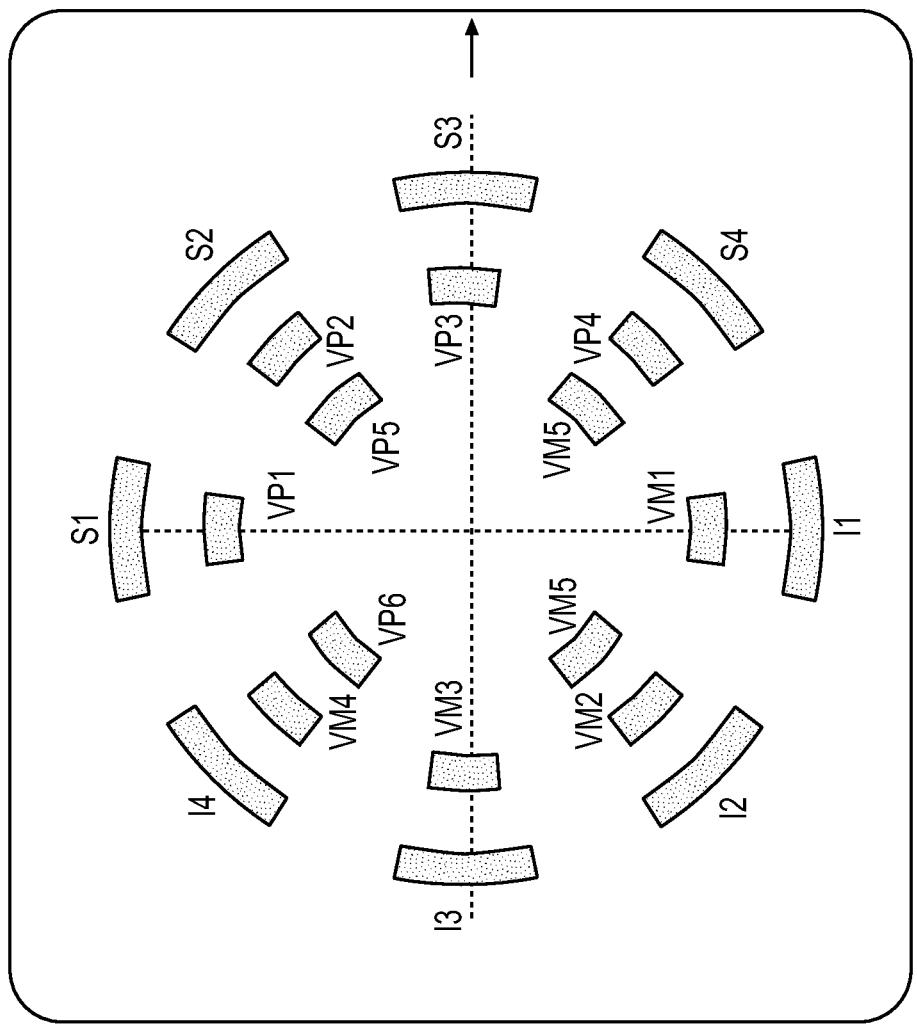
FIG. 14 is an example of electrode array whereby OTI measurements are taken in the middle ring inner ring.

FIG. 13 and FIG. 14 above show a sample electrode array configuration in which a plurality of Collinear Transfer Impedance (CTI) and (Orthogonal Transfer Impedance) OTI measurements are made with a single placement of the electrode array. CTI may include, but is not limited to, FTI with all electrodes being (approximately) collinear. On the other hand, OTI may include, but is not limited to, FTI with the line connecting the voltage sense electrodes (approximately) orthogonal to the line connecting the drive electrodes.

The table in FIG. 13 shows the different configurations of electrodes that result in CTI or OTI measurements. For example, #1 refers to the configuration where electrode S1 supplies a signal (signal source), and electrode I1 is used to sink and measure current. Voltage measured, V1, may be the voltage difference between electrodes VP1 and VM1. This particular configuration is a CTI measurement. Configurations #2, 7, and 9 are for similar types of measurements, but at approximately 45°, 90°, and 135° rotations, respectively, compared with #1. Configuration #2 uses source and sink electrodes S1 and I1, but measures the voltage difference V3, between VP3 and VM3 which are positioned on a line that is rotated 90° with respect to the line connecting S1 and I1. This results in an OTI measurement. Configurations #5, 8, and 11 are similar, but with different rotations. Configuration #4 is similar to #3, except the voltage measurement V5 is made between electrodes VM6 and VP5 and VM5 which are spaced differently than VP2 and VM2. Likewise, configuration #6 is similar to #5, except the voltage electrode are spaced differently.

Benefits of OTI Measurements

One embodiment of OTI measurements results in low FTI values when electrodes are approximately aligned with direction of anisotropy in a material. In this embodiment, maximal OTI values result when source/sink electrodes are aligned approximately 45° with respect to direction of anisotropy. If electrode S1 and I1 are aligned with direction of anisotropy, measurements made with configurations 2 and 8 should result in low FTI magnitude values and FTI phase values approximately equal to 90°. Deviations from these expected values would indicate improper alignment between the electrode array and the material being tested. As a result, these configurations can verify proper alignment and/or determine which of the several sets of electrodes will yield the most valuable and useful results for a particular electrode array placement and/or determine relative alignment of the electrode array to the direction of anisotropy. This type of configuration reduces or eliminates the need for multiple tries at electrode array placement to identify the directions of anisotropy.

Additional benefits and uses of OTI measurements include but are not limited to:

1. The transfer impedance amplitude of OTI measurements on anisotropic materials is theoretically zero and practically very small when a direction of CTI is aligned is the direction of anisotropy. By an anisotropic material, we mean a material with a (complex) conductivity tensor that is not the identity matrix. Practically, a material where the CTI depends on the orientation of the electrodes with respect to the material.
2. As a result, OTI measurements can use this "null" to confirm that the electrodes are aligned.
3. When OTI electrodes are rotated with respect to the material, the transfer impedance phase displays sharp 180° transitions as direction of CTI in the electrode array becomes collinear with the directions of anisotropy. This sharp transition can be used to determine how closely aligned the electrode array is with the material under test.
4. If the voltage sensor electrodes are equidistant from each of the drive electrodes capacitive coupling between the drive and sensor electrodes is approximately eliminated when the difference between the two voltage sensor electrodes is taken. This results in more accurate measurements, particularly at higher frequencies where capacitive coupling can be substantial.
5. By the symmetry of the topology, any capacitive coupling between the drive and sensory electrodes is eliminated when the difference between the pairs of sensory electrodes is taken. This can improve the accuracy of the measurement by eliminating parasitics due to capacitive coupling. These parasitics become pronounced at higher frequencies.
6. By orthogonality, there is no magnetic flux from the drive and sink electrodes to the sensory loop, though there may be magnetic flux still due to the current in the material if the current does not flow symmetrically between the drive electrodes. This can improve the signal-to-noise ratio of the measurement by reducing parasitics due to magnetic flux in the measurement loop. These parasitics become pronounced at higher frequencies.
7. It is not required that the electrodes be aligned with the principal directions of anisotropy of the test material. If, for example, the material is anisotropic and has diagonal conductivity and permittivity tensors ("diagonally anisotropic") and the drive electrodes are placed so that they are not aligned with any principle direction of anisotropy, the device will yield non-zero differential measurement between each pair of sensory electrodes at nearly all frequencies. This can eliminate the need for identifying the direction of anisotropy prior to measurement and simplifies and accelerates the measurements.
8. If the material is diagonally anisotropic, and if the drive electrodes are 45-degrees with respect to the closest direction of the anisotropy, the differential measurements are maximized in magnitude. One embodiment of OTL achieves its best signal-to-noise ratio in this configuration.

9. By using two or more sets of sense electrodes, there is the possibility of determining the complex conductivity of the material. When only one set is used, the complex conductivity cannot be determined in general. For example, in the DC case, the ratios of the conductivities and the magnitudes of the conductivities in the principle directions will impact the measurement, and they can be individually manipulated to yield the same differential measurement across a single differential pair of sense electrodes 10. If the material is (a) isotropic or (b) diagonally anisotropic with the drive electrodes aligned with a principle direction of anisotropy, the differential measurements yield a (nearly) zero measurement if the material's boundaries are sufficiently far away. Thus, the topology can be used easily to detect isotropic materials or alignment on diagonally anisotropic materials.

11. The topology offers a different parameterization for transfer impedance of anisotropic materials (such as muscle) that may be better correlated to the detection of evaluation of internal properties of the measured material than collinear measurements.

Because the field of bioimpedance has been focused largely on measurements of isotropic surfaces or measurements along principle directions of anisotropy, OTI measurements would have yielded zero (or nearly zero) measurements and, thus, been discarded. However, OTI can yield useful measurements of anisotropic materials and yield direct measurements of on/off angle measurements.

Figure 15:
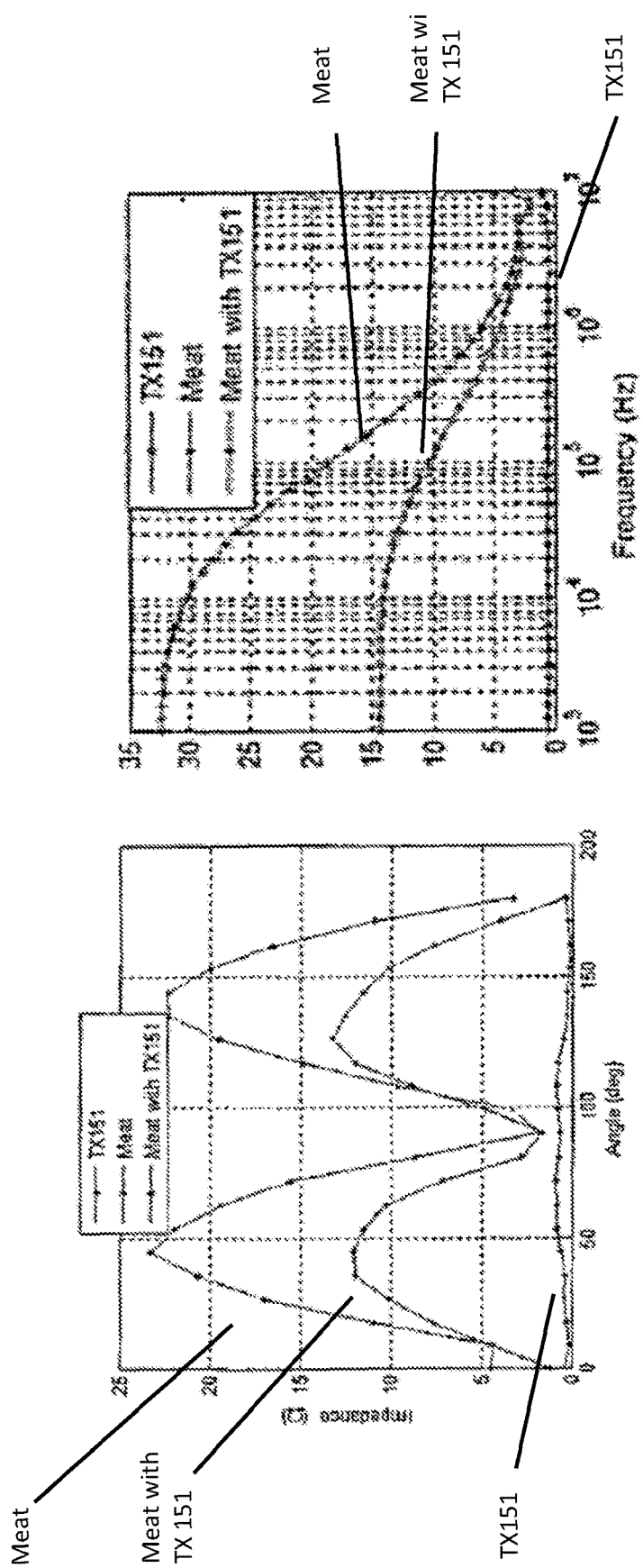
FIG. 15 is graphs with OTI measurements on meat, TX-151, and meat with a layer of TX-151 placed between it and the electrodes.

To illustrate the benefits of the orthogonal topology, consider FIG. 15 of the impedance of a piece of meat using the orthogonal topology. The meat was measured both with and without a isotropic surface (TX-151) over it.

The left plot of FIG. 15, measurements are taken at various angles at approximately 50 kHz. At approximately 0°, the measurement is minimized (nearly zero). At approximately 45° and approximately 135° with respect to either principle direction of anisotropy of the meat (the two principle directions are approximately 90° apart, meaning it is diagonally anisotropic), the measurement is maximized. In between, the measurement is between these two extremes. On the right plot of FIG. 15, measurements were taken at various frequency at approximately 45°. Note that the isotropic TX-151 yields a nearly-zero measurement while meat and meat with a layer of TX-151 yield a non-zero measurements.

Additional OTI Electrode Array Configurations

Figure 16:
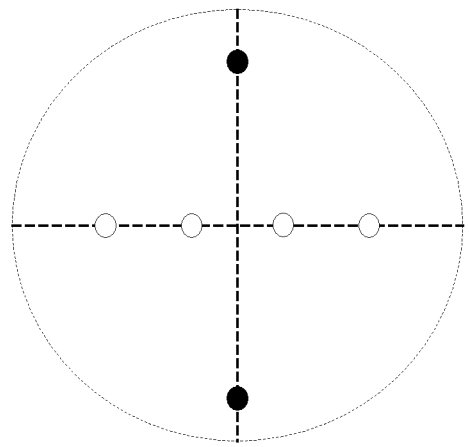
FIG. 16 is a drawing of an electrode array topology with a single pair of driving electrodes (black) and two unique pairs of sensory electrodes (white).
Figure 17:
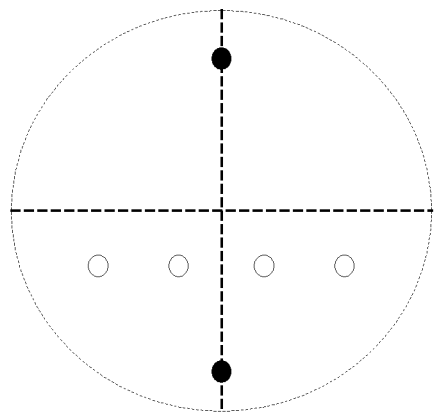
FIG. 17 is a drawing of an electrode array topology with the sensory electrodes (white) off-center with respect to the drive electrodes (black).
Figure 18:
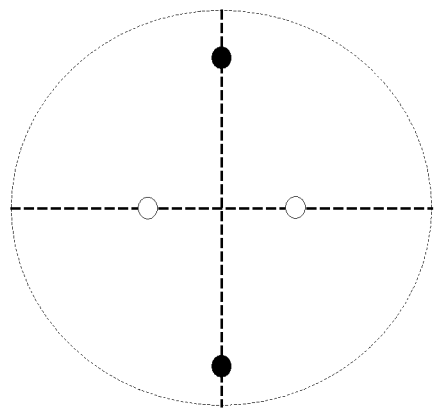
FIG. 18 is a drawing of an electrode array topology with a single pair of driving electrodes (black) and one unique pair of sensory electrodes (white).

As noted above, the disclosure embodies not just the physical layout of the electrodes but also the electrical connections and usage of the electrode array to conduct CTI and OTI measurements at multiple angles with a single placement of the electrode array on the MUT. Not intending to be limiting, there are several other electrode array geometries which can be used for OTI measurements:

FIG. 16, for example, shows two-pair OTI measurement, where one differential pair consists of inner two sense electrodes and the other differential pair consists on outer two sense electrodes. In another example, shows an array with sense electrodes off-center. Further, FIG. 18 shows use of only one pair of sense electrodes. However, any number and any suitable configurations of sense electrodes may be used within the principles of the present disclosure.

Figure 19:
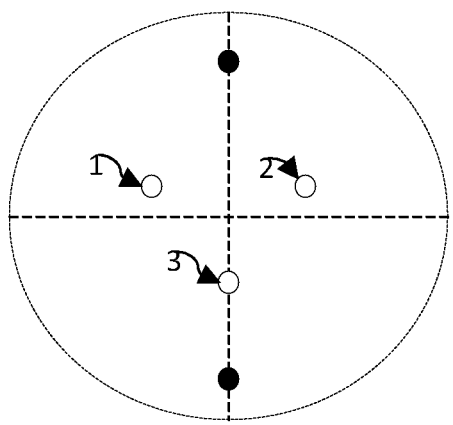
FIG. 19 is a drawing of an electrode array topology with a single pair of driving electrodes and two non-unique pairs of sensory electrodes that can provide one perpendicular measurement.
Figure 20:
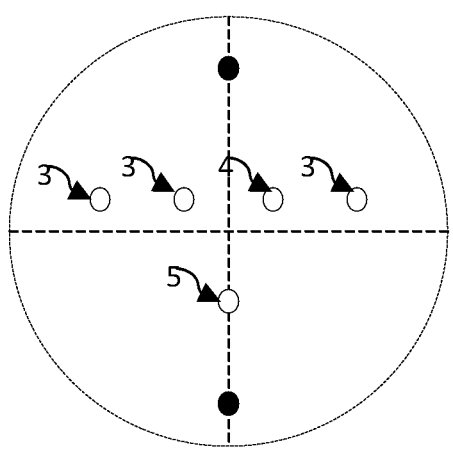
FIG. 20 is a drawing of an electrode array topology with a single pair of driving electrodes and multiple sensory electrodes that can provide multiple orthogonal measurements.

In some embodiments, the orthogonal measurement may be made without measuring a differential orthogonal to the drive electrode pair. FIGS. 19 and 20, for example, illustrate this concept. In FIG. 19, for example, a third electrode may be used as a common differential point for the measurement. In this case, the orthogonal differential measurement, denoted as $E_2-E_1$, can be obtained from measurements of $E_3-E_1$ and $E_3-E_1$ as $E_2-E_1=(E_3-E_1)-(E_3-E_2)$. This yields the same measurement benefits of topologies discussed previously. FIG. 20 is similar.

Figure 21:
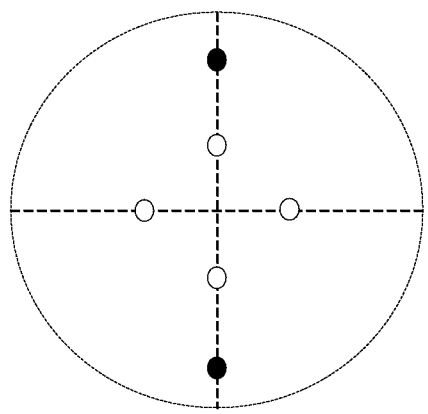
FIG. 21 is a drawing of an electrode array topology with a single pair of driving electrodes (black), a single pair of orthogonal sensory electrodes (white and perpendicular to drive electrodes), and a single pair of collinear sensory electrodes (white and collinear with drive electrodes).
Figure 22:
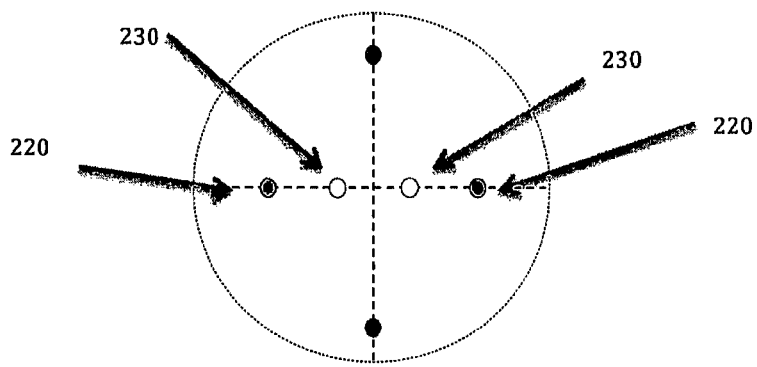
FIG. 22 is a drawing of an electrode array topology with one pair of dedicated drive electrodes (black), one pair of sensory electrodes (white), and one pair of electrodes that can be used for both drive and sensing (gray) to provide both a single collinear (horizontal) and two orthogonal (vertical) measurement.

FIGS. 21 and 22 illustrate a combination of a standard (collinear) tetrapolar electrode topology, where sensory electrodes are collinear with respect to the drive electrodes, and an orthogonal electrode topology. The combination allows for use of both electrode topologies with a single electrode head, allowing for non-zero measurements of both isotropic and anisotropic materials with a single compact electrode interface. In FIG. 21, for example, a single dedicated pair of drive electrodes may be associated with a pair of collinear electrodes and a pair of orthogonal electrodes. In general, a single drive pair can be dedicated with several sets of electrode pairs in either configuration. In FIG. 22, outer electrodes 220 may be used as both drive and sensory electrodes. As sensory electrodes, they act as another pair of orthogonal sensory electrodes. As a drive pair, they can be take an collinear measurement with the other sensory electrodes 230.

Figure 23:
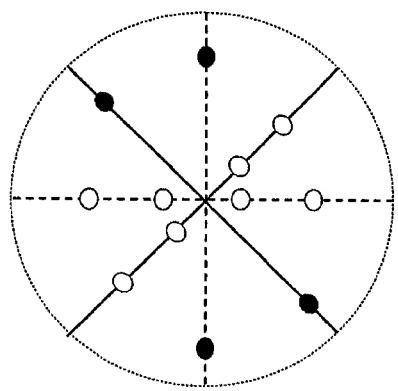
FIG. 23 is a drawing of an electrode array topology for multi-angular orthogonal measurements.

FIG. 23 illustrates revolutions of the electrode topologies. In general, this revolution can take place over any number of discrete angles. Rotating regularly over a fixed number of degrees until approximately 360° is obtained yields a topology over which both collinear and orthogonal measurements can be taken over many angles. Generally, any electrode configuration can be revolved to produce a revolved topology. The revolved topology has the advantage of producing measurements over many different angles, which can improve the characterization of the material by providing measurements can be fit with curves and, therefore, regressed. Any number of outer and inner rings may exist.

Figure 24:
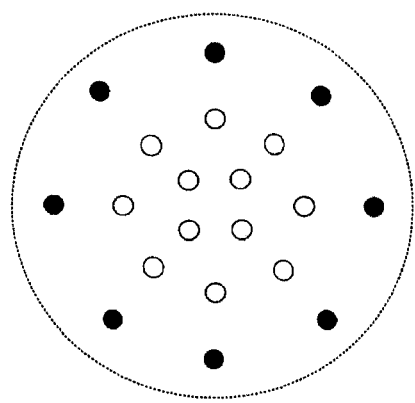
FIG. 24 is a drawing of an electrode array topology for multi-angular measurements that provide both collinear measurements, several single-pair orthogonal measurements, and two two-pair orthogonal measurement.
Figure 25:
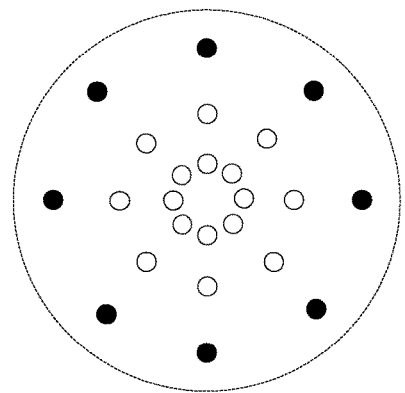
FIG. 25 is a drawing of an electrode array topology for multi-angular measurements that provide both collinear measurements, several single-pair orthogonal measurements, and four two-pair orthogonal measurement.

Turning now to FIG. 24, there is a configuration partially obtained by revolutions. There is an outer ring of drive electrodes and an inner ring of electrodes produced by revolutions. There are also two pairs of electrodes within the inner ring. In this setup, many collinear measurements can be taken over each angle, many single-pair orthogonal measurement can be taken over each angle, and a two two-pair orthogonal measurement is taken at one angle. In this setup, the two inner orthogonal measurements can be taken at 45° for maximum signal while the remaining angles provide points for angular regression. It is possible to add any number of additional electrodes to, or reduce the number of electrodes from, this setup to provide additional orthogonal or collinear measurements Multiple sets of rings can be used with different revolution angles can be used. It is also possible to space the electrodes irregularly or to place the tetrapolar sets of electrodes asymmetrically with respect to other tetrapolar sets.

Electrode Contact Verification

When making LBTI measurements, it is important to minimize contact impedance between the electrodes (element 101 of FIG. 1 and element 101 of FIG. 2) and the tissue. Large contact impedances may result in measurement errors. The disclosure in this section is a method for verifying proper contact between electrodes and tissue and notifying the user whether all or a predetermined number of electrodes in an electrode array are making contact with tissue or not speeding up measurement time and reducing the likelihood of unsatisfactory measurements.

Figure 26:
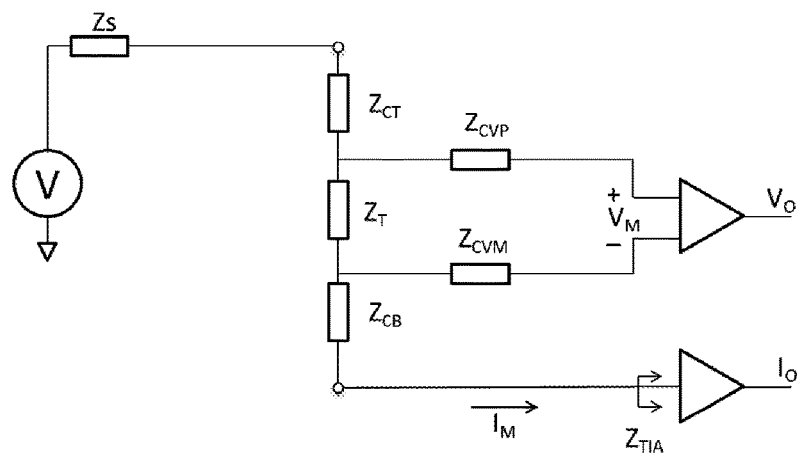
FIG. 26 is a circuit diagram of a simplified LBTI system.

In one embodiment of the disclosure, an LBTI system like the one in FIG. 1 is used in which the electrical signal applied to the tissue may be sourced using a voltage signal. The resulting current that is sunk and measured using a transimpedance amplifier is a function of the tissue impedance and the contact impedance. FIG. 26 illustrates a section of a simplified LBTI system and along with a variety of impedances. In such an embodiment, a voltage signal V is supplied and a current $I_M$ is measured using a transimpedance amplifier. The voltage $V_M$ measured using an instrumentation amplifier is approximately equal to the product of $I_M$ and $Z_T$, where $Z_T$ is the tissue impedance being measured. As a result, an accurate measurement of the transfer impedance $Z_M = V_M/I_M$ can be made if accurate measurements of $I_M$ and $V_M$ are made.

Current $I_M$ is a function of V, and the sum of $Z_S$, $Z_{CT}$, $Z_T$, $Z_{CB}$, and $Z_{TIA}$. A properly designed transimpedance amplifier has an input impedance $Z_{TIA}$ that is much smaller than the other four impedances mentioned. An impedance value of 1000 Ohms or more can be used for $Z_S$ to limit the maximum current supplied to the patient. Impedances $Z_{CT}$ and $Z_{CB}$ represent the contact impedances of the signal source electrode and current sense electrode. Ideally, these are relatively small compared to the tissue impedance $Z_T$. However, in reality, these can be relatively larger than $Z_T$ and therefore result in the current $I_M$ being smaller than desired. Depending on the electrode material, size, and other factors, the contact impedance may be larger than some threshold and result in poor measurement quality. To avoid such scenarios, it would be useful to inform a user whether the electrodes are making sufficiently good contact before a full measurement is made.

For LBTI systems in which multiple electrode configurations are used, it is also important to inform the user which electrodes are making good contact and which are making poor or no contact. This should be done in "real time" with minimal delay between changes in the contact impedance and the alert to the user.

In one embodiment of the disclosure, the process of determining which electrodes are making good contact and notifying the user may include one or more of the following steps:

1. One of multiple electrode configurations is selected. For example, S1 is selected as the signal source electrode, VP1 and VM1 are selected to measure the differential voltage, and I1 is selected to sink and measure the current.
2. A signal is applied to the tissue and the resulting voltage and current are measured.
3. The amplitude of measured voltage and current are compared against a predefined range.
4. If the current is within the desired range, a figure is shown to the user through a graphical user interface (GUI) with electrodes S1 and I1 in a particular color (green, for example).
5. If the voltage is within the desired range, a figure is shown to the user through a graphical user interface with electrodes VP1 and VM1 in a particular color (green, for example).
6. If the current or voltage are outside of a desired range, the respective electrodes are shown in a different color (red, for example).
7. A different configuration is selected, and steps 1-6 are repeated. For example, S3 might be selected as the signal source electrode, VP3 and VM3 selected to measure the differential voltage, and I3 selected to sink and measure the current. The procedure might be repeated until all electrodes have been measured in all configurations.
8. If desired, a computer can monitor the several measured current and voltages, determine if they are in the desired ranges and signal the in-range or out-of-range performance by visual, audio or combination signal.
9. If any electrode is not making proper contact, the user can adjust the electrodes while getting feedback from the GUI to verify if the contact is now appropriate.
10. Once all of the electrodes are making good contact, the user can initiate a full measurement by pressing a button or through some other means. Alternatively, a computer can automatically determine that proper contact is being made and initiate the measurement.
11. If the user chooses to perform the full measurement despite poor contact by some electrodes, the system can allow the user, but it can issue a warning after the measurement that the data may contain error due to improper contact.
12. Further, if the data is being stored for future analysis, the data files may contain a note stating that improper contact was being made by a particular set of electrodes.

Figure 27:
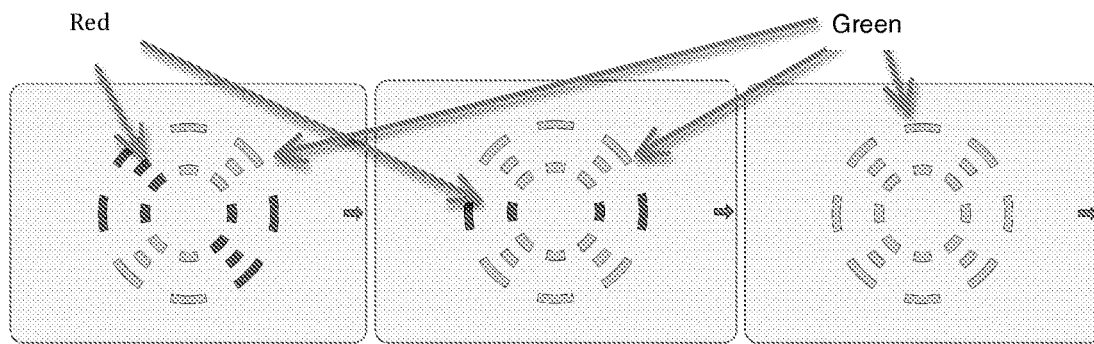
FIG. 27 is a drawing of Electrode Array with some poor contacts (left), with improved contacts but still some poor contacts (middle), and proper contacts (right).

FIG. 27 shows an example of a display that communicated whether one or more of the electrodes are making good contact and others making poor or contact. On the left, many electrodes are making poor contact. After adjusting the electrodes, the user is informed that more electrodes are making good contact, but some are still not making good contact (middle). Finally, after further adjustment, all electrodes are making good contact and the user can see this because all electrodes may be represented by, e.g., a green color (right). In addition to visual displays, any suitable means for communicating electrode contact status may be used within the principles of the present disclosure. In some instances, the devices disclosed herein may emit an audible sound for communicating contact status to a user.

Verification, Validation and Calibration

The measurement of anisotropic materials is an application for EIM. Verifying that the measurement system is operating properly can be part of design, development, qualification and calibration of EIM devices. This may require a material to be tested with known and quantified anisotropic properties.

Figure 28:
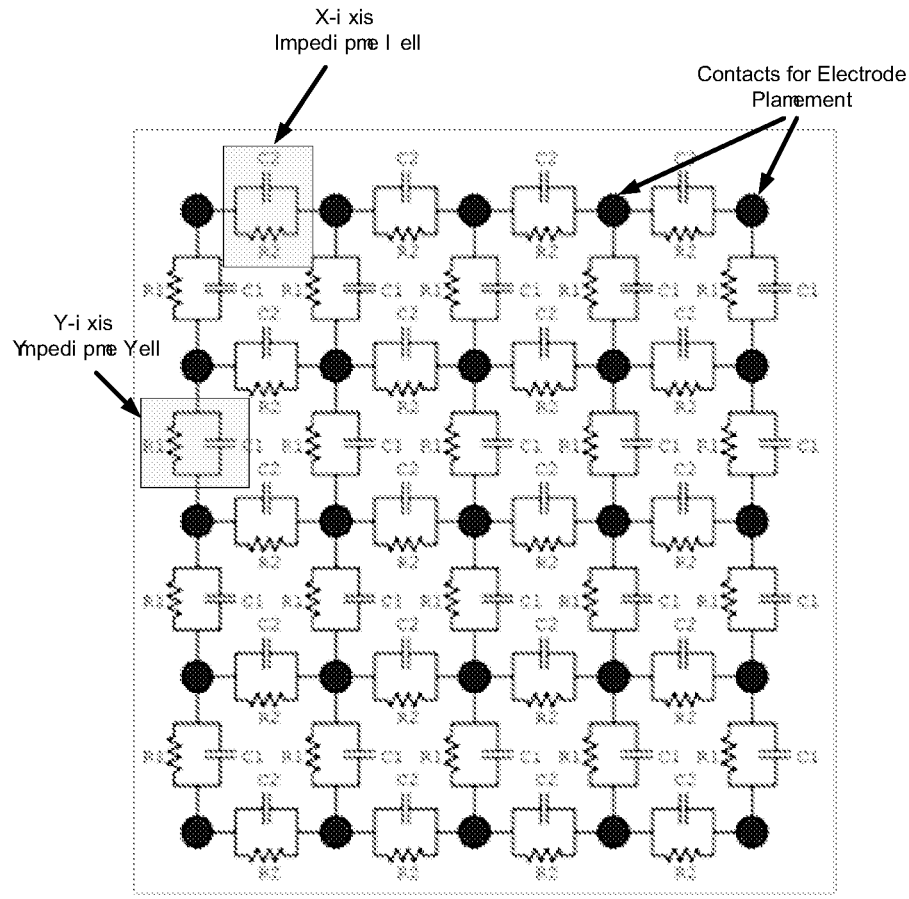
FIG. 28 is a circuit diagram of an example of an anisotropic mesh of discrete resistors and capacitors. In this diagram, the resistors and capacitors (R2,C2) along the x-axis are in general different than in the y-axis (R1,C1).

This disclosure involves using regularly connected "impedance cells" of discrete components such as, e.g., resistors, capacitors, and possibly inductors in a mesh to verify, validate, and/or calibrate an impedance measuring device. The mesh may be an emulation of a continuous anisotropic material such as muscle tissue. Although only a 2-dimensional mesh (in general different X-axis and Y-axis impedance cells) is shown in FIG. 28, three-dimensional meshes, which include depth, are possible.

Figure 29:
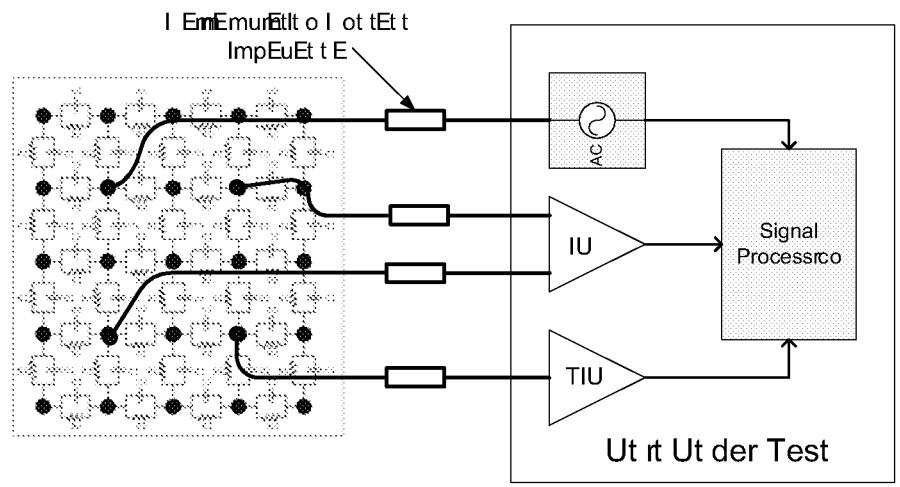
FIG. 29 is circuit/block diagram showing measuring the anisotropic emulation. In this arrangement, impedance cells can be placed in series with the driving and measuring circuits to emulate contact impedance.

FIG. 29 illustrates how one may connect a unit under test (UUT), which in general is any electrical measuring device, to the impedance mesh. In this particular illustration, AC is current driving, TIA is current measuring, and IA is voltage measuring.

Figure 30:
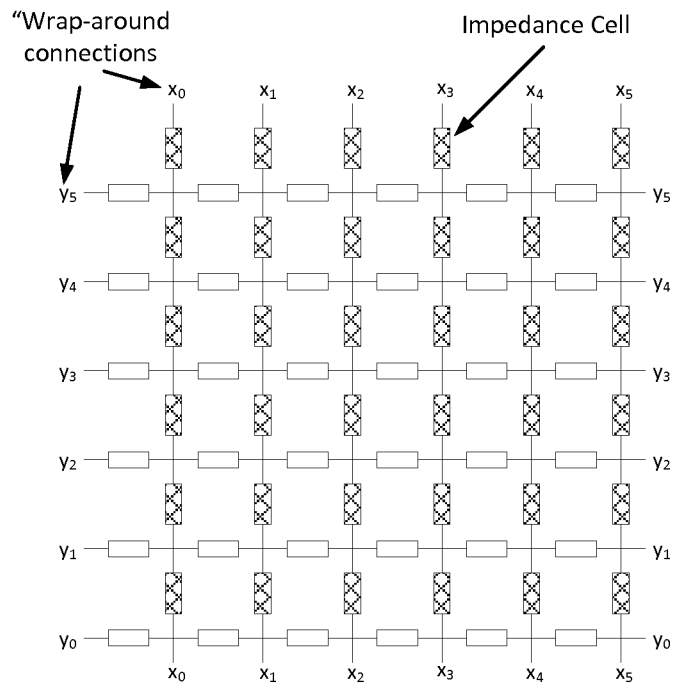
FIG. 30 is a circuit diagram illustrating that the boundaries of the mesh can be "wrapped-around" so that y0 is connected to y0 and x0 to x0, xn to xn, yn to yn and so forth to create a topological torus.

FIG. 30 illustrates one embodiment of connection of the edges of the impedance mesh in what is known as a topological torus. This results in impedance measurements on the mesh that do not depend on the absolute placement, but rather only on the relative placements of the electrodes.

Figure 31:
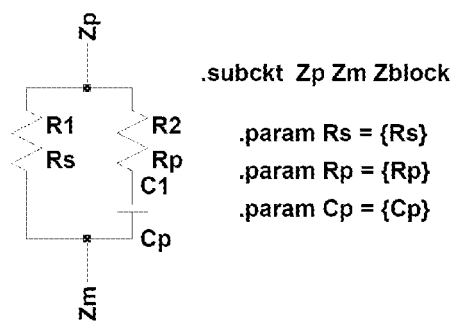
FIG. 31 shows a screenshot of schematic capture from LTSpice simulator of a particular impedance cell topology.
Figure 32:
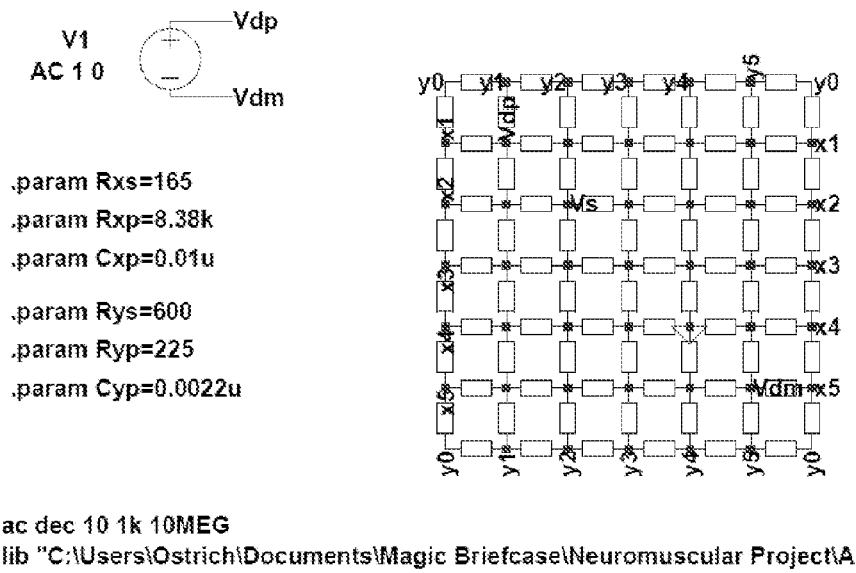
FIG. 32 shows a screenshot of schematic capture from LTSpice simulator of impedance cells connected as a topological torus.

FIGS. 31 and 32 illustrate the use of a Simulation Program with Integrated Circuit Emphasis (SPICE) circuit simulator for the purposes of determining the electrical behavior of a mesh with a particular set of component values. Anisotropic material emulation can serve various purposes, including, but not limited to, one or more of the following:

1. Verification and validation: The process of checking that a product, service, or system meets specifications and that it fulfills its intended purpose. These are critical components of a quality management system such as ISO 9000 or ISO 13485.
2. Verification: Quality control process that is used to evaluate whether or not a product, service, or system complies with regulations, specifications, or conditions imposed at the start of a development phase. Verification can be in development, scale-up, or production. This is often an internal process.
3. Validation: Quality assurance process of establishing evidence that provides a high degree of assurance that a product, service, or system accomplishes its intended requirements. This often involves acceptance of fitness for purpose with end users and other product stakeholders.
4. Calibration: Comparison between measurements—one of known magnitude or correctness made or set with one device and another measurement made in as similar a way as possible with a second device.
5. The device with the known or assigned correctness is called the standard. The second device is the unit under test (UUT), test instrument (TI), or any of several other names for the device being calibrated.

Not intending to be limiting, in one particular implementation:

The nominal standard behavior is derived from running an LTSpice AC analysis simulation for FTI of four chosen electrode contact points. The output of LTSpice analysis is a plot and data for the transfer function of this four-port transfer impedance.

The effect of component tolerances (time, temperature, batch, etc.) results in a distribution of transfer function curves. This distribution of curves can be derived by running many simulations over random distributions that are specified for each component—sometimes this is called "Monte Carlo simulation" in the industry. Also from [Wikipedia 2011]: " . . . it is common to use SPICE to perform Monte Carlo simulations of the effect of component variations on performance, a task which is impractical using calculations by hand for a circuit of any appreciable complexity." This results in tolerance specifications for the standard anisotropic emulator.

Figure 33:
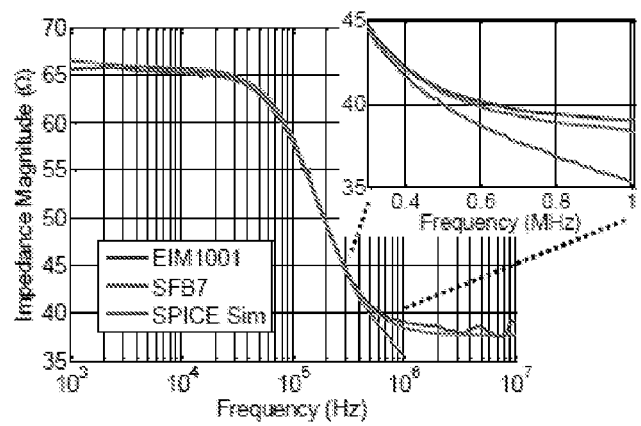
FIG. 33 is a chart of a comparison of two impedance systems CMD EIM1001 and ImpediMed SFB7) against simulation of known impedance network.

The anisotropic emulator can be used in an example verification process illustrated in FIG. 33.

Electrode Interfaces

The electrode interface may be the physical mechanism that houses the electrodes and provides a physical connection (electrical and mechanical) to the main system. Two types of interfaces are possible: conformable and non-conformable.

Conformable Material Interfaces

A conformable electrode interface may include, but is not limited to, an electrode interface that can conform to contours of, e.g., a patient's skin. Not intending to be limiting, several example conformable interfaces are discussed below. Not intending to be limiting for other possible interfaces, common to all interfaces listed below are one or more of the following attributes:

1. The electrodes may be hosted in a patch that can be any material that is able to stretch and/or flex and/or fold and/or conform. Mylar is an example material. Another example is polyethylene terephthalate (PET).
2. The entire patch may be single- or multi-layer, with at least one layer dedicated to holding the electrodes and tunneling wires to conduct an electrical signal. A multi-layer patch will have one layer dedicated to hold electrodes, and other layers dedicated to carrying signal and may be separated by a dielectric to facilitate better signal routing along with the possible inclusion of guard layers to reduce parasitic coupling between drive and sense signals.
3. The electrodes of the patch can be any conductive material (such as Ag/AgCl) or adhesive, or any deformation (such as a "bump") in the patch itself. In the latter case, cold- or thermo-forming may be used to shape the patch. The electrodes may have any shape, including half-spheres, which may offer some contact benefits over flat electrodes.
4. Either a tab, a wired interface (such as a male/female connector), or contacts on the patch itself electrically connect the electrodes of the patch with the system.
5. The electrodes themselves are arranged according to any topology, including the ones discussed previously.

Figure 34:
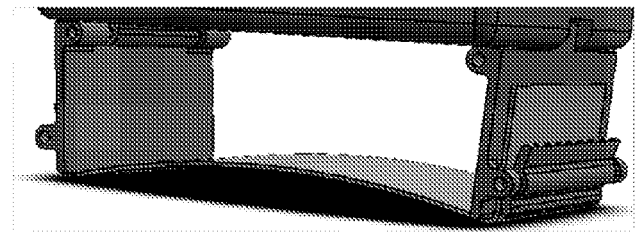
FIG. 34 is a diagram of a flexible/adhesive patch electrode interface. The patch may or may not be flexible. The holding arms may or may not rotate. The conducting contacts on the arms and the patch make contact so that the electrodes on the patch are electrically connected to the system. The figure shows a cam as the mechanism holding the patch in place.

FIG. 34 is an illustration of a conformable electrode path that is attached to two holding arms that support the path at its ends.

Figure 35A:
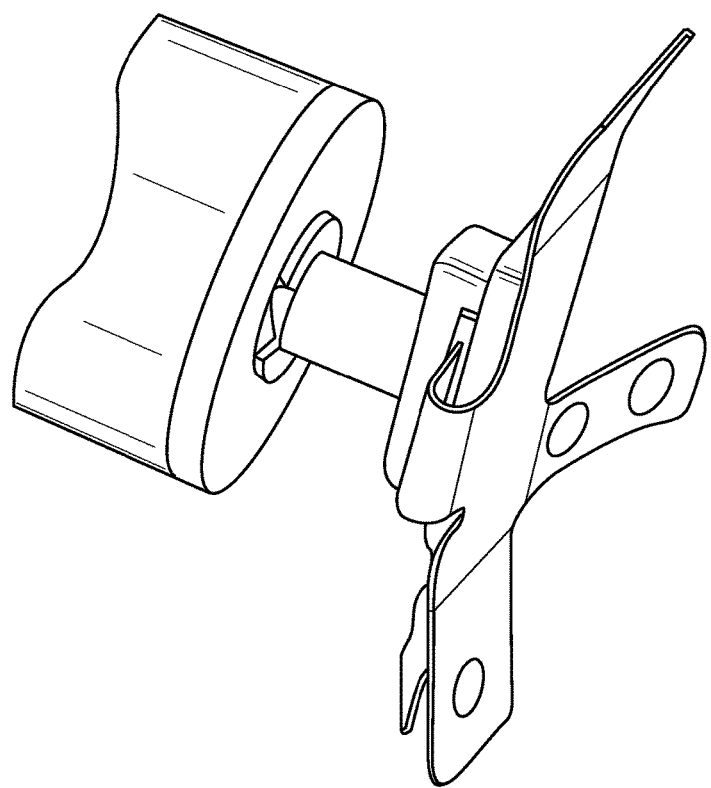
FIG. 35 shows drawings of handheld probes and electrode array patches.
Figure 35B:
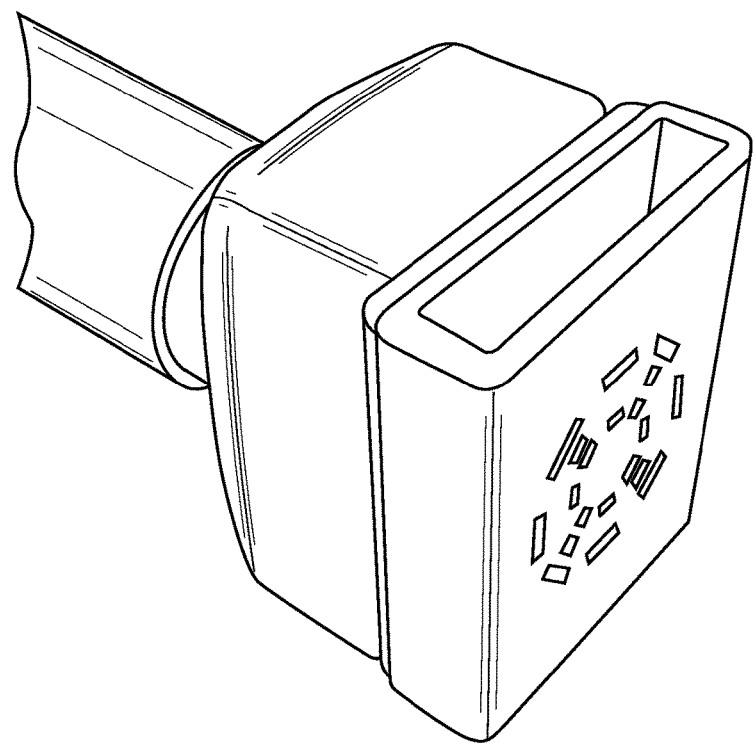

FIGS. 35a-f are illustrations of two additional embodiments of conformable electrodes. FIGS. 35a and 35b show these electrodes and FIGS. 35c through 35f give additional details about the electrodes shown in FIG. 35b. There are several advantages to these designs:

1. They can conform around cylinders, which approximates the geometry of various measurement sites of interest on a human body, including arms, legs, and forehead, where fixed, flat electrode interfaces cannot be applied.
2. They can be quickly applied and removed from a measurement site, unlike the individual strip electrode used on existing bioimpedance devices such as the ImpediMed SBF7 and the ImpediMed DF50.
3. Different patches can contain differently-sized electrode arrays with potentially different layouts that are customized for different measurement sites.
4. The patches can be quickly attached and removed from the system.
5. The patch may be disposable to simplify any possible sterilization requirements.

In the holding arm design, the holding arms may or may not move or rotate. One method for rotation is a set of hinges at the top of the arms with possible stops to stop them from rotating too far. If they are hinged, they can pivot inward as the patch is pressed inward toward the device, allowing for better conformability. If the holding arms are hinged, a (possibly low-force/torsion) spring may be used provide outward force on the holding arms to keep the patch taught as it is being pressed onto the measurement surface.

The single-mold design does not require a spring because the material itself performs this function. In the holding arm design, the connector has a set of contacts on the patch that come into contact with contacts on the holding arms, but it is not limited to this type of connector.

FIG. 36 is an example of a flat, flexible patch 36010. The patch 36010 may be coated with non-conducting medical grade adhesive in non-electrode areas to ensure the electrodes to make good contact with, for example, skin, even as the area changes due to, for example, muscle contraction.

Figure 37:
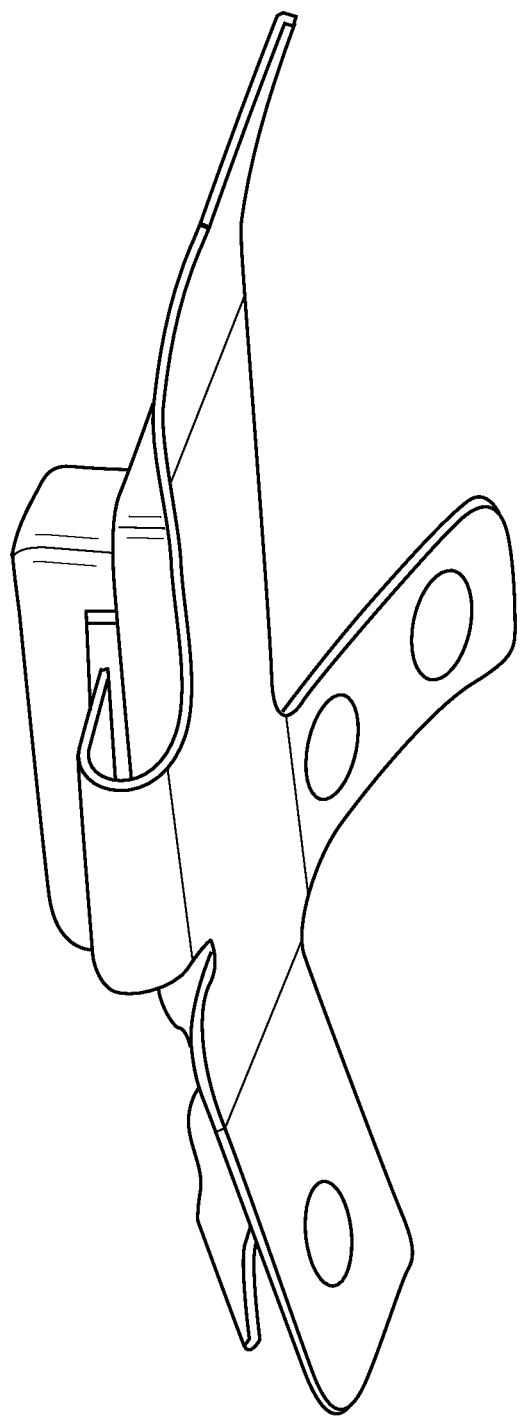
FIG. 37 is a diagram of a flexible/adhesive patch electrode interface with an example tab (center cut-out) containing wires that connect to the electrodes.
Figure 38:
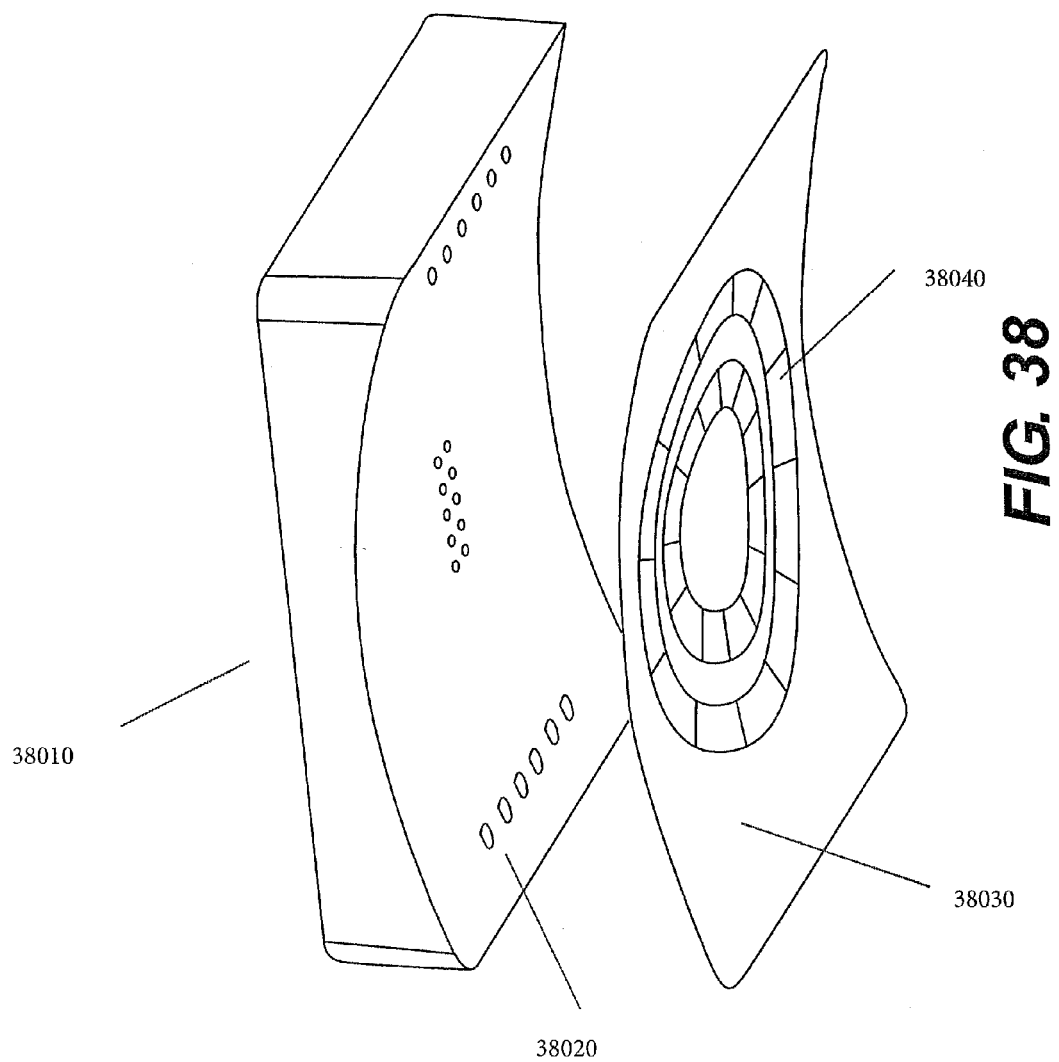
FIG. 38 is a diagram of a flexible/adhesive patch electrode interface with electrodes arranged in an example format and with an example flexible backing that contains contacts to make electrical contact with the back of the patch.

FIGS. 37 and 38 are examples of curved, flexible patches 37010 and 38030. The patches may be coated with non-conducting medical grade adhesive in non-electrode areas to ensure the electrodes 38040 make good contact with the skin. The patch 37010 in FIG. 37 can be made curved by thermoforming or cold-forming. If the patch is composed of multiple layers, some of those layers can provide curvature, and the remaining layers would be adhered to it. The patch 38030 in FIG. 38 uses a backing 38010, such as silicon-foam, with electrical contacts 38020 to at least provide curvature and to also possibly provide some resistance to pressure. The advantage of these patches is that they may not depend on adhesives or the apparatus to conform to a curved surface since curvature is achieved by back layer that generate an internal inward force.

Figure 39:
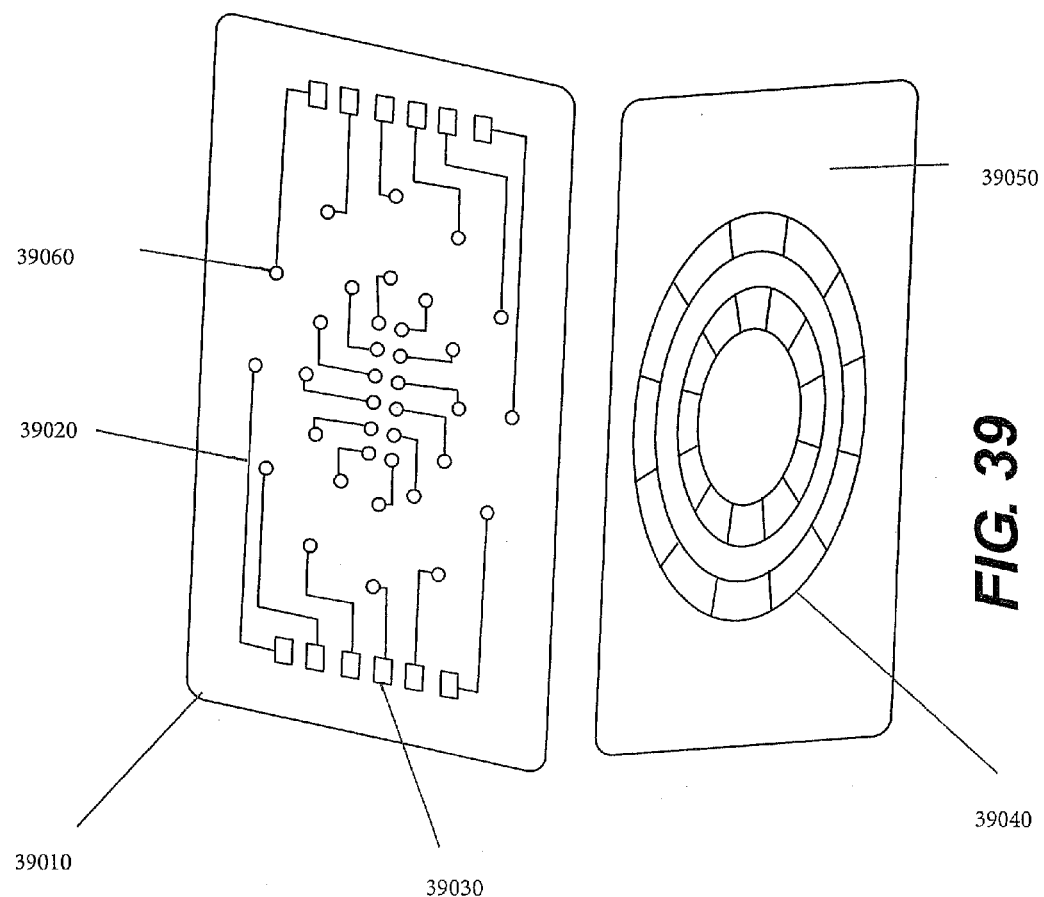
FIG. 39 is a diagram of a multi-layer patch with one end of the path acting as the face that makes contact with the surface to be measured (bottom) and the other acting as a conducting layer that carries signals to/from the electrodes to/from a backing (top).

FIG. 39 illustrates possible electrical contact backing for the designs for the flexible patches 37010 and 38030 of FIGS. 37 and 38. The front-side 39050 of the flexible patch includes electrodes 39040, and the back-side 39010 includes conductive traces 39020 that connect contacts 39030 to through-hole vias 39060 that connect the traces 39020 to the electrodes 39040. The electrical contacts 38020 in backing 38010 (see FIG. 38) provide an electrical connection from the electrodes 38040 to the main system electronics.

Conformable Actuator Interfaces

Non-conformable electrode interfaces with the ability to rotate or adjust electrode positioning have the advantage of being able to take measurements over many angles, electrode spacings, and electrode layouts by providing convenient or automatic adjustment of several electrodes. This is advantageous in settings where fine-resolution angular measurements and a high-precision force-to-displacement curve are desired. Furthermore, by using fewer electrodes, measurement errors due to electro-magnetic parasitics are reduced relative to a design where many more electrodes are used to obtain fine angular resolution.

Figure 40:
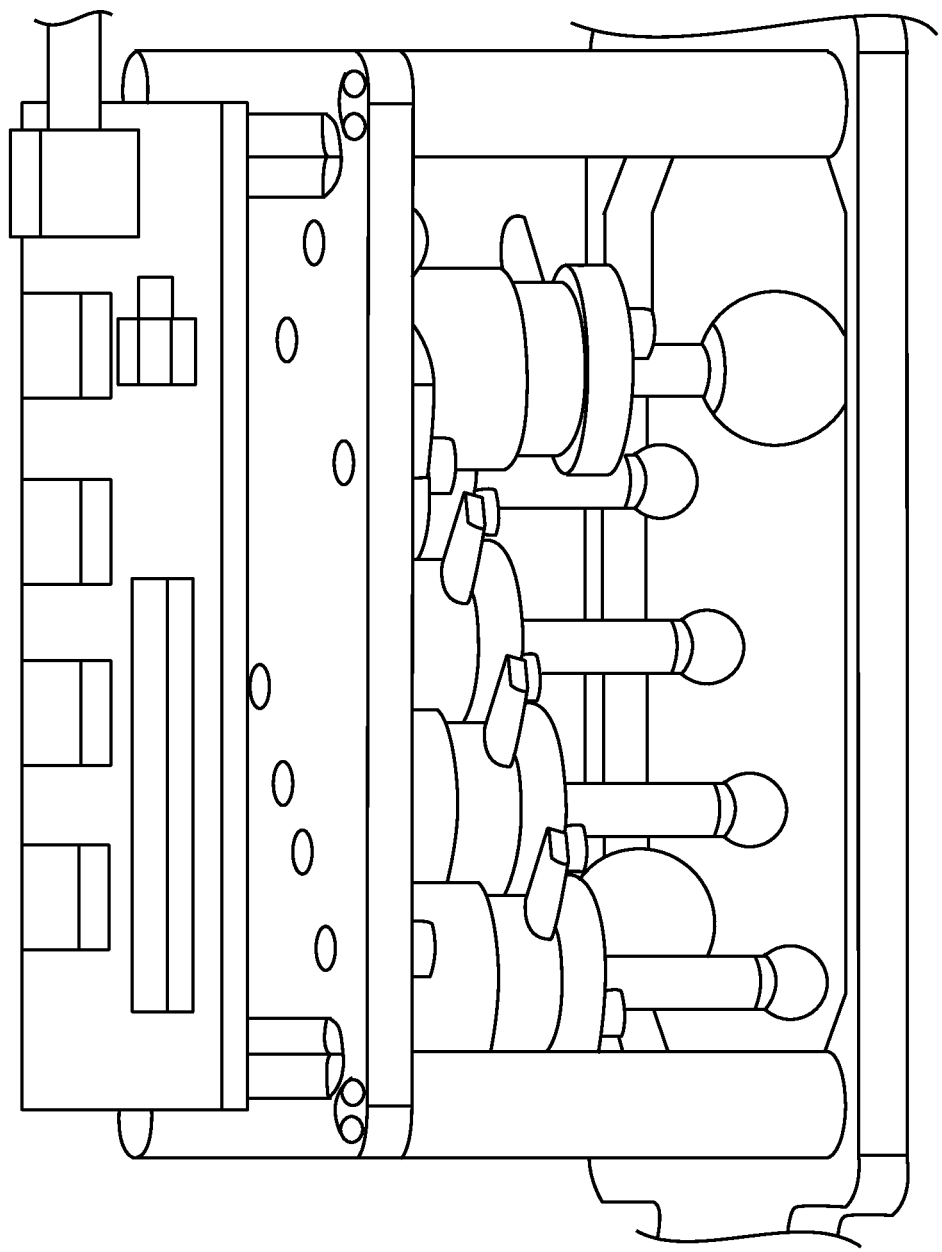
FIG. 40 is an Illustration of a non-patch electrode interface (side view).
Figure 41:
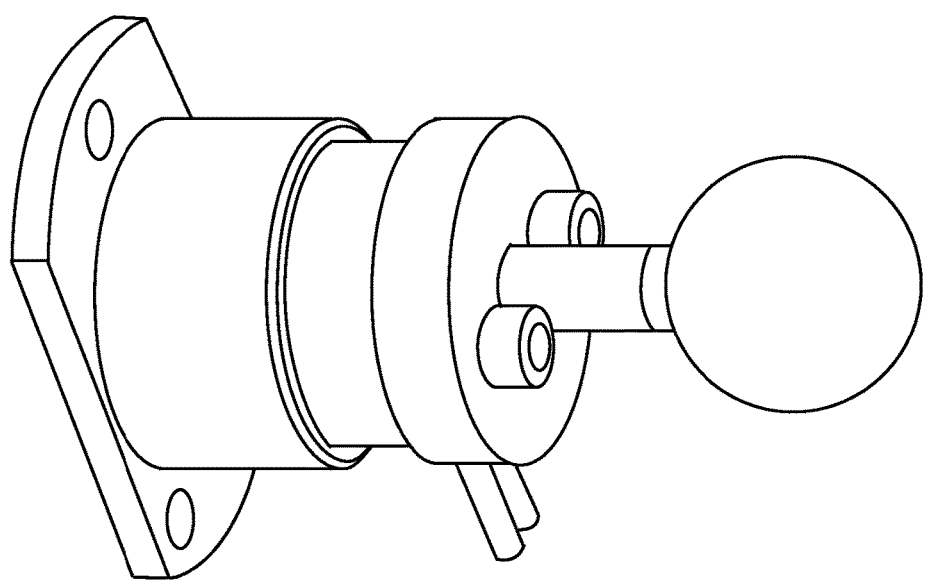
FIG. 41 is an illustration of an individual electrode that is possibly actively actuated via an electro-mechanical actuator.

FIG. 40 is an illustration of such an interface, and FIG. 41 is an illustration of an electrode from the interface. Electrode ends are shown as spheres in the diagrams, but they can be a half-sphere or any three-dimensional volume (including nearly flat shapes). Electrodes may be rigid or may provide active or passive actuation with constant or variable force. In the constant-force case, forces of the electrodes on the surface are constant for each electrode. In the variable-force case, force can vary due to applied pressure from the user or due to the device itself, which may modulate force on the electrodes. Electrodes actuation is independent of the actuation of other electrodes, or it can depend on them; for example, if forces were to be modulated in a particular order. The electrodes may also be attached to a surface that can revolve independently of entire measurement apparatus.

We also designed and constructed a magnetic linear actuator. Unlike a spring, the linear actuator provides constant force through the specified displacement range proportional to the current applied.

Rigid and Actuated Support

Any rigid attachment (via permanent adhesives, soldering of metallic contacts, screws, etc.) may be used to attach any of the electrode interfaces to the system. A non-permanent attachment also may be used whereby the electrode interface is easily removed and attached, as desired. Any of the electrode interfaces can attach via this method. The interface may also permanently or temporarily attach to a fixed or rotating surface that can be used to rotate the electrode interface and provide measurements at various angles. An advantage of any non-permanent attachment is that the patch can be replaced more easily.

The attachment may also provide variable or constant force to improve consistency of force of the electrodes on the measurement surface. In the constant-force case, forces of the electrodes on the surface are constant. In the variable-force case, the force can vary due to applied pressure from the user or due to the device itself, which may modulate the force on the electrodes.

To drive an active actuator, a closed-loop constant current driver can quickly retract or apply constant force with the electrode. The actuator has high-field, cylindrical permanent magnets (such as NdFeB) along the axis connected to a shaft that carries the spherical electrodes. The shaft moves axially inside two counter-wound magnetic coils, encased in a high permeability, low carbon steel barrel to increase force by closing the magnetic circuit. The shaft slides in a low-friction, Delrin bushing.

Figure 42:
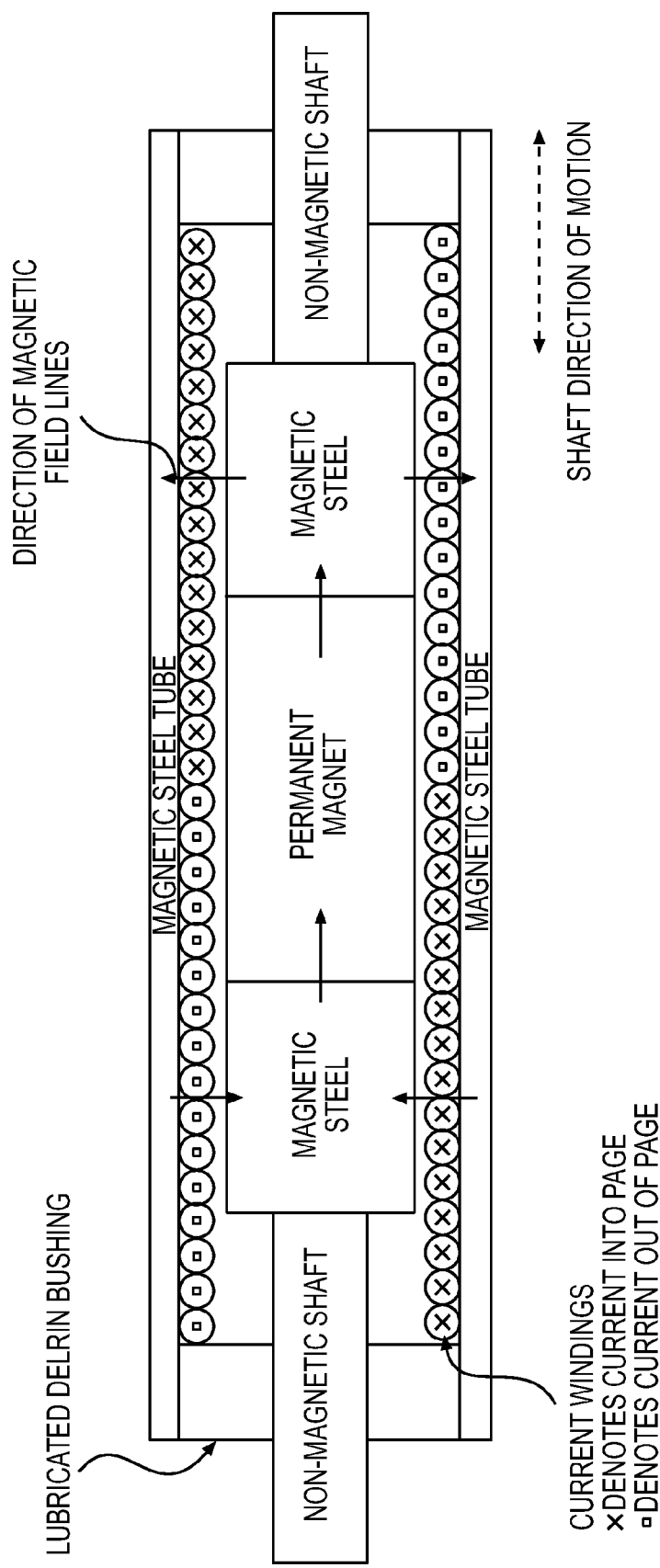
FIG. 42 is a drawing of an electromagnet Constant Force Actuator and is not drawn to scale.

An example of the "constant-force" actuator may be a dual coil, moving magnet design (FIG. 42). The windings are driven by a constant current source shown in FIG. 44 with response time less than approximately 100 ms. Magnetic steel tubes and magnetic steel endpieces result in a closed magnetic circuit. Fringing magnetic fields at the ends are actually what create the electromagnetic force. The electromagnetic actuator allows the study of the effects of tissue pressure on the impedance measurement by allowing the force, which is proportional to current to be continuously varied.

Figure 43:
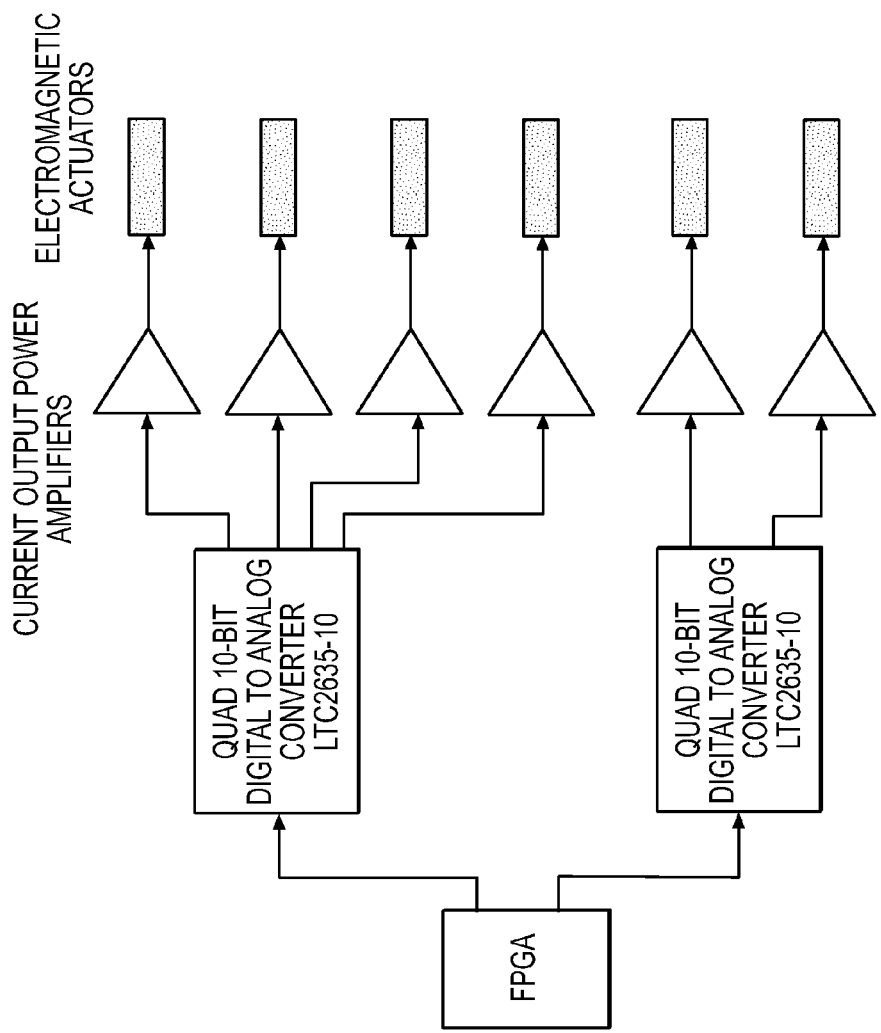
FIG. 43 is a drawing of Digitally Controlled Electromagnetic Actuators
Figure 44:
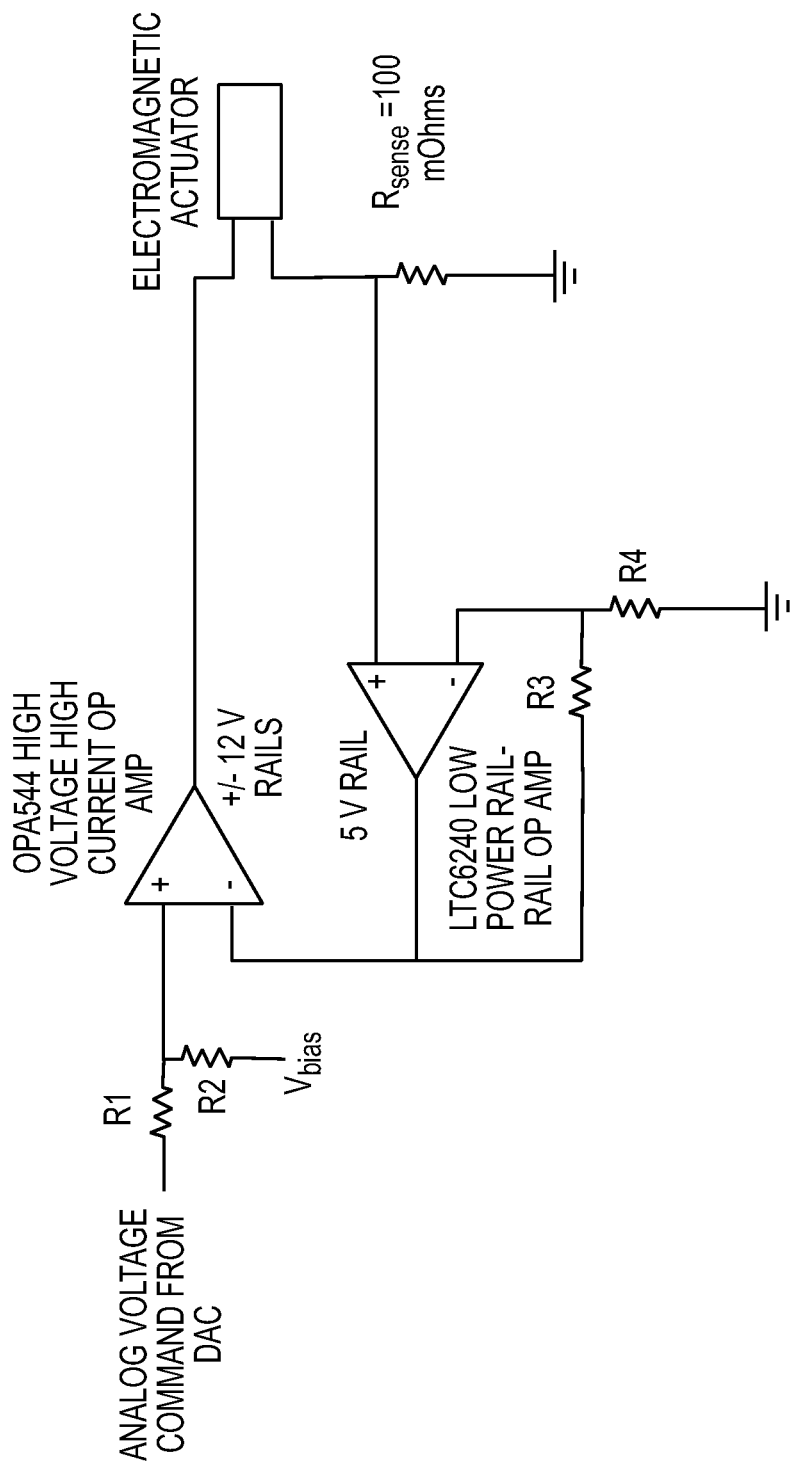
FIG. 44 is a circuit diagram of a Current Output Power Amplifier.

FIG. 43 shows an example block diagram of actuators digitally controlled by an FPGA and a DAC. FIG. 44 shows an example of a linear power amplifier with current output commanded by a voltage input from the DAC. The 10-bit DAC output voltage range is from 0 to 5 Volts. R1, R2, R3, R4 and Vbias are selected so 0V from the DAC corresponds to −2 Amps and 5 Volts corresponds to 2 Amps, and 2.5 V to 0 Amps.

Figure 45:
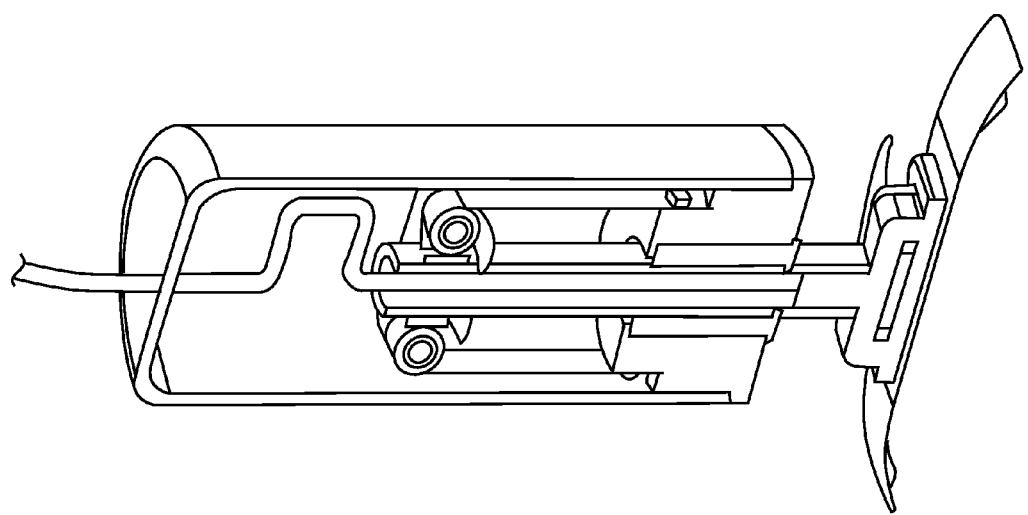
FIG. 45 is Illustration of a passive spring actuation support system attached to the electrode interface of FIG. 37.

FIG. 45 is an example of a passive spring actuation support system. One or more mainsprings may connect to the top of the actuator to extend it with constant force. The actuator may move through a linear bearing to prevent side motion and provide low friction. Both configurations provide constant force. Variable force is achieved using springs or materials that have a non-constant force-to-displacement curve, such as a coil spring or foam.

Figure 46:
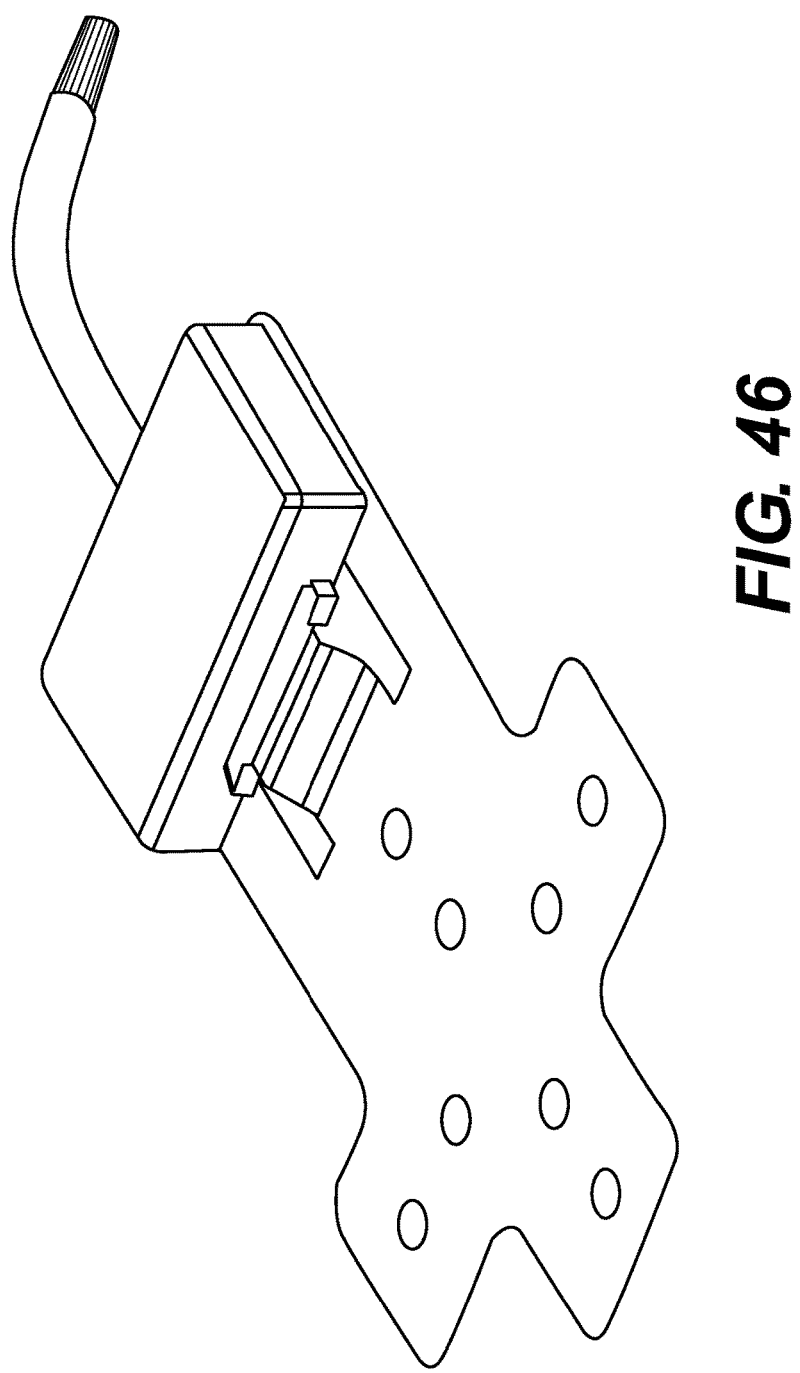
FIG. 46 is an Illustration of an example of the system attaching to the electrode interface of FIG. 37 via a hook-and-loop interface.

FIG. 46 is an example of a patch connected to the system via an interface board. In this example, the electronics subsystem may be partitioned so that part of the subsystem is permanently attached to the apparatus, and the remaining portions, an interface board, attaches to the patch itself to interface with the electrodes. The electrode interface connects to the interface board, and a wire may connect the interface board to the remainder of the electronics subsystem, namely, the signal processing board, or it may be wireless.

Additional Features and Improvements

Automatic Verification of Good Electrode Contact

As mentioned above, one type of embodiment of disclosure uses a multiple contact electrode assembly. Such an embodiment contemplates utilizing four contacts, two to generate current and two to measure voltage. Some embodiments of the disclosure use an electrode assembly with a large number of contract electrodes. Other embodiments may use a lesser number of contacts. This can enable anisotropic measurements to be made in a plurality of directions with a single placement of the electrode assembly by the practitioner. In one type of embodiment of this disclosure, each electrode in the electrode assembly makes full skin contact, resulting in sufficiently low contact impedance, particularly since it is beneficial to avoid use of ionic gel for convenience and cleanliness reasons.

In another type of embodiment, the contact impedance may be particularly low for drive electrodes. Two-port impedance between drive electrodes is a combination of tissue impedance, which is the objective of the measurement, and contact impedance between each electrode and skin. Although FTI measurements are made precisely to minimize effect of contact impedance on accuracy of measurement, having a high contact impedance can still degrade measurement to some extent. To get accurate results, contact impedance should be at most ten time as large as tissue impedance being measured.

Further, a feature can be present to verify that all electrodes in an electrode array are making good contact. The system can either verify automatically that contact is good or provide information to the user concerning quality of contact of each electrode.

For example, a graphical user interface (GUI) can contain a graphical or columnar representation of the electrode array. In one type of embodiment, after positioning the electrode array and prior to making measurements, the system makes measurements to verify good contact. If a particular electrode is making good contact, it can be displayed as green on the representation or with a plus (+) sign or other positive sign. Any suitable indicator may also be used. If an electrode is not making good contact, the display can be red or with a minus (−) sign or other negative sign. Again, any suitable indicator may be used. The user can then reposition the electrode assembly to achieve good contact for all electrodes.

With one type of embodiment of automatic verification, the system assesses all electrodes simultaneously, or in succession. The information is presented to the user either as positive, meaning that all contacts are good or non-positive meaning that one or more contacts are not good and the electrode assembly needs to be repositioned.

Without intending to be limiting, one method that is used to verify contact may include one or more of the following steps: The contact to the drive electrodes can be verified by measuring current resulting from applying a voltage to this electrode. If resulting current is within an acceptable range, then drive electrodes are considered to have good contact. Alternatively, a current can be driven through the electrodes and if resulting voltage at the electrodes is within an acceptable range, then good contact is similarly considered. Any combination of currents and voltages may be used and what is essentially two point resistance between two electrodes characterize whether contact is acceptable. The voltages or currents may be DC or AC.

Contact to sense electrodes may also be similarly measured as above with the drive electrodes. Alternatively, DC or AC voltage may be applied to the drive electrodes and current measured and voltages on a pair of sense electrodes measured. The FTI characterizes whether contact is acceptable. Also, instead of a voltage applied to the drive electrodes, a current source can directly be used. Measurement can occur quickly and repetitively and in one type of embodiment, visual and/or audio means is used to inform the user of electrode contact status before a measurement is made. Low frequencies (of approximately 1-10 kHz) may accentuate the effect of contact impedance on the overall measurement, but higher frequencies may be used as well.

The indicator for electrode contact can be one that communicates the electrode status all at once, or it may communicate which electrodes have good contact and which have poor contact.

Using the EIM1103 device which is an embodiment of the disclosure designed and built according to FIGS. 1, 2, 3, 9, 10, 11, 12, and 57, more than 20 human subjects have been tested and the contact impedance of the electrodes have been automatically verified in each case using the disclosure described. Testing of proper contact was conducted for each subject.

The EIM1103 includes primarily a handheld EIM device, a conformable electrode array, and a computer. The computer has software with a graphical user interface. When conducting an EIM test, the computer displays an image that resembles the electrode array. Immediately before conducting a test, saline, or any other suitable substance, may be applied to the skin of the subject to minimize the contact impedance.

With the EIM 1103, a button on the computer was then pressed to initiate the test. Each test has three parts: 1) good contact verification, 2) multi-frequency and multi-angle EIM sweep, and 3) data display. In the first part, an approximately 50 kHz sinusoidal voltage signal with known amplitude (approximately 10 mV peak-to-peak) was applied using the drive electrodes for approximately 100 ms and resulting current was measured at the drive electrodes. Simultaneously, the voltage signal was measured on the voltage-sensing electrodes. After, e.g., each 100 ms sweep, the measured current and voltage amplitudes were compared by the computer to preset thresholds (e.g., 5 uA for current and 1 mV for voltage). If measured current was below the threshold, the drive electrodes may be displayed in red on the PC.

Likewise, if measured voltage was below the threshold, the voltage-sensing electrodes were displayed in red. If measured current was above the threshold, the drive electrodes may be displayed in green on the PC. Likewise, if measured voltage was above the threshold, the voltage-sensing electrodes may be displayed in green. This process was repeated approximately every 200 ms and image on the computer updated, so that when electrodes were making good contact, the user would confirm with green images.

In each case, electrode images on the computer were red prior to contact when electrodes were not making contact with the subject. When the user was ready, the electrode array was pressed against the subject's skin. If good contact was made, computer images turned green. At that point, the user either pressed a button on the handheld device, or on the computer to initiate the second part of the measurement (multi-frequency and multi-angle measurement).

Constant Force Electrode Assembly

The force applied by electrode assembly to the user's skin varies depending upon the skill and strength of the operator and can vary substantially. It is useful and beneficial to have a "constant force" actuator which arranges that a relatively constant force is applied by the electrode assembly to the user's skin regardless of how tightly the operator presses the electrode assembly to the skin of the user.

Without intending to be limiting, one method to achieve a constant force applicator is a magnetic linear actuator. Unlike a spring, the linear actuator provides a constant force through the specified displacement range. The force is only proportional to current applied. To drive the actuator, a closed-loop constant current driver with a sufficiently fast response time (for example, 1 ms) can be used to quickly retract or apply a constant force with the electrode.

In one embodiment of the disclosure, the actuator may include high-field, cylindrical (NdFeB permanent) magnets along the axis which are connected to a shaft attached to the electrodes. The shaft moves axially inside, e.g., two counter-wound magnetic coils, encased in a high permeability, low carbon steel barrel to increase force by closing the magnetic circuit. The shaft slides in a low-friction, Delrin bushing impregnated with molybdenum disulfide.

In another embodiment, the design uses passive actuation. The rail of the linear guide is attached to a machined base that is then covered by a housing composed of a material such as acrylonitrile butadiene styrene or a similar material such as Somos® NeXt that attaches to the base of the device with the electronics. The carriage of the linear guide has one or more spools mounted to it that contain stainless steel extension springs that are approximately 0.007 inch thick with an outside diameter of approximately ¾-inch. The loose end of the spring attaches to the machined base, and the handle is attached to the carriage. Constant-force follows from the fact that the extension springs provide constant force.

Figure 47:
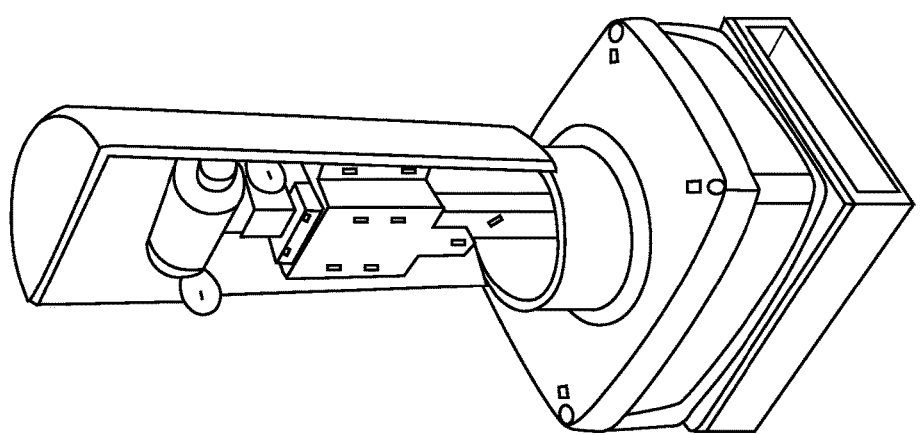
FIG. 47 is a cut away illustration of a constant force actuator

FIG. 47 is device with a portion of the housing cut away to show the inner parts.

Conformable Electrode Assembly

Although typically electrodes are flat or preshaped into some specific non-flat shape, some of the body extremities which we measure are not flat nor non-flat in any simple geometry. It is useful and beneficial to have an electrode assembly and electrode device which can conform to the shape of the body extremity or body part so that the multiple contact points of the electrode assembly are all in intimate contact with the skin.

Another element of the disclosure includes a rectangular sleeve type electrode assembly which is conformable and provides excellent multiple point contact on irregular skin surfaces. Without intending to be limiting, in one embodiment, the rectangular sleeve is rubber about 50 mils thick, and about 4 inches in height and 4 inches in diameter. The electrodes are present on the outside of the sleeve with the maximum spacing between electrode contacts being about 90 degrees of arc of the cylinder or about 3 inches. The hollow sleeve is applied to the skin so that the electrode contacts are pressed against the skin. The electrode-side will match the contour of the surface, and the side walls of the patch will bend to accommodate this temporary deforming of the rectangular sleeve. The plurality of contacts is thus pressed into satisfactory contact with the skin with sufficient force to give good contact but not so much that it is uncomfortable for the person being measured.

In one embodiment, the rectangular sleeve may be constructed from a single mold, and the electrodes may be applied via a flexible backing (a "patch") that is either adhered to the sleeve and/or wrapped around the sleeve. The patch can be any material that is able to flex/bend without breaking, such as Mylar or polyethylene terephthalate or polyimide. The patch may be wrapped around the walls of the sleeve to form electrical connections from the electrodes to the electrical contacts atop the assembly. The top of the sleeve opposite the electrodes may be adhered to a solid surface having electrical and mechanical contacts with which it can connect to the measurement system. There recently has also been information published about very thin patch electrodes described as "temporary tattoo electrodes." See, for example, http://topnews360.tmcnet.com/topics/associated-press/articles/2011/08/14/207909-stick-on-patch-proposed-patient-monitoring.htm, Aug. 25, 2011, which is incorporated herein in its entirety by reference. The use of this type of electrode device is also contemplated with our disclosure.

Graphical User Interface (GUI) which Assists Operation in Correct Operation

In one type of embodiment of our disclosure, there is verification that the steps of operation are all correctly carried out in the right order. For verification of research protocols and/or patient care protocols, it can be useful to document and verify that all of these steps have been carried out in the right order. In one type of embodiment of our disclosure, the GUI can indicate to the operator what are the correct steps of device usage, verify that the step has been correctly carried out, document and store in an electronic and/or paper file that the step has been correctly carried out including logging date, time, operator and patient (either by name or by code designation), indicate to the operator if the step is not correctly carried out and, when the step is correctly carried out, then indicate the next step to be performed.

Without intending to be limiting, a suitable measurement, in accordance with the principles of the present disclosure, may be taken by following one or more of the following steps:

1) Identify that the correct practitioner is operating the device.
2) Verify the correct identity of the patient. This could, for example, be a patient number for a non-research patient or coded patient identify for a blinded study. In the latter case, some additional identification could be provided to ensure correct patient identification while still remaining blinded.
3) Present the test to be made and verify that is the correct test
4) Show (and possibly verify that) the correct electrode assembly that is to be used and possibly determine that the electrode device is appropriate and approved for use. For verification, the software can either have the device obtain an electronic code stored in the electrode assembly to verify that it is correct or have the practitioner enter a code printed on or otherwise supplied with the electrode assembly into the device.
5) Instruct the practitioner on the correct placement of the electrode assembly for this specific test.
6) Have the practitioner verify that the electrode assembly is correctly placed.
7) Automatically verify that good contact has been made by all electrodes in the electrode assembly to the skin of the patient at the specified measurement site.
8) Automatically perform the test OR instruct the practitioner to start the test.
9) Perform the test (this requires no action on the part of the practitioner).
10) Verify that the data collection appears to be reasonable based on what is expected i.e. that electrode contact has remained good, etc.
11) If desired, verify that the data collected is reasonable based on historical measurements and on expectations i.e. that the data is in line with past measurements, measurements within the same session corresponding to the same or different measurement sites, on other patients, or on the same patient. Use error vector measurements to make these judgments.
12) If the data collection and/or data collected is not reasonable, re-perform test from step 4 or later.

13) If the data collection and data collected is reasonable, move on to the next test to be performed. If all tests are completed, instruct the practitioner that they are finished.

14) If multiple performances of the same test are desired, inform the practitioner of each in turn and verify that each test is reasonable when compared with data as discussed in step 11.

Detachable Multi-Part Electrode Assembly

Another element of our disclosure includes a selectively detachable multi-part electrode assembly. In one type of embodiment of our disclosure, the electrode assembly contains at least two parts, the electrode device which contains electrodes that make skin contact and the connections between electrodes and the measurement system, which can be a wired connections, a wireless connection, a multiplexed connection, some combination of these techniques, or other methods to transmit the electrical signal from the electrodes to the electronics. An embodiment of our disclosure has an electrode assembly in which these two parts are separate and separable. In other embodiments, they may be integral. The electrode device can, for example, be disposable and intended for single use by the patient. In such embodiments, the electrical connections would be intended for multiple use, however. An example of a method for reliable contact is metallic male/female contacts which mate with each other or contacts which are flat or otherwise shaped and provide intimate ohmic contact can be used. For electrical contacts which do not provide a mechanism for physically (mechanically) connecting the electrode device and measurement apparatus, a separate mechanical connection can be used. If a separate mechanical connection is applied, an embodiment of our disclosure has these two parts detachable and easily assembled and disassembled by the practitioner while reliably being held together during use. Without intending to be limiting, one method of effecting this holding together can be magnets present in the electrical connection assembly, in the detachable electrode device or both. The magnets and/or posts and sockets or other parts of the device can be arranged in a pattern that guarantees that the electrode device can only be attached in a single (correct) orientation. Another method can be a precision press fit or snap fit of plastic or metal parts.

Verification that the Electrode Device is Proper and Approved for Use

In another element of our disclosure, there is verification that in the multi-part electrode assembly that the electrode device has been properly chosen and qualified and is approved for the intended use. In another element of our disclosure, there is determination if an unapproved or counterfeit electrode device is attached in the electrode assembly so that the EIM electronics can notify the practitioner of the unapproved electrode device and/or cause the EIM electronics to fail to operate and take data using the unapproved electrode device.

Without intending to be limiting, an exemplary method for creating this objective may include creating a circuit in the electrode device, a chip with a preset serial number, or other identifying designator. As part of the pretesting routine, the EIM electronics reads the identifier on this chip and verifies that the electrode device is authorized. Without intending to be limiting, methods to accomplish this verification can include, but not limited to, having the library of approved serial numbers stored on memory in the EIM electronics, having the approved identifiers created using a coding scheme which can be verified in the EIM electronics, and having the serial number and/or identifiers transmitted to a central location for remote verification prior to authorization to proceed with the test.

Another embodiment of the disclosure would have verification of the serial number achieved by access through an online database to which the EIM electronics and computing device is connected. Upon usage, the EIM device would check out the serial number from the database for which use can be only one time. The database enforces this one time use by keeping track of serial numbers that are checked-out. This check in and check out procedure can occur in batches in which batches of serial numbers are checked out, in which case the EIM device ensures one time use.

Verification that the Electrode Device is Used Only a Single Time

Another element of our disclosure has verification that if the electrode device is intended as a single use device, it is indeed used only a single time and the attempt is not made to use it multiple times. this will avoid contamination, questionable electrical connections, etc.

There are several methods which can be used to so verify that the device is only used a single time. Without intending to be limiting, these methods may include one or more of the following steps:

1) Incorporating into the electrode device circuitry including a chip which can be written onto by the EIM electronics. When the test is performed, some message is written onto the chip preventing additional use. Conversely, some message might be erased which would prevent additional use.

2) Incorporating into the electrode device a fragile part of plastic, paper or other material designed to break upon insertion or removal. This part will be essential to performing the test so that the attempted use of the electrode device not including this part would be unsuccessful.

3) Incorporating into the electrode device a component which must be exposed to air for the device to operate. This can be some electronic component or could be a component or label displaying the serial number. The component has a limited lifetime exposed to air and changes in some way. Without intending to be limiting, this can include changing its electronic function to indicate that the lifetime in air has been exceeded or else eliminating or changing the serial number so that it no longer displays an authorized serial number.

4) If the remote verification method is used for the electrode device, as outlined above, storing the identifiers for electrodes which are authorized for use and denying authorization for additional use. Alternately, storing the identifiers of the electrode device which have been authorized for use and at chosen intervals, having the electronic device be required to communicate with a central location for verification of operation. At this time, new electrode devices used in this and other systems would be removed from the authorized list while new electrode devices would be added to the authorized list.

5) Another method for one-time use includes using the serial acquired from the disposable electrode assembly and upon first measurement, a timer can be electronically or digitally implemented so that the electrode may only be considered valid for a fixed amount of time.

Alternatively, the electrode can be limited to a fixed number of measurements.

6) Other methods can be used also.

Example 1—EIM Device for Simultaneous Inline and Orthogonal Measurements

We designed and built a configurable platform to automatically measure bioimpedance. The mechanical system used electromechanical actuators for constant electrode force over displacement, a high angular resolution stepper motor system to rotate electrodes, and a mounting system for easy reconfiguration of the electrodes. The electrodes in this prototype used drilled and tapped brass spheres, which were easy to machine and offered good chemical resistance to saline.

The electrodes were configured for simultaneous inline and orthogonal measurement configurations. However, any other suitable configuration may be used. The OTI measurement is an element of the disclosure for enhanced sensitivity to changes in anisotropy. This involves driving a current into the muscle fiber and measuring the consequent voltage non-colinearly. In one embodiment of the disclosure, the voltage is measured approximately parallel to the driving current. When this configuration of electrodes is aligned either along or across the muscle fiber axis, the resulting voltage is zero; however, at 45 degrees, the signal achieves a maximum and yields transfer impedance data that relates directly to anisotropy.

Example 2—Magnetic Linear Actuator

Figure 48:
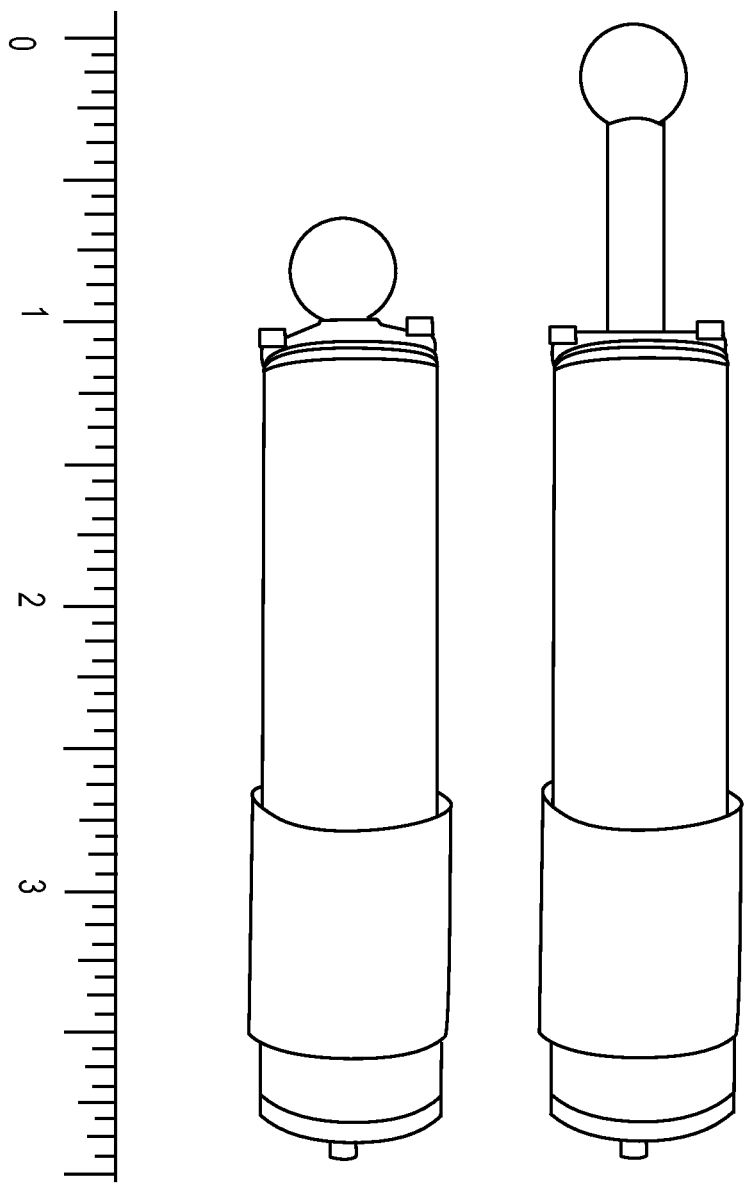
FIG. 48 shows a magnetic constant-force actuator fully retracted and extended.

We also designed and constructed a magnetic linear actuator. Unlike a spring, the linear actuator provides a constant force through the specified displacement range proportional to the current applied. To drive the actuator, we designed and constructed a closed-loop constant current driver with response time approximately 1 ms to quickly retract or apply constant force with the electrode. The actuator (shown in FIG. 48) has high-field, cylindrical NdFeB permanent magnets along the axis connected to a shaft that carries the spherical electrodes. The shaft moves axially inside two counter-wound magnetic coils, encased in a high permeability, low carbon steel barrel to increase the force by closing the magnetic circuit. The shaft slides in a low-friction, Delrin bushing.

Example 3—EIM Device with Several Additional Embodiments

Figure 49:
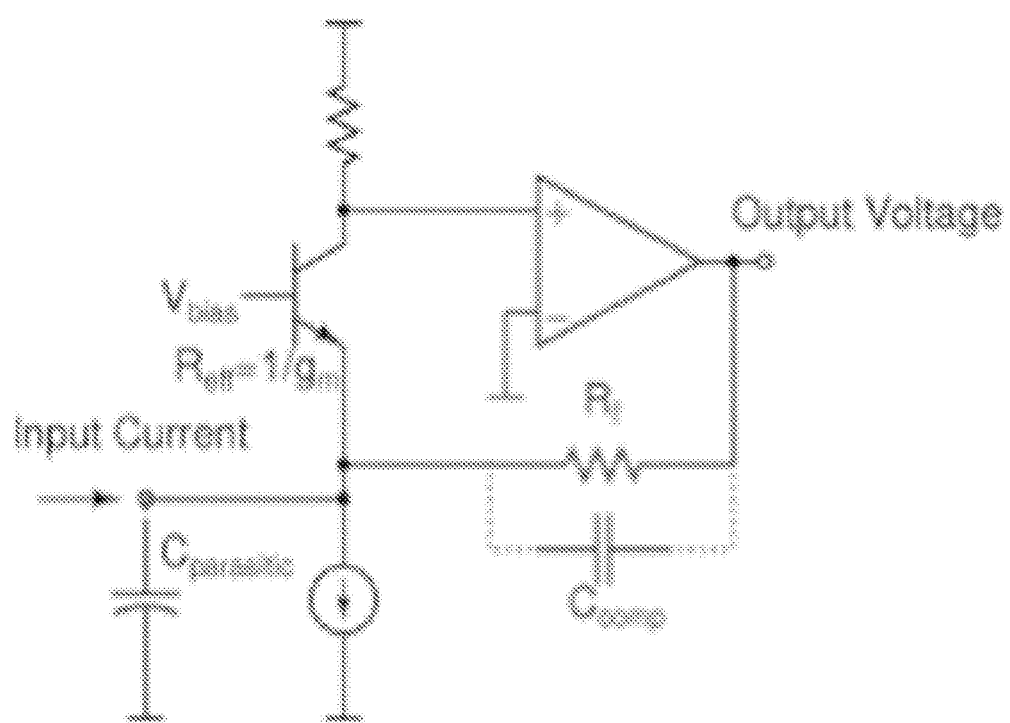
FIG. 49 is a circuit diagram of a transimpedance amplifier.

We designed, constructed, and demonstrated an electronic system with accuracy, speed, and frequency range that exceed current state of the art for bioimpedance, such as Impedimed's SFB7 used in an ongoing clinical trial. Several additional embodiments of the disclosure were used to overcome obstacles that typically limit both accuracy and bandwidth in bioimpedance systems. The first embodiment is use of low impedance voltage drive and then performing wide bandwidth current measurement at the low impedance sink. By driving tissue at low impedance, the effect of stray capacitances, which shunt current and cause errors in commonly used bioimpedance systems, becomes negligible. We overcame the challenge of performing a low-impedance and wide bandwidth, yet high accuracy current measurement by using our proprietary design for a transimpedance amplifier illustrated in FIG. 49.

The second embodiment is use of separate low-capacitance, high-bandwidth JFET differential amplifiers for each pair of voltage sensing electrodes to minimize parasitic capacitance. Previous instruments used electronic multiplexers at the sensing front-end that resulted in increased parasitic capacitance. By using separate amplifiers, the voltage measurement errors from combination of contact impedance and device input capacitance are minimized; these errors include voltage attenuation, as well as common-mode to differential mode voltage error from contact impedance mismatches.

A third embodiment is in the implementation of the lock-in amplifier. In contrast with typical lock-ins that use analog multipliers, we use high speed analog-to-digital converter to measure amplified signals directly, and then perform downconversion and subsequent signal processing fully digitally. This eliminates the effect of offset voltages, noise and distortion in comparison to using analog multipliers and filters before data conversion. The phase and magnitude errors from the anti-aliasing filters are minimized by simultaneously measuring voltage and current signals from twochannel, device-matched anti-aliasing filters and ADCs.

Example 4—Algorithms for Data Analysis

In one embodiment of the disclosure, we use Cole models for extracting and characterizing the electrophysiological properties of muscle. Cole models show, among other things, the behavior of electrical impedance of biological tissue and are typically used Cole models show the behavior of electrical impedance of biological tissue and are typically used to describe the relationship between frequency and complex impedance. The obtained model is not actual measured data but a curve fitted to the Cole equation containing four key parameters ($R_\infty$, $R_U$, $\alpha$, and $\tau$):

$$Z(\omega) = R_\infty + \frac{R_0 - R_\infty}{1 + (j\omega\tau)^\alpha}$$

where $Z(\omega)$ is complex impedance, $R_U$ is resistance at zero frequency, $R_\infty$ is resistance at infinite frequency, $\tau$ is the inverse of the characteristic frequency of the system, and $\alpha$ is a dimensionless exponent. The resulting complex impedance generated has a non-linear relationship with the independent angular frequency $\omega$ and in turn generates a semicircle with the imaginary center (negative reactance).

Algorithm Implementation: A challenge in fitting Cole models to bioimpedance data is that standard square-error minimization between the model and the data is non-convex. This means that we are only guaranteed to find locally optimal parameter values but not necessarily a globally-optimal value. This in turn implies that either (a) intensive computation is required to find (and verify) a globally-optimal solution with only some probability of success, or (b) if only locally-optimal values are found, the fitted model may not be consistent or not fit the data well, possibly decreasing the statistical significance of the resulting parameter values. An embodiment of the disclosure involves fitting Cole models based on two properties of the model: (a) it produces impedances that lie on a semi-circle (reported in the literature), and (b) the previously unknown and unexpected phenomenon that (b) three of the four Cole parameters are algebraically related to that semi-circle. Using these two properties allows us to reparameterize the problem into two sequential optimizations guaranteed to have a globally-optimal solution: (a) a constrained quadratic optimization that computes an optimal circle that fits the data followed by (b) and quasi-convex optimization that uses results of the first step to find the remaining parameter (which can be solved using any number of approaches, including gradient descent). Certain numeric conditioning can be used to improve accuracy of the results.

Another embodiment of the disclosure involves fitting a Cole model to data that is fit well by semi-ellipses (including ellipses with the major/minor axes aligned with the coordinate system). In this case, the ellipse is transformed into a circle, and the procedure above is repeated. The center of the ellipse is maintained as the center of the circle. In this case, properties of the major and minor radii (such as their ratio) can serve as a feature for data analysis.

Example 5—Tests on Anisotropic Substrates—Benchtop Impedance Network

We built an anisotropic impedance network with discrete resistors and capacitors, connected as a topological torus to eliminate boundary effects as is outlined above. Multiport impedances of this network were simulated in Simulation Program with Integrated Circuit Emphasis (SPICE) and compared with measurements using our system (the EIM1001, an embodiment of the disclosure designed and built according to FIGS. 1, 2, 3, 9, 10, 11, 12, 40, 41, 48 and 57) and a commercially available bioimpedance system (the ImpediMed SFB7). These tests were used to: 1) determine accuracy of the EIM1001 system; 2) compare sensitivity of the orthogonal configuration against the inline configuration; and 3) compare the EIM1001 with a commercial bioimpedance system (SFB7).

Figure 50:
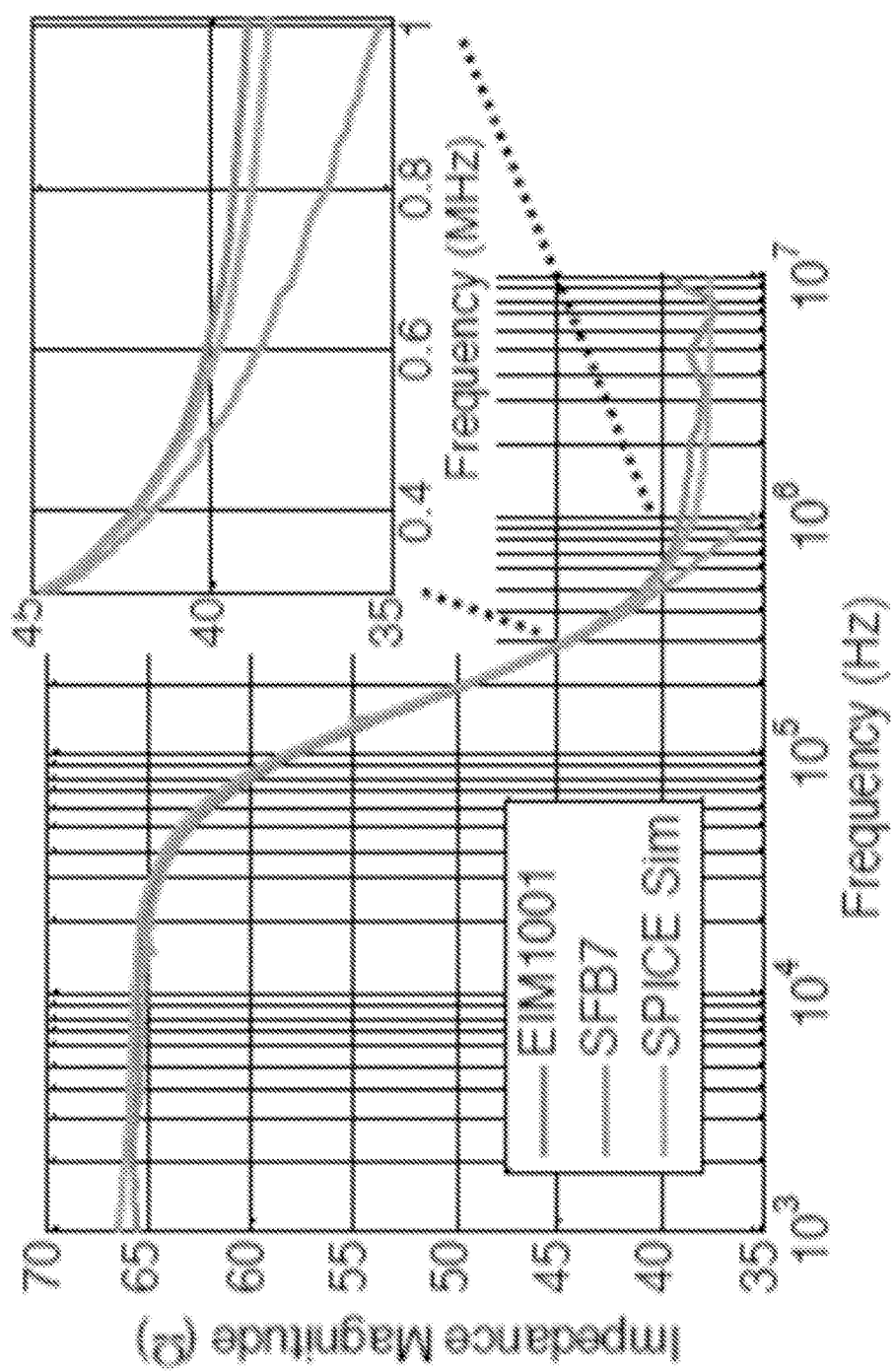
FIG. 50 is a chart shows a comparison of the EIM 1001 vs SFB7 against simulation of known impedance network.

Accuracy and Performance:

FIG. 50 illustrates measurements using our system EIM1001 and the SFB7 on a known impedance network and compares them with a SPICE simulation. The frequency range of the EIM1001 is 1 kHz-10 MHz, while SFB7 range is only 3 kHz-1 MHz. Both systems showed excellent agreement at lower frequencies when compared with the SPICE simulation. However, between 400 kHz and 1 MHz, the SFB7 shows significant measurement error while the EIM1001 maintains high fidelity. Even beyond 1 MHz, EIM1001 showed excellent agreement with simulations. Such improvements are very important given the prospect of important diagnostic information being provided by these higher frequency ranges. Multiple impedance network configurations were tested, and the EIM1001 consistently showed significantly better performance than the SFB7. Further, impedance amplitude and phase errors for the EIM1001 were always below 2% and 1° up to 1 MHz. Above 1 MHz, errors were below 4% and 2°.

Sensitivity:

Our experiments showing high fidelity between EIM1001 benchtop tests and SPICE simulations allowed us to confidently perform complex experiments in simulation. To compare sensitivity of orthogonal and inline measurements to changes in impedance values, the network used in FIG. 50 was simulated using different resistor values. We found that under some conditions orthogonal measurements were more sensitive to changes than classical in-line measurements. For example, changing one set of resistors by a factor of 2× resulted in a 51.7% change in orthogonal measurements, but only 38.5% in inline measurements. This indicates orthogonal measurements may be more sensitive to changes in muscle structure under some conditions and will likely yield clinically valuable information.

Example 6—Tests on Anisotropic Substrates—Biological Substrate

A series of meat experiments were conducted to determine: 1) angular resolution needed to quantify anisotropy; 2) frequency resolution needed to accurately characterize the impedance frequency response; 3) potential value of EIM data above 1 MHz; 4) effect of isotropic layers on measurements; and 5) effect of electrode force on measurements.

Figure 51:
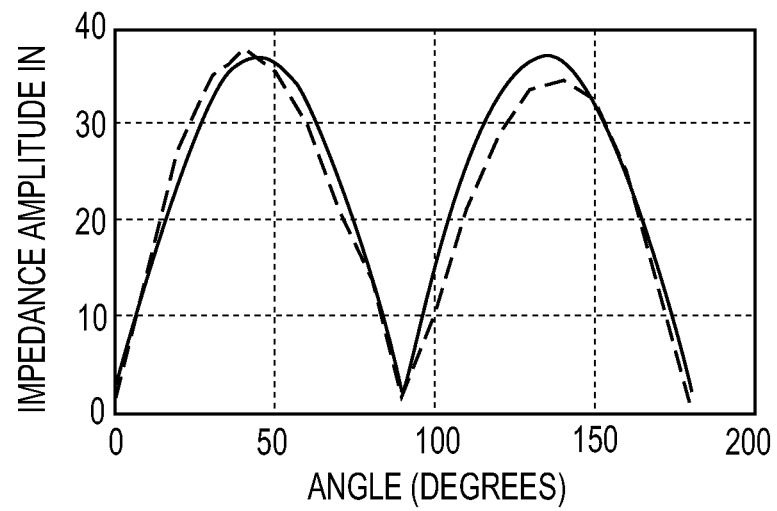
FIG. 51 is a chart showing Impedance amplitude over angle for the orthogonal configuration. Measured data is green. Sinusoidal fit is blue.
Figure 52:
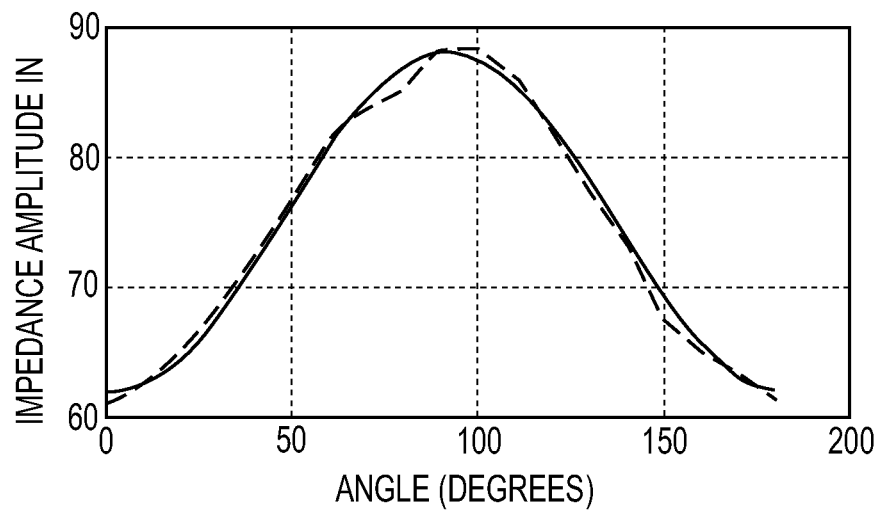
FIG. 52 is a chart showing Impedance amplitude over angle for the inline configuration. Measured data is green. Sine-squared fit is blue.

Angular Resolution: FIGS. 51 and 52 show measurements of fresh flank steak using both orthogonal and inline tetrapolar electrode geometries. Measurements were made at 50 kHz over angular range 0°-180° with resolution of 9°. The regularity of these results suggests a functional form for the measurement using parameterized fit. For example, for general anisotropic surfaces, including meat, a sinusoidal parameterization $\alpha|\sin[2(\theta-\varphi)]|+\beta$ fits very well for orthogonal measurements, with parameters $\alpha$ (amplitude), $\beta$ (offset), and $\varphi$ (phase shift). Similarly, a sine-squared parameterization fits inline well. In the figures, these fits are shown and have small error. Such parameterizations for tetrapolar measurements over angle are novel and have not been reported previously. They have a design consequence: only three samples from each of these curves are needed to fit each parameterization, and additional angular measurements simply improve fit via least-squares optimization.

Figure 53:
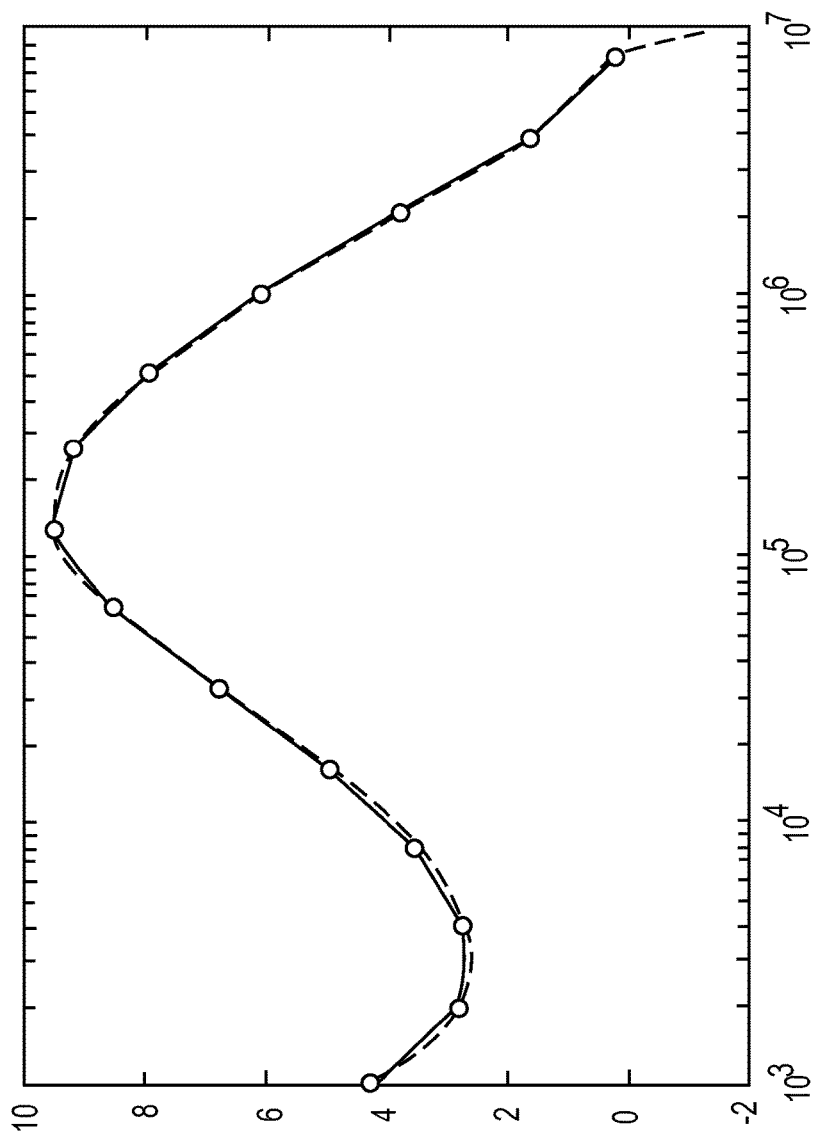
FIG. 53 is a chart showing one sampled phase response using only 3 points/decade and linear interpolation. Error between the oversampled (red, dashed) and downsampled response (black, solid) is negligible.
Figure 54:
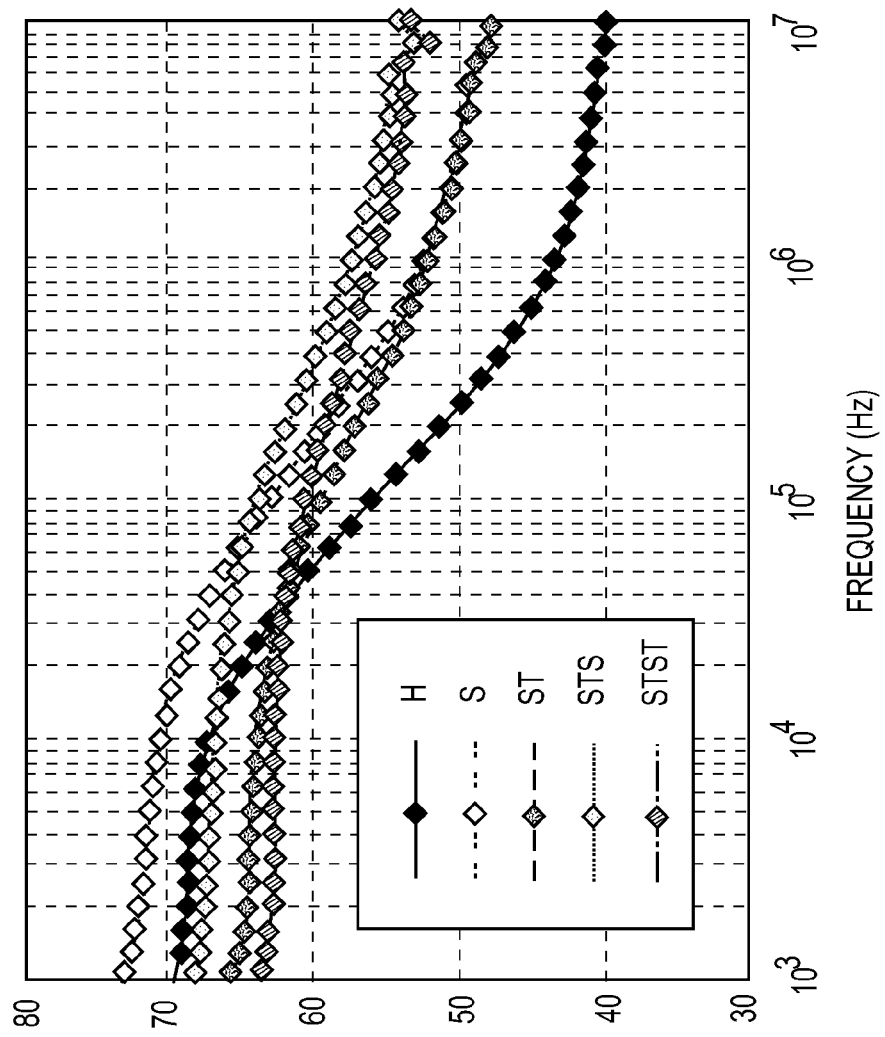
FIG. 54 is a chart showing impedance magnitude of a piece of meat (flank steak) after successive slicing and tenderization. H is the healthy response, S is response after slicing, ST after slicing and tenderizing, and so on. Points are measurements and the curves are interpolations.
Figure 55:
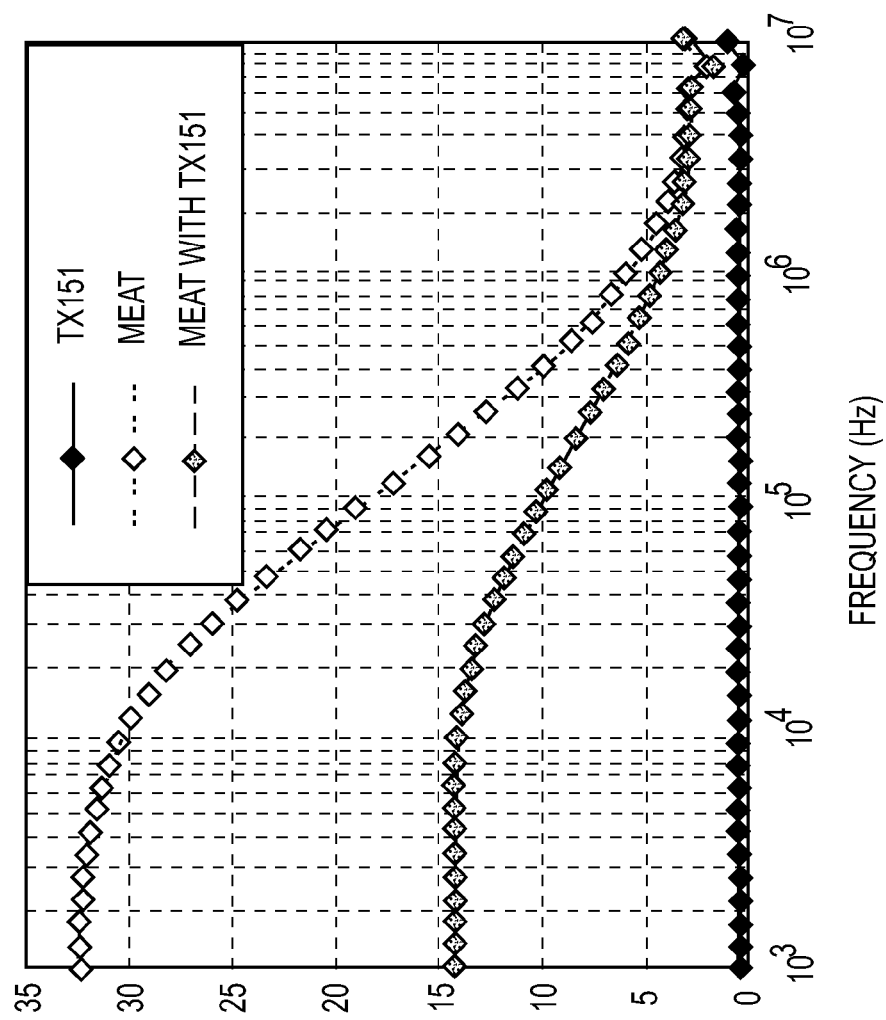
FIG. 55 is a chart showing impedance magnitude for orthogonal measurement at 50 kHz for TX151, bare meat and meat with TX151.

Frequency Resolution:

FIGS. 53-55 show several measurements on meat taken from approximately 1 kHz to approximately 10 MHz with 10 points/decade. The impedance spectra have no sharp resonances, meaning that frequency response does not change drastically over a small interval. As a result, we can use the Nyquist criterion to minimize the number of frequency sampling points required to recover the entire frequency response, with accuracy limited only by noise and signal size. Even simple linear interpolation yields accurate estimates of the meat's impedance response using only 3 points/decade (FIG. 53). Other embodiments can involve sampling 10 frequencies per decade at the expense of longer measurement time and reducing the number of frequencies over a given range to decrease measurement time and improve usability.

Ability to Detect Changes in Tissue Status:

To evaluate effects of change in muscle condition and size, meat was tenderized and sliced to assess the value of impedance information across the frequency spectrum. Although slicing and tenderizing are poor analogs for muscle atrophy and breakdown, tenderizing affects meat micro-structure while slicing affects its macro-geometry and neuromuscular diseases impact both micro- and macro-structures of muscle. FIG. 12 shows the effect of these manipulations on the meat's impedance structure. H is a fresh ("healthy") measurement, S is after slicing, ST is after then tenderizing, STS is a second slicing, etc.

FIG. 54, shows that tenderizing primarily flattens the spectrum over 1 kHz-10 MHz while slicing primarily shifts it. A result is that tenderizing had minimal effect at 10 MHz, and so measurement at 10 MHz (in this experiment) provides size information independent of tenderizing. The difference between 1 kHz and 10 MHz impedance magnitude (the "flatness") then yields information about tenderizing and anisotropy. This suggests that integration of low and high frequency information can help a practitioner determine how a patient's muscles are improving or degrading with treatment. Currently, no bioimpedance instrument measures accurately above 1 MHz while benchtop tests confirm the EIM1001 accuracy up to 10 MHz.

Impact of Isotropic Layers:

TX151 is a versatile isotropic gelling agent that we used as a phantom for skin. To understand the effect an isotropic layer like skin would have on measurements of muscle, we compared impedance of TX151 to bare meat and to meat with a thin top layer of TX151 (FIG. 55) which suggest that measurements through skin can yield meaningful measurements of muscle structure. The experiment shows that an isotropic layer can result in attenuation of orthogonal transfer impedance but there is limited distortion (FIG. 55). This measurement uses the "orthogonal" configuration which results in low transfer impedance values for isotropic material, explaining the small values for the TX151 measurement curve.

Electrode Force:

Experiments were conducted to determine the effects of applied electrode force on impedance measurements. A fresh piece of meat was tested with varying amounts of force (0.2-0.8 N) and data were compared. We found that impedance amplitude changes were less than 1 W over all frequencies and phase changes were less than 0.2°. The effects were much smaller than those caused by tenderizing or slicing, and indicate that it should be possible to determine muscle structure with non-constant force electrodes as long as the muscle's geometry is not significantly modified.

Example 7—EIM Device with Improved Capability

Figure 56:
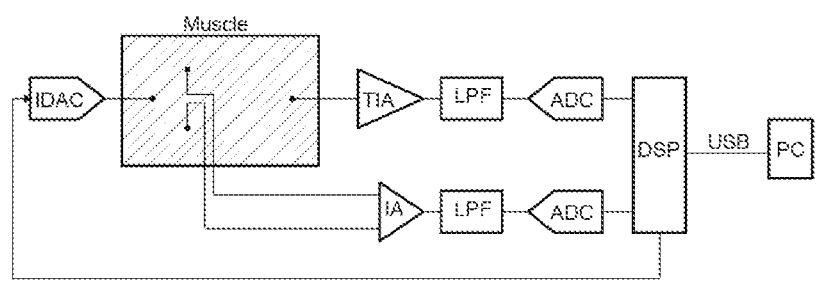
FIG. 56 is a simplified block diagram of the electronic system. The DSP interfaces with a PC through a USB cable.

The electronic system, summarized in FIG. 56, significantly outperforms existing state-of-the-art systems, with improved information under 1 MHz and new, never-before researched data over 1 MHz.

Example 8—Graphical User Interface (GUI)

Figure 57B:
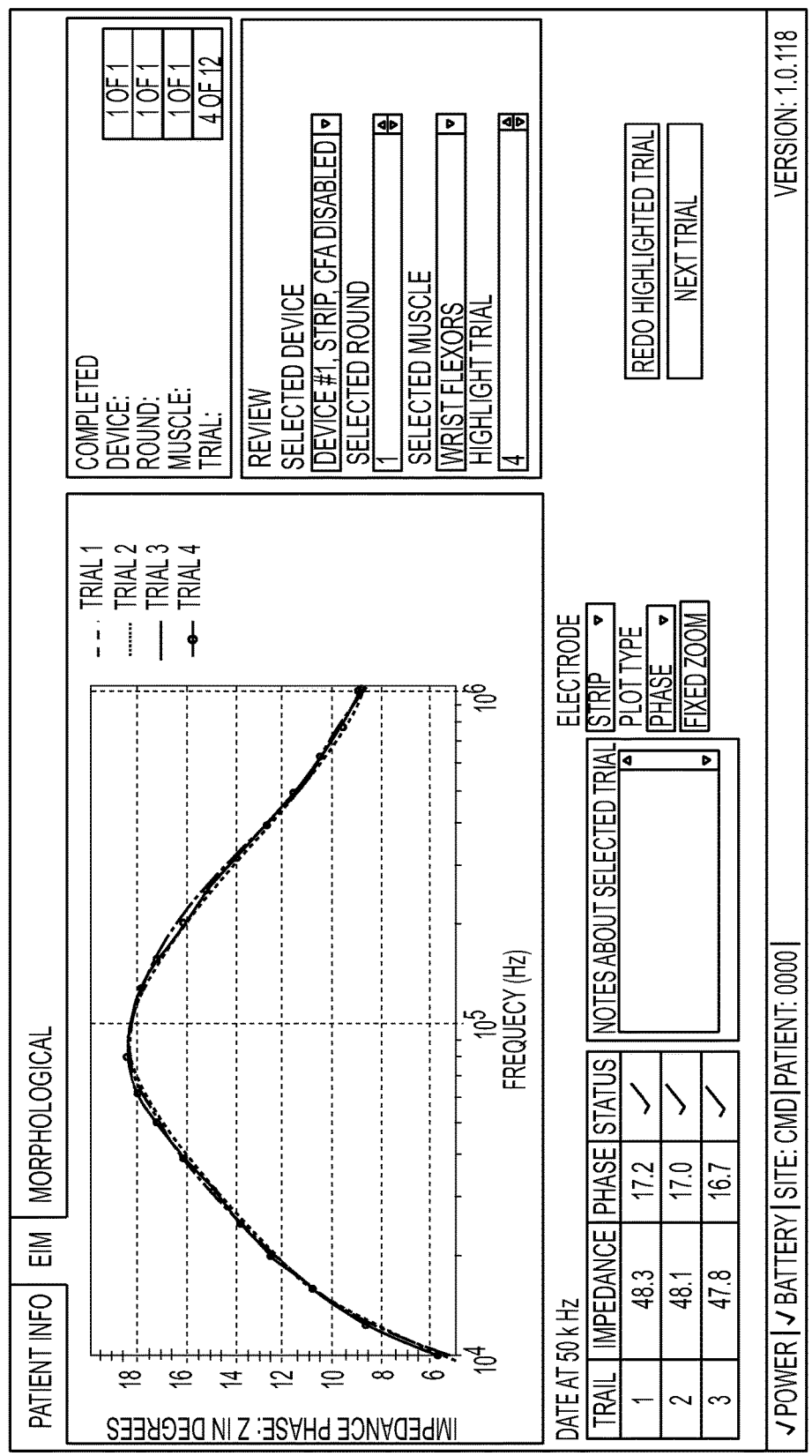
FIG. 57B shows the data display page showing four overlaid measurements. Data can be displayed by round, muscle, and trial. Also, simple error checking is conducted to ensure high quality data.

The GUI, an example of which is shown in FIG. 57, guides the operator through the procedure and displays data along the way. The startup page shown in FIG. 57A requests anonymous data for the patient and site including the patient number, gender, date of birth, etc. It also asks the operator to certify that certain steps outlined in the protocol have been taken prior to starting the exam. This helps ensure the protocol is followed carefully.

Example 9—Conformable Electrode Arrays

Figure 35C:
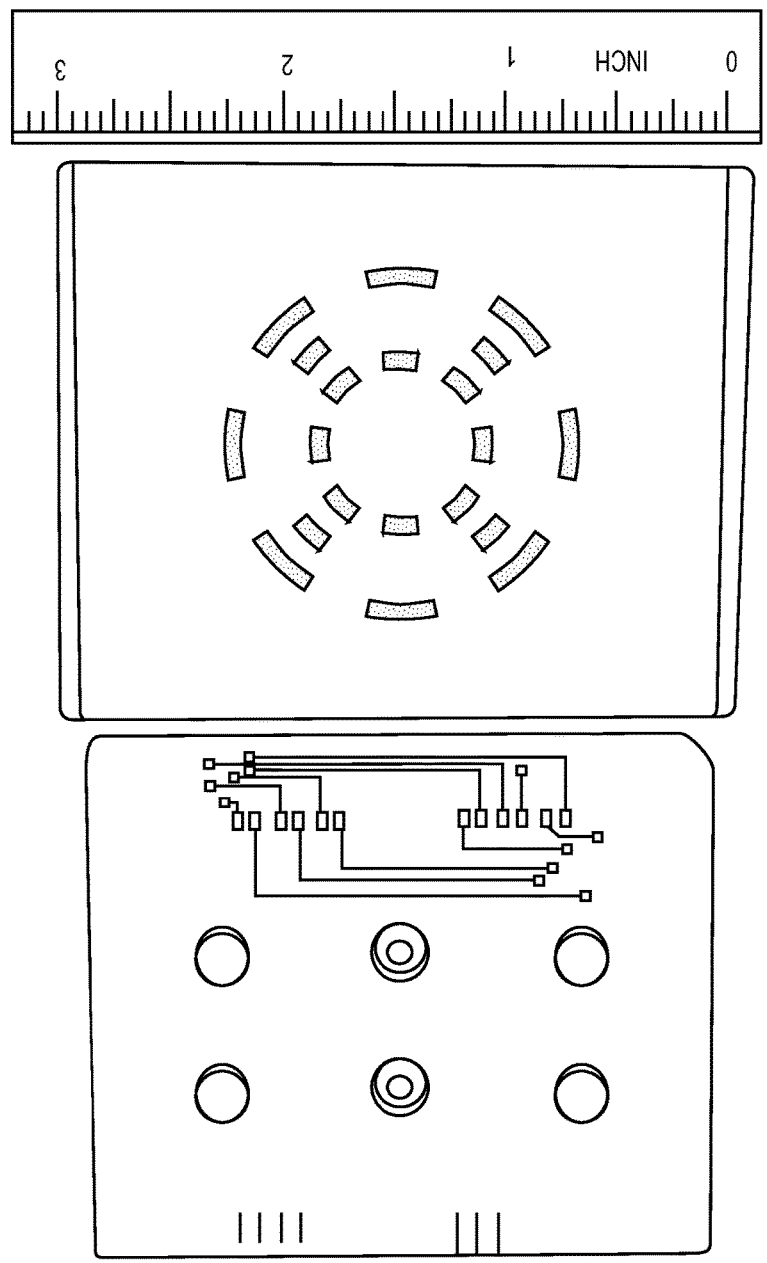
Figure 35D:
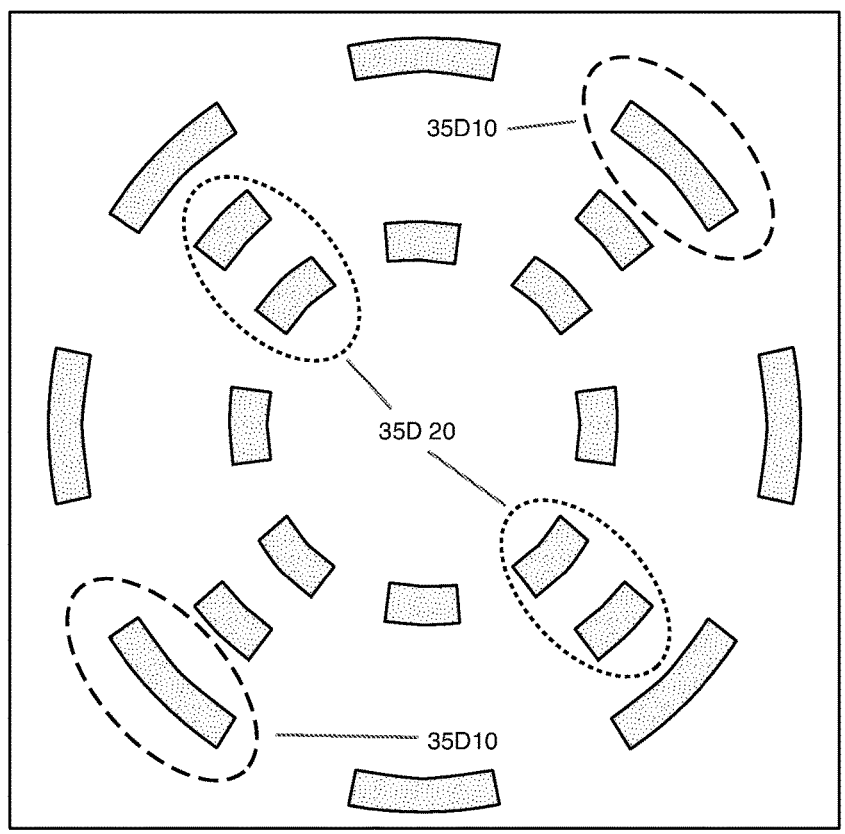
Figure 35E:
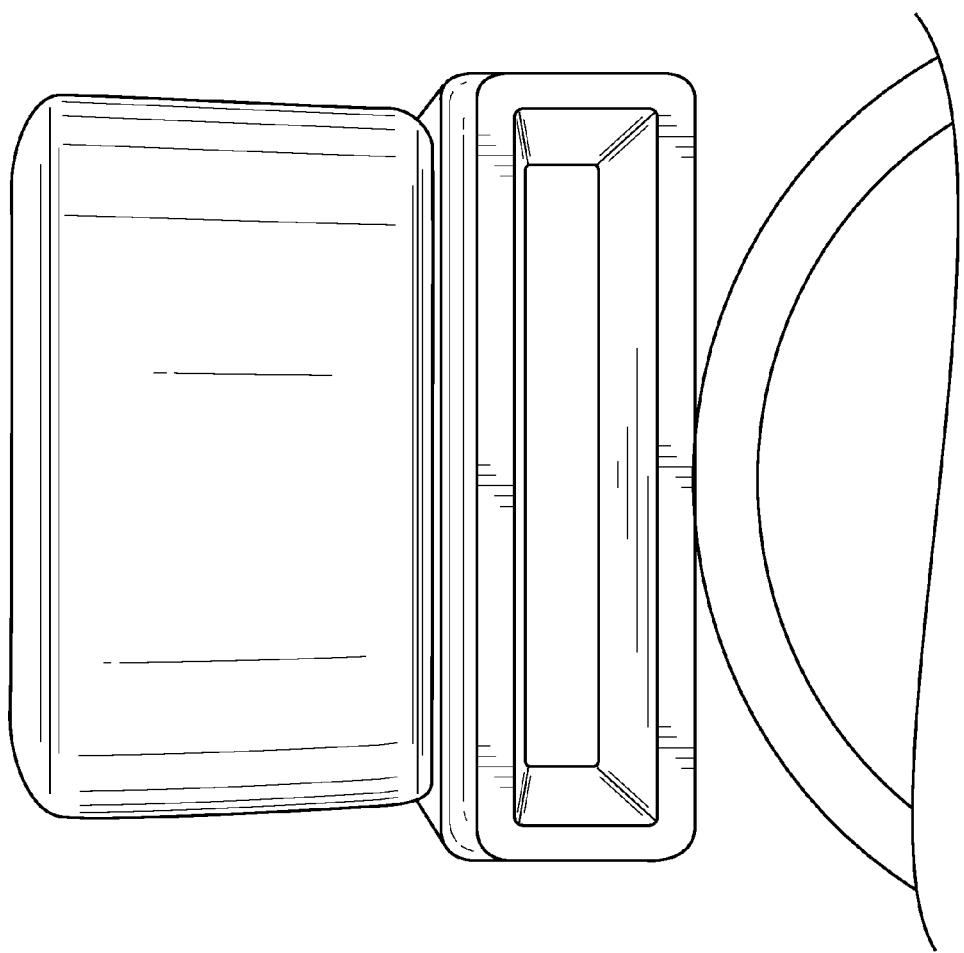
Figure 35F:
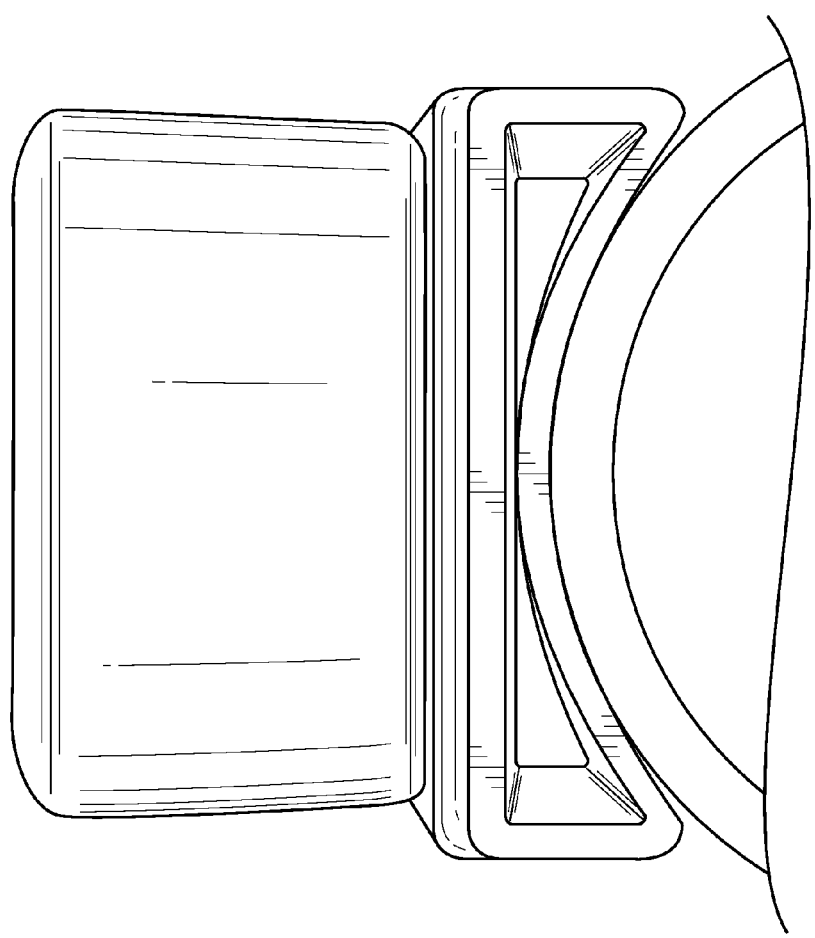

FIG. 35A shows one design of conformable electrode array. FIG. 35B shows the another design that we fabricated and tested. There are a number of embodiments of the disclosure. In one embodiment, a conformable, rubber-like base with hollow middle was designed such that the electrode array easily conforms to curved surfaces. The electrode arrays were then printed on thin PET (2 mils) and wrapped around the rubber base, adhering them using double-sided, pressure-sensitive adhesive (PSA). The electrodes were "printed" onto the PET material using a carbon-based conductive ink overlaid on silver-based conductive ink. This allows significantly less expensive manufacturing and greater flexibility with respect to electrode array design. In another embodiment, a novel connection mechanism was designed using magnets and pogo pins allowing the electrode array to easily "snap" onto the handheld device (see FIG. 58D). FIG. 35C shows the top and bottom of the assembled conformable electrode array. On the top side there are landing pads that connect the array to the handheld unit and metal disks that snap onto the magnets. On the bottom side are the printed electrodes. In another embodiment, an electrode array with 20 electrodes was designed that allowed both inline and orthogonal configurations at four different angles (0°, 45°, 90°, and 135°). FIG. 35D shows the electrode array. The electrodes circled in red and yellow represent one possible electrode configuration. Using multiplexers, a variety of other electrode configurations can be selected. FIG. 35E-F show how the electrode array conforms to a curved surface. Since EIM is usually performed on extremities (arms and legs) that have similar curvatures, this design offers excellent performance in that it ensures good contact between the electrodes and the skin.

Figure 58A:
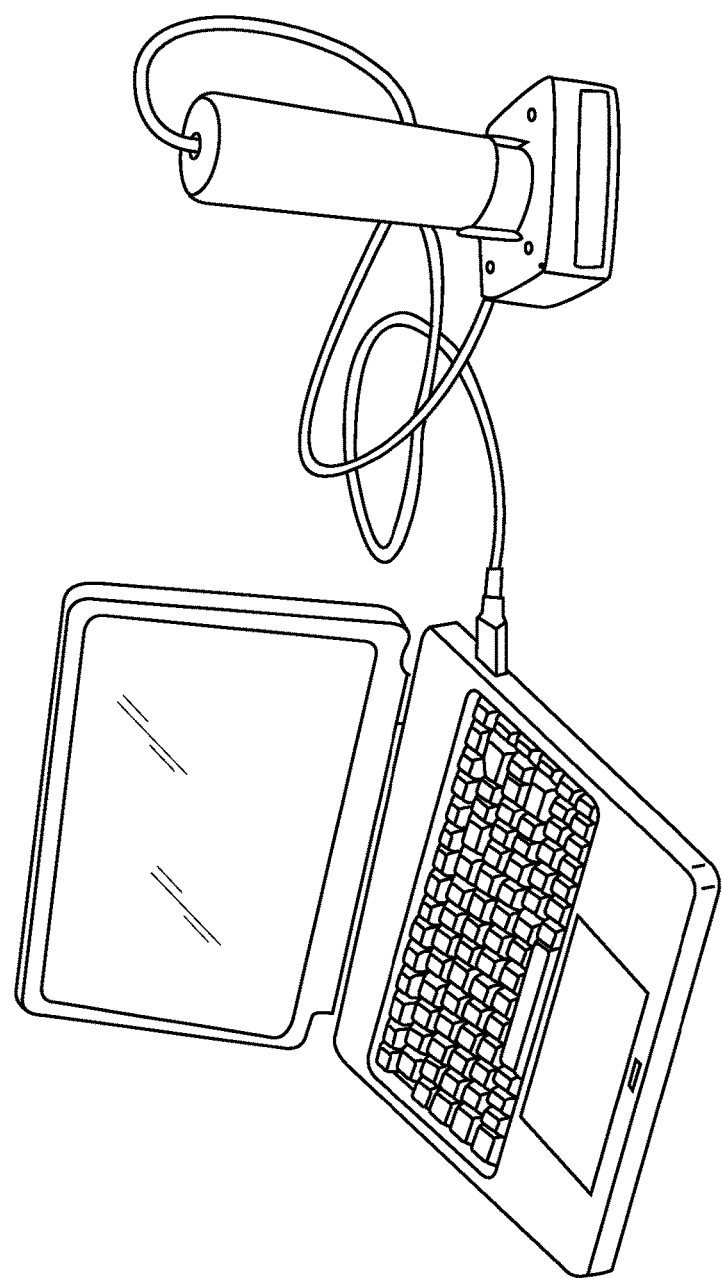
FIG. 58A shows the EIM1101 netbook and handheld probe. The probe is connected to the laptop through isolated USB.

In another embodiment, the housing for the device includes a constant-force actuator that uses a passive mechanical system with a constant-force mainspring connected to the top of actuator to extend it with constant force. FIG. 58A shows the full system including the handheld device and a small netbook computer.

FIG. 58B shows the inside of the handheld unit including the constant force actuation (CFA) spring. The actuator moves through a linear bearing preventing side motion and providing a low degree of friction (FIG. 58C). A simple plastic ring is included to fit the device and deactivate the constant-force actuator as needed.

Figure 58D:
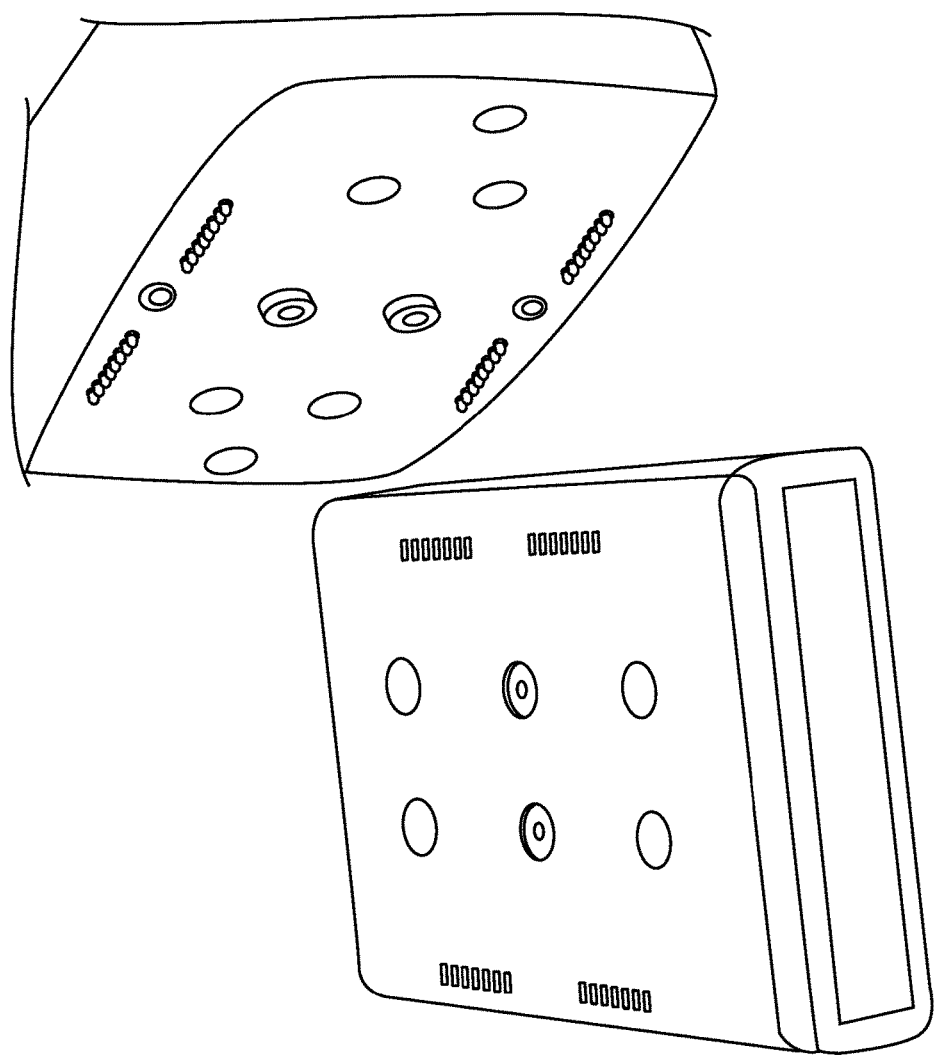
FIG. 58D shows the bottom side of handheld probe showing magnets used to hold the electrode array in place, the pogo pins used to make electrical connection to the electrode arrays, and an electrode array with metal disks that snap onto magnets.
Figure 59B:
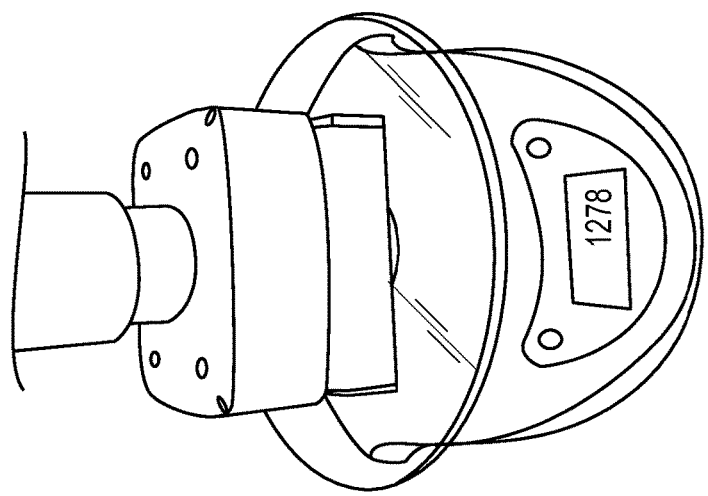
FIG. 59B shows some force applied, but not enough to cause displacement.
Figure 59A:
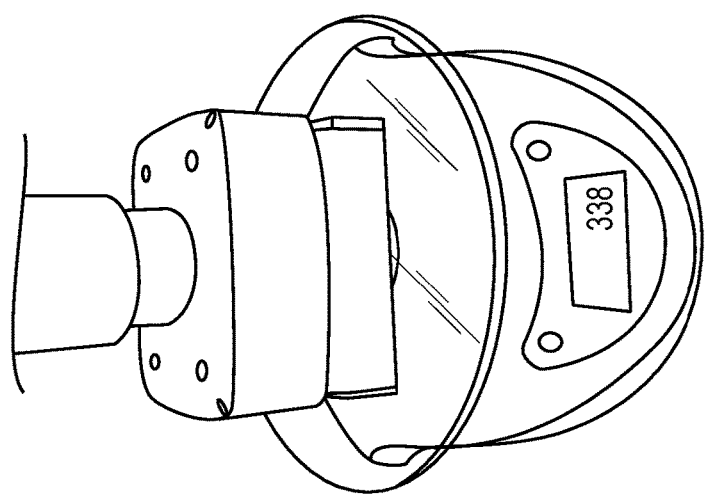
FIG. 59A shows no force applied.
Figure 59D:
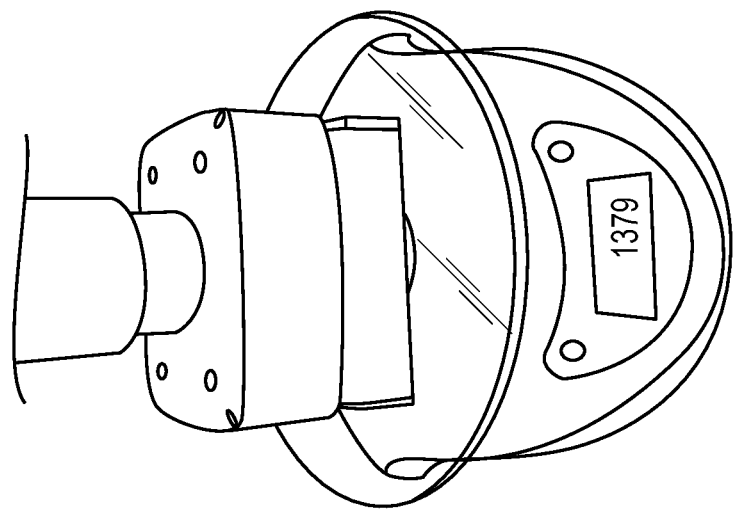
FIG. 59 C shows just enough force to cause displacement.
FIG. 59E shows nearly fully displaced. Note that in the range of displacement, the force is between 1319 grams and 1329 grams, a variation of only 0.75%.
Figure 59C:
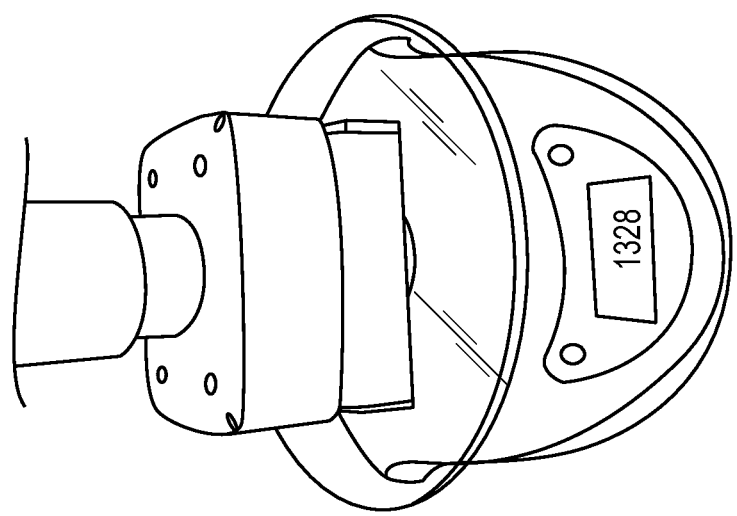
Figure 59E:
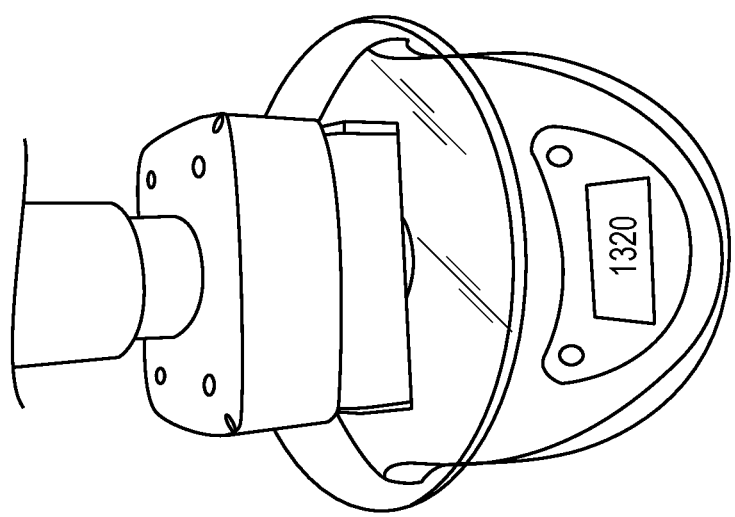

FIG. 58D shows the bottom of the housing which has two magnets and 24 pogo pins. The top of an electrode array is also shown. The electrode array snaps onto the handheld device and is held there by magnets. However, any suitable securing mechanism may be used. Pogo pins electrically connect the handheld unit to the electrode arrays by making contact with landing pads printed on top of the electrode array using silver-based conductive ink. This design makes it very quick and easy to replace the electrode array which will eventually be disposable.

Testing of Constant Force Actuator:

FIG. 59 shows the fully assembled handheld unit and electrode array placed on top of a scale. FIG. 59A shows that the weight of the device is 338 grams. FIG. 59B shows the handle when some force is applied, but not enough to cause the spring to begin to compress. In FIG. 59C, just enough force is applied for the spring to begin to compress. At that point, the handle moves downward and a force equivalent to 1328 grams is shown on the scale. As slightly more force is applied, the handle moves down some more (FIG. 59D), but approximately the same amount of force is applied to the scale (1319 grams). As the handle is pressed nearly to its range limit, FIG. 59E shows that the scale shows 1320 grams; almost exactly the same amount of equivalent force. This experiment, along with others, confirmed that the CFA worked excellently. Across a range of nearly 3 cm, the variation in applied force was less than 1%.

Example 10—Measurements with Human Subjects

We performed measurements on 5 ALS patients and 7 healthy subjects. This allowed us to test for repeatability performance, and also gain data on how well our device and algorithms could differentiate between healthy and sick subjects.

Figure 60A:
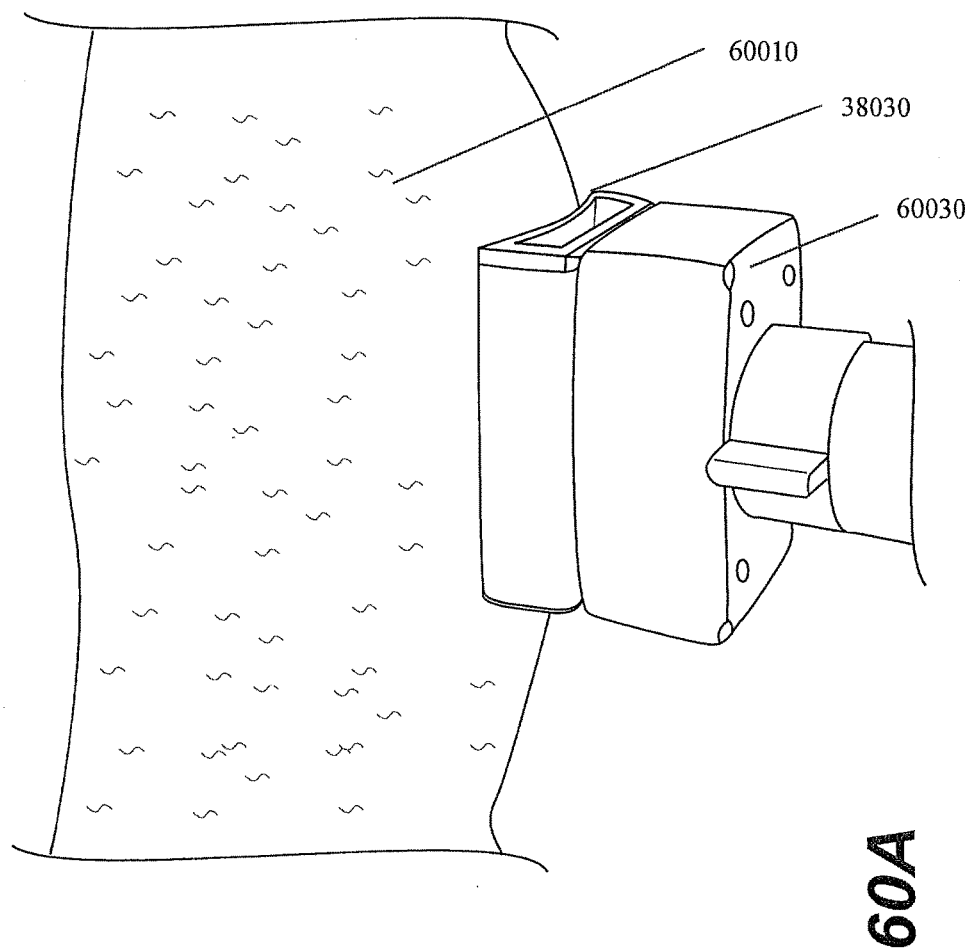
FIG. 60A shows the electrode array pressed against gastrocnemius muscle of healthy subject.
Figure 60B:
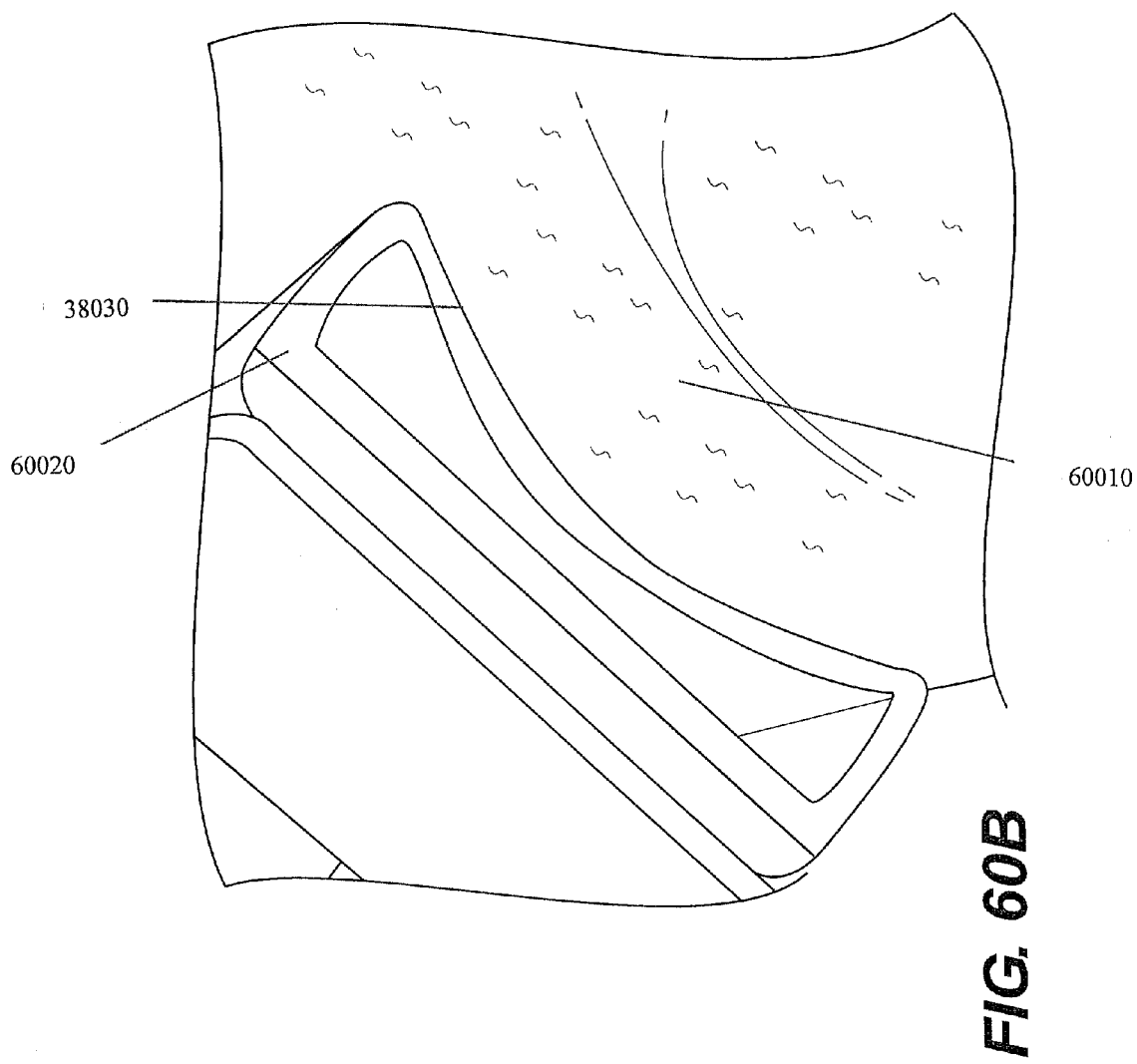
FIG. 60B is a zoomed in image showing electrode array pad conforming to a healthy subject's biceps.

Protocol:

The proposed protocol (15 repeated measurements on biceps) was performed on all healthy subjects. In addition, we collected data on 5 muscles (biceps, wrist flexors, quadriceps, tibialis anterior, and gastrocnemius) and repeated the full sweep of measurements a second time. For the ALS patients, two sets of measurements were also conducted (test-retest). However, the 15 repeated tests on biceps were not carried out since we found them to be time consuming and did not want to fatigue the patients. FIGS. 60A and 60B show the device 60030 with a holder 60020 supporting the flexible patch 38030 (see FIG. 38) pressed against the gastrocnemius and biceps 60010 of a healthy subject showing how well the electrode 38040 array (see FIG. 38) conformed to the curvature.

Figure 61:
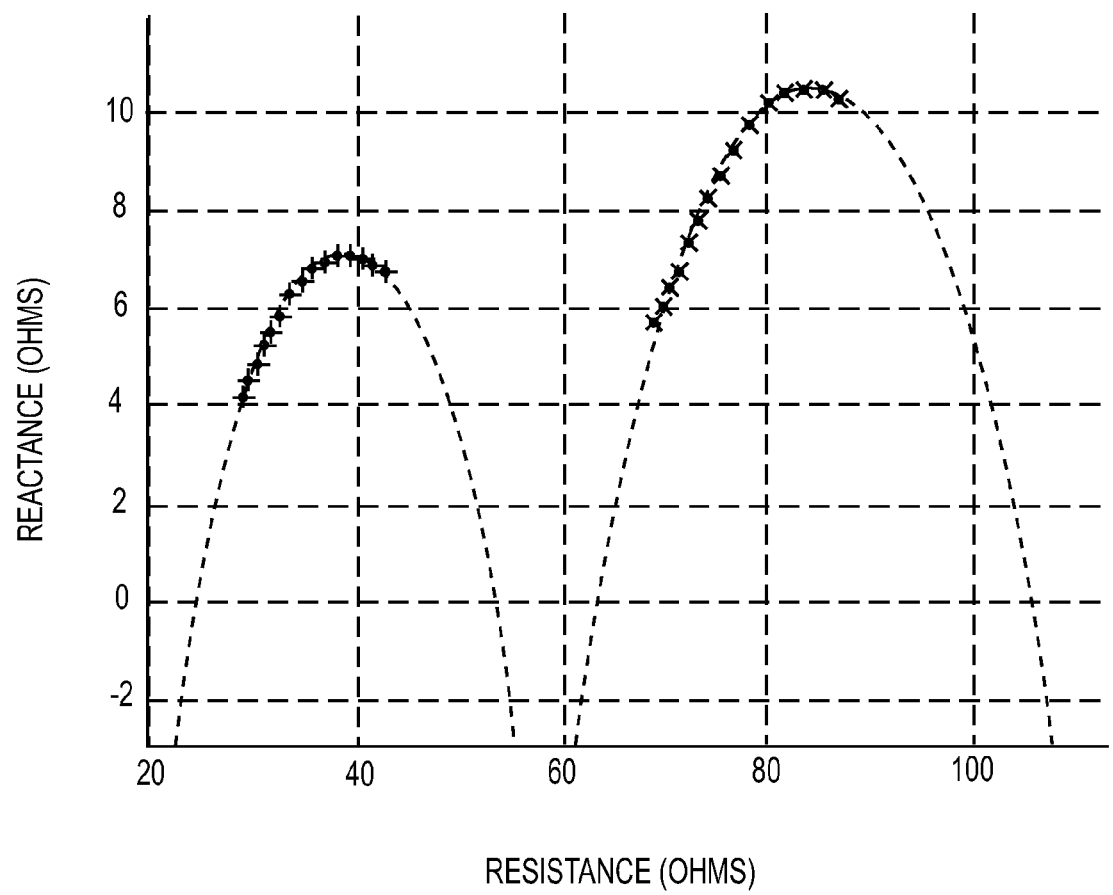
FIG. 61 is a graph showing Cole interpolation of data from muscles of healthy (blue, right) and ALS subjects (red, left).
Figure 62A:
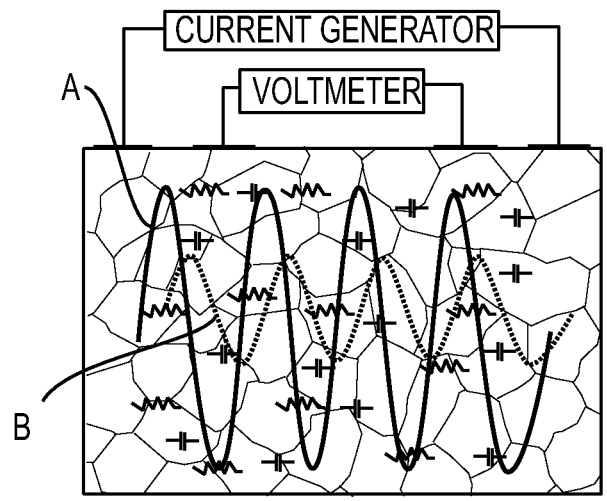
FIG. 62A shows EIM Measurements of healthy muscles.
Figure 62B:
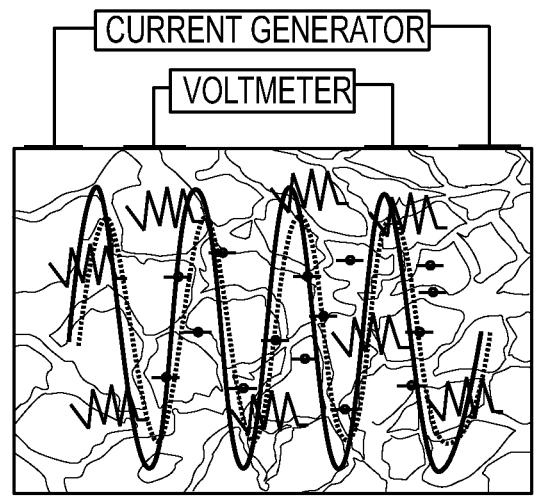
FIG. 62B shows EIM measurements of diseased muscles.
Figure 63:
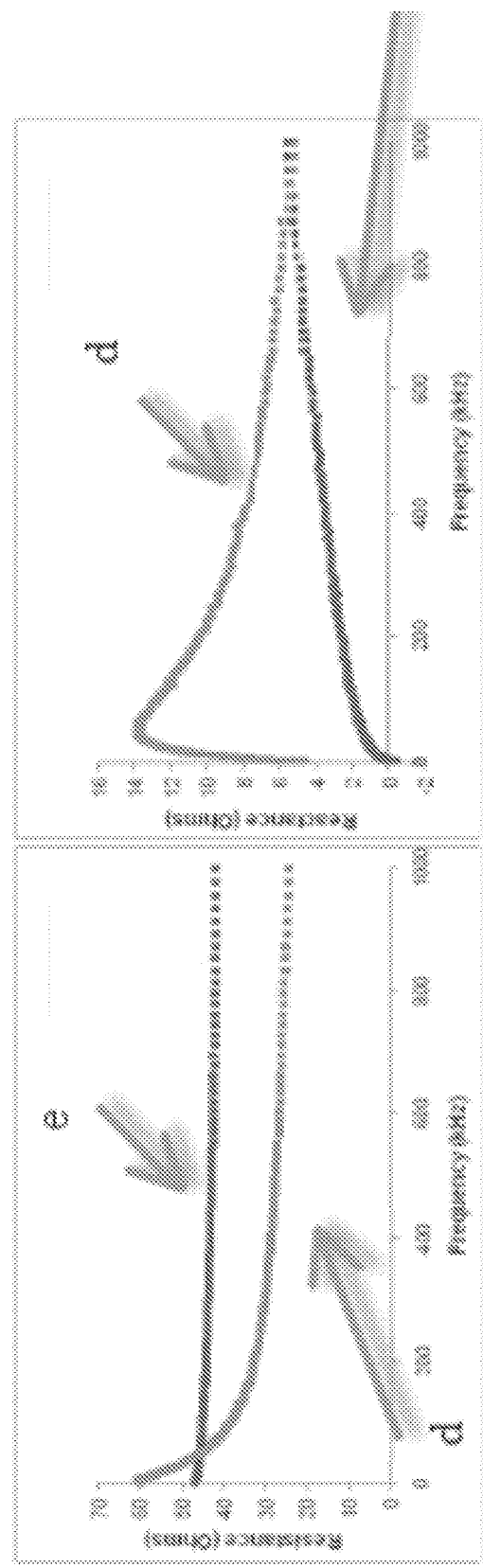
FIG. 63 is a graph showing frequency dependence of EIM Measurements of healthy and diseased (ALS) muscles.

Cole Mode Verification:

Cole models were applied directly to data obtained from healthy and ALS subjects. The Cole interpolation of a healthy (blue) and ALS (red) subject are shown in FIG. 61. The dotted gray line represents the ideal Cole output based on the Cole parameters outlined above, and the red and blue points represent the fitted data points. Evidently, the measured reactance and resistance (and thus, impedance) fits the Cole model with accuracy for both healthy and ALS subjects. Furthermore, there is a significant separation and difference in radii between the Cole interpolations of the healthy and ALS subjects allowing for easy discrimination between the two.

Repeatability Tests of Healthy Adult Subjects:

7 healthy subjects were recruited for the purpose of testing repeatability of the constant-force patch electrode and constant-force actuator. All of the patients signed informed consent forms and underwent multiple rounds of testing with the constant-force patch electrode, including rounds with the constant-force actuator enabled and the constant-force actuator disabled. Furthermore, measurements were also taken with a strip electrode array configuration in order to allow comparisons of repeatability between the multi-angle patch electrode and a strip electrode. It was found that the protocol having 15 repeated measurements was very cumbersome and time-consuming for both the nurse and the patient. As a result, near the end of the study, the protocol was modified to include only 5 repeated measurements. The repeated measurements were taken on the biceps. All subjects were contacted within two days of their visit and no subjects complained of any adverse effects.

Data Analysis:

Repeatability of phase, resistance and reactance at 50-kHz, 100-kHz and 150-kHz was analyzed through calculation of the intra-correlation coefficients.

Furthermore, the repeatability of the anisotropy of these parameters at the aforementioned frequencies was also calculated. Repeatability of the multi-angle electrode was also measured with and without the constant-force actuator enabled. Lastly, we looked at the repeatability of the multiangle electrodes in comparison with the strip electrodes. The results of these analyses are the following. The intra-class correlations for the 0 degrees and anisotropic measurements are shown are shown in Table 1. For all parameters, there was strong to nearly perfect agreement between the measurements. Furthermore, the degree of variation among the best three trials of any set of measurements was less than 8%. There was a high degree of repeatability in the measurements with the multi-angle constant-force patch electrode over a large frequency range (30-kHz to 3-MHz).

TABLE 1

Intra-class correlation coefficients for 0 degrees and anisotropic measurements of phase, resistance and reactance at 50-kHz and 100-kHz. All parameters showed strong agreement between the intra-class measurements.*

| Parameter | 1 cc-0° | ICC-Anisotron |
|---|---|---|
| 50-kHz Phase | 0.8321 | 0.9024 |
| 100-kHz Phase | 0.8677 | 0.8259 |
| 50-kHz Resistance | 0.993 | 0.8625 |
| 100-kHz Resistance | 0.994 | 0.9069 |
| 50-kHz Reactance | 0.7779 | 0.8644 |
| 100-kHz Reactance | 0.7138 | 0.6902 |

Example 10—Calculating the Semi-Ellipse

Any standard method of quadratic optimization can be used for solving for an ellipse that fits the data. The methods listed below are examples of how to solve for the parameters of the ellipse. In these cases, the ellipse is parameterized by the equation:

$$R^2 u_1 + X^2 u_2 + R u_3 + X u_4 = u_5 > 0$$

where R and X are resistance and reactance. Here, we list several methods of solving for u given measurements for R and X:

| Solution method | Details of solution method |
|---|---|
| $\min_{\|u\|_2=1} \| Mu \|_2$ | Minimizing u is the minimum singular vector of M. |
| $(M)_{i1} = R_i^2, (M)_{i2} = X_i^2$ | |
| $(M)_{i3} = R_i, (M)_{i4} = X_i, (M)_{i5} = 1$ | |

| Solution method | Details of solution method |
|---|---|
| $\min_u \| Mu \|_2$ <br><br> $(M)_{i1} = R_i^2, (M)_{i2} = X_i^2$ <br><br> $(M)_{i3} = R_i, (M)_{i4} = X_i, (M)_{i5} = 1$ <br><br> $u_1 = L$ | Requires solution of constrained quadratic optimization. First component of u (x-axis/resistance radius) is guaranteed to be positive for L > 0. Equality can also be made an inequality for same result. |
| $\min_u \| Mu \|_2$ <br><br> $(M)_{i1} = R_i^2, (M)_{i2} = X_i^2$ <br><br> $(M)_{i3} = R_i, (M)_{i4} = X_i, (M)_{i5} = 1$ <br><br> $u_1 = L_1, u_2 \geq L_2$ | Same as above but guarantees the second component of u (y-axis/resistance radius) is also positive if L2 > 0. |
| $\min_u \| Mu \|_2$ <br><br> $(M)_{i1} = R_i^2, (M)_{i2} = X_i^2$ <br><br> $(M)_{i3} = R_i, (M)_{i4} = X_i, (M)_{i5} = 1$ <br><br> $u_1 = L_1, u_2 = L_2$ | Same as above but fixes the aspect ratio of the ellipse (and can be fixed to a circle if L1 = L2). |
| $\min_u \| Mu \|_2$ <br><br> $(M)_{i1} = R_i^2, (M)_{i2} = X_i^2$ <br><br> $(M)_{i3} = R_i, (M)_{i4} = X_i, (M)_{i5} = 1$ <br><br> $u_1 = L_1, u_2 \geq L_2$ OR $u_2 = L_2$ <br><br> $u_3 < 0, u_4 > 0$ | Same as above but guarantees the center of the ellipse fitting the data has a positive resistance and a negative reactance. |

Since the Cole model lies along a circle with a center that has a positive resistance and a negative reactance, the final optimization with $L_1 = L_2 > 0$ and $u_2 = L_2$ is preferable and guarantees the fitting ellipse satisfies these properties, which the prior optimizations do not guarantee. Although a Cole model does not inherently fit an ellipse, we include a description of how to apply an elliptical fit because the aspect ratio of the ellipse provides an additional feature for neuromuscular disease analysis using EIM.

To convert these parameters to Cole parameters, we perform the following steps:

Determine the center (cx,cy) of the ellipse fitting the data, the x-axis radius r, and the aspect ratio k of the ellipse:

$$k = u_1/u_2$$

$$r = \sqrt{\frac{u_3^2 + u_4^2 k}{4u_1^2} - \frac{u_5}{u_1}}$$

$$c_x = \frac{-u_3}{2u_1}, c_y = \frac{-ku_4}{2u_1}$$

Solve for the Cole parameters (using an implicit conversion of the ellipse to a circle):

$$R_0 = \sqrt{r^2 - c_y^2/k} + c_x$$

$$R_\infty = c_x - \sqrt{r^2 - c_y^2/k}$$

$$\alpha = \frac{2}{\pi}\cos^{-1}\frac{1-\gamma^2}{1+\gamma^2}, \gamma = \frac{r - c_y/\sqrt{k}}{\sqrt{r^2 - c_y^2/k}}_a$$

Finally, with three of the four Cole parameters solved, we solve for the remaining parameter by solving a one-dimensional optimization. As such, a direct search for an optimal solution is feasible, and, further, experiments seem to indicate that the optimizations are quasi-convex optimization (simply meaning that there is only a single locally-optimal solution to the optimization):

| Optimization | Description |
|---|---|
| $\min_\tau \sum_i \| Z_\tau(\omega_i) - R_i - jX_i \|^2$ | Finds the parameters that minimize the normed error of the raw data versus the fitted data. |

-continued

| Optimization | Description |
| --- | --- |
| $\theta_i = \text{atan2}(R_i - c_x + jX_i - jc_y)$ | With respect to the center of the circle fitting the data, each data point has angle (between $-\pi$ and $\pi$). This minimizes the error in the angle of the actual data and the fitted data. This can also be modified so that the error in the angles does not suffer numeric inaccuracies due to the crossing thresholds at $-\pi$ and $\pi$. |
| $\phi_i(\tau) = \text{atan2}(Z_\tau(\omega_i) - c_x - jc_y)$ | |
| $\min_\tau \sum_i \| \theta_i - \phi_i(\tau) \|^2$ | |

Experiments have shown that the second optimization seems to yield more consistent solutions than the first.

FIG. 61 shows a plot of a Cole model fitting data. In this case, the negative reactance is plotted, which is consistent with neuromuscular EIM data, Listed in U.S. Pat. No. 9,113,808, which is incorporated herein in its entirety by reference, is the Matlab code for an example of the calculations we performed.

The following terms will be used in the following examples and in the claims: "base plate"—a plastic plate which becomes part of the disposable sensor. Flex circuit—a thin, flexible laminar structure which contains circuitry and becomes part of the disposable sensor. "foam substrate" or "foam block"—one or more sections of compressible polymeric foam which become part of the disposable sensor. "saline pouch"—a pouch made of plastic film or multilayer film containing saline solution. "gel block"—a block of gel which contains solution and releases it during system use. "disposable sensor"—a sensor for providing contact to the subject. It includes the base plate, the flex circuit and can contain the foam block, the saline pouch, the gel block and other components. "absorbent fluid reservoir"—a reservoir which holds saline fluid and applies it to the disposable sensor before use by the subject. "device"—rigid or semi-rigid part which is held by the user during use, contains electronics and connections, and is attached to the disposable sensor. "composite assembly"—the device plus the disposable sensor.

Example 11—Plastic Injection Molded Base Plate

A plastic injection molded base plate (1004 in FIG. 64) is used in the disposable sensor to provide a platform for assembly of the disposable itself, as well as a method for attachment to the handheld device. This injection molding provides all mounting features and is intended to be a low cost component in a high volume disposable, material volume is therefore kept to a minimum. This base plate is designed to maximize feature and structural integrity while reducing material volume and cost. While not intending to be limiting, the materials of choice for the base plate would include polycarbonate, ABS or polystyrene. The materials can be filled or reinforced. Other materials which might be used include nylon and moldable polyester. There may be an integrated clip which is designed to be functional without breaking as it should never reach its yield stress point during intended use conditions. (1012 in FIG. 65) The disposable sensor is affixed to the handheld measurement device via means of either the built in plastic clip that is part of the disposable, or alternatively/additionally via a magnetic clasp (magnets in the handheld device work with steel elements embedded into the disposable.) The disposable is 'keyed' to ensure it can only be affixed to the handheld in one correct orientation.

The overall perimeter size is 4 inches×3 inches with ⅛ inch nominal wall thickness. Recessed pockets are included in the design to allow the addition of ferrous and/or magnetized disks to enable or facilitate the magnetic catch feature. A recess at each electrical pin is included to allow the "petals" of the flex circuit to have a space to move. A vertical wall is incorporated to act as a registration guide for assembly of the flex circuit. Two or more circular registration bosses with appropriate lead-in chamfer edges are also included. These bosses mate with holes in the flex circuit to enhance alignment during assembly. Further, a recess is included to allow a single use digital chip to be included.

Example 12—Flex Circuit

Figure 64:
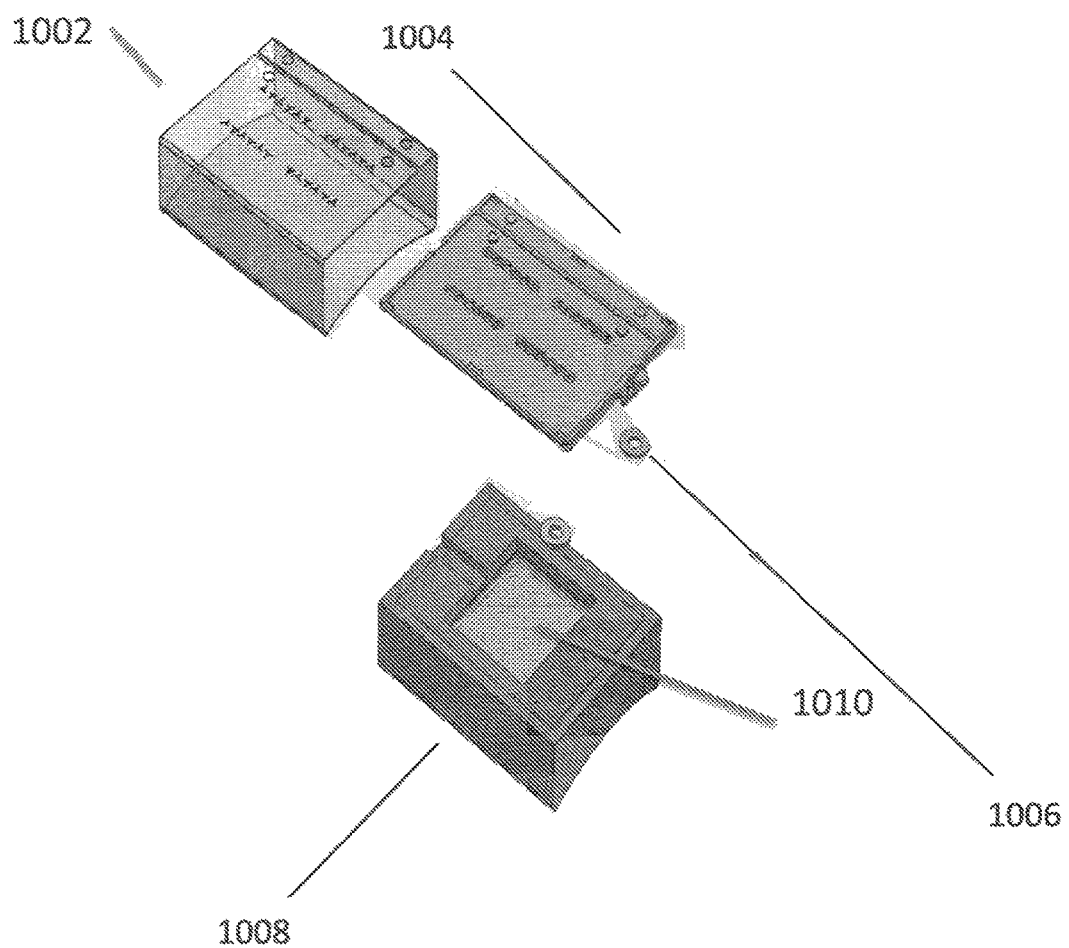
FIG. 64 shows an exploded view of the disposable sensor.
Figure 65:
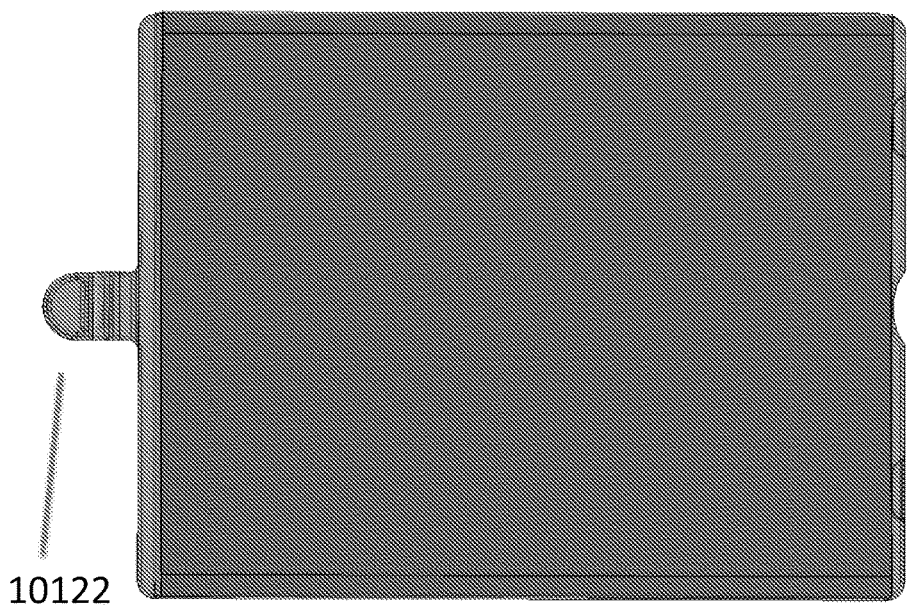
FIGS. 65, 66 and 67 show different views of the assembled disposable sensor.
Figure 66:
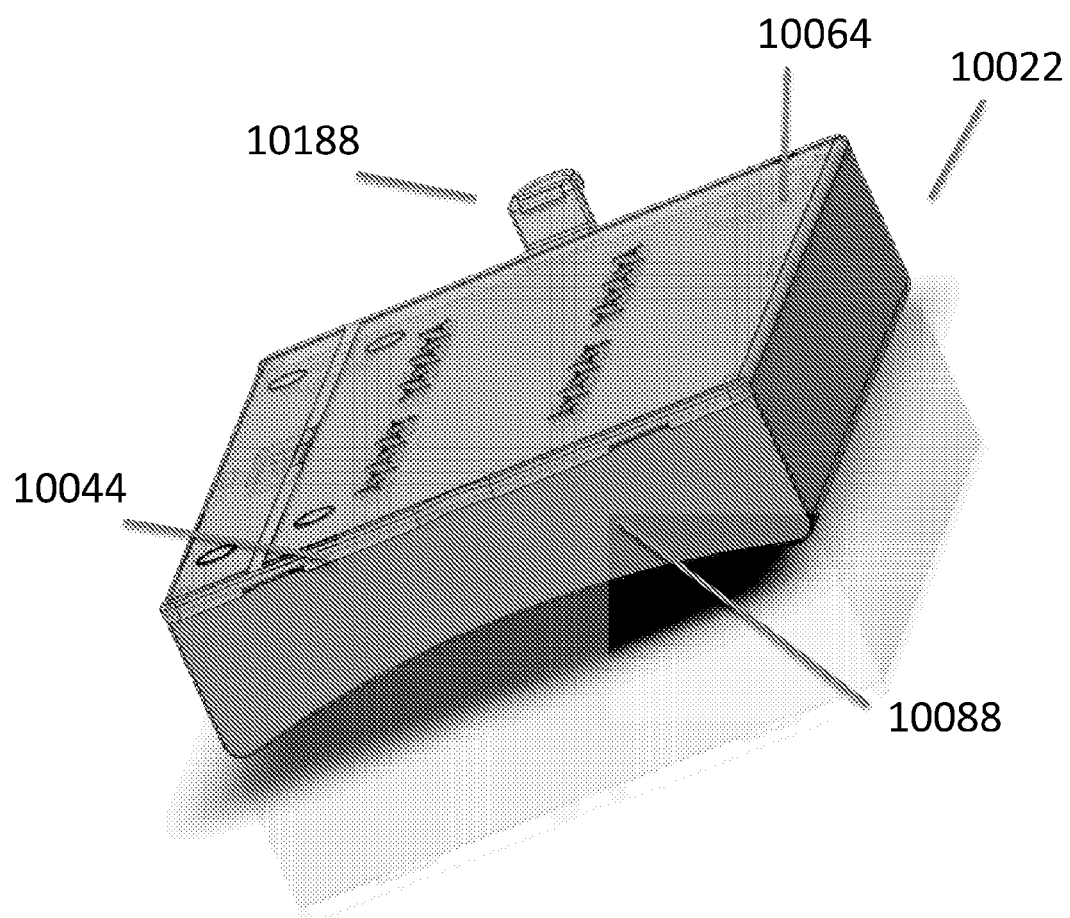
Figure 67:
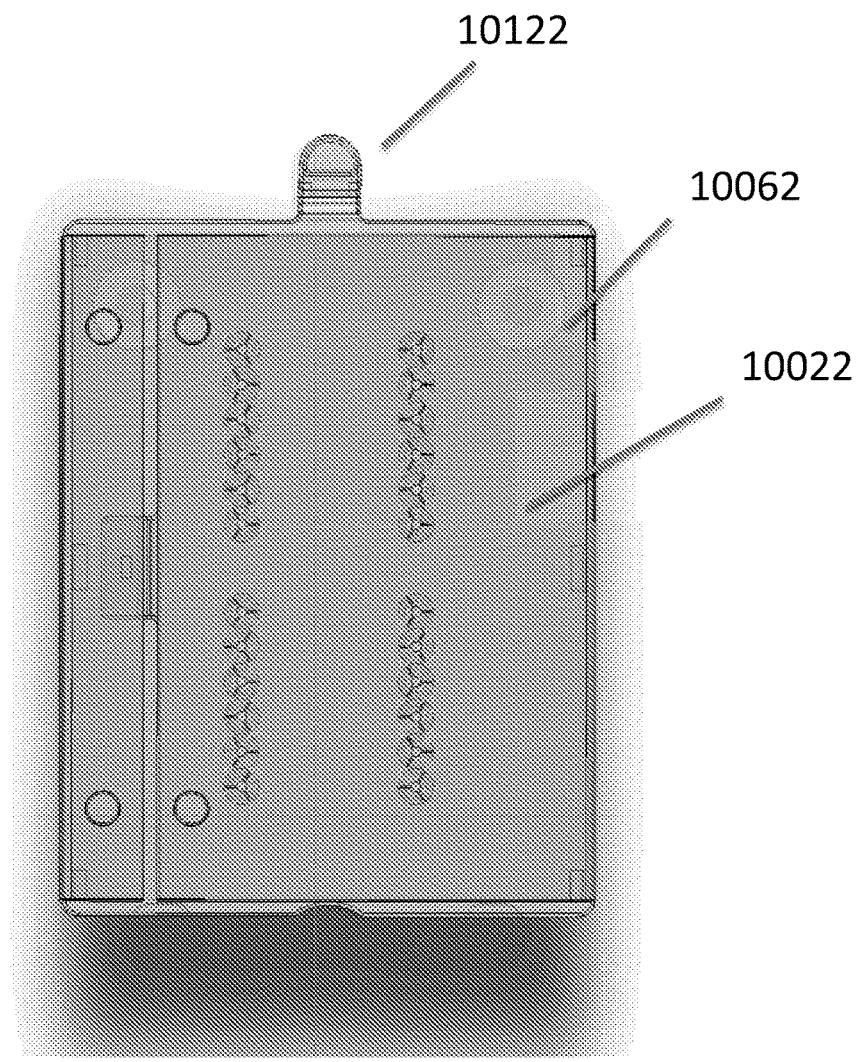

The construction of the disposable sensor is shown in FIGS. 64-69. The flex circuit is shown in FIG. 64, item 1002. It has a laminar construction using a carrier film. Without intending to be limiting, preferred films are polyester and polyimide although biaxially oriented polypropylene and other films might be used. Most preferred is 2 mil biaxially oriented PET film. In one embodiment, the contacts are printed on one side of the first film and the circuit on the other side of the film. Without intending to be limiting, preferred inks are silver and/or carbon ink although other conductive inks might be used. A small tab may be included on the flex circuit to provide a location to include an encodable chip for verification, single time use tracking and other purposes. A film with pressure sensitive adhesive on both sides is laminated onto the printed circuit side of the first film A protective layer remains bonded onto the other side of the pressure sensitive film until further processing.

Example 13—Foam Substrate

The foam substrate assembly (1008 in FIG. 64) has a number of different types of foam. Without intending to be limiting, one way to manufacture the foam sub assembly is from die cut elements. The foam type and durometer hardness can be varied depending upon the particular application of the sensor or body part being tested. In general, two types of foam are used, open cell and closed cell foams are used either to create a fluid barrier or fluid store. The foam substrate can have a recess or cutaway (1010 in FIG. 64) to permit insertion and retention of the saline pouch or gel block. Without intending to be limiting, the preferred foam is polyurethane, however, cellulose, EPDM, latex or other foams can be used.

Example 14—Saline Pouch

The saline pouch is manufactured from biaxially oriented polypropylene film. Without intending to be limiting, polyethylene film or polyester film can be used for the saline pouch. A multilayer film with or without an adhesive layer can be used for the saline pouch. The saline pouch is formed by joining the pieces of film by methods known in the art including heat sealing, ultrasonic sealing, vibration sealing or adhesive sealing. Preferred methods are heat sealing and ultrasonic sealing. The pouch is filled with an aqueous saline solution and sealed. The pouch can be manufactured in a manual process, semi-automated process or on a form-fill and seal machine.

Saline release is accomplished in one of 2 ways, A) The pouch is punctured via needle like features designed into the plastic base plate, and protected by a removable shield prior to use. Removal of the shield allows the spikes to puncture the pouch, or B) a 'tear off strip' is used whereby an orifice or series of orifices in the pouch are covered during manufacture with a plastic film strip. This strip has a tab which the user pulls to remove the tab, hence opening the pouch and allowing the saline to be ready to move from the pouch to the foam reservoir.

The saline solution is a 0.7 N solution of sodium chloride in water. Without intending to be limiting, a concentration range of 0.01 N to 5.0 N can be used and other salts like potassium chloride or mixtures of salts can be used. The pouch is intended to have a flat pillow like form that is then inserted into the foam substrate during assembly.

Example 15—Gel Block

Rather than the saline pouch, and in place or addition to the foam substrate, the disposable sensor can contain a gel block. This would be made from solid gel. By solid gel, we mean a gel material which is sufficiently crosslinked that when swollen with fluid retains a three dimensional shape and, while deformable and compressible, upon removal of any external force, returns to its original shape. The gel block is preferably a single unit or, alternately, a small number of units. Gel paste or small gel beads are not intended in our definition of gel block.

The gel block is manufactured from conductive ionic gel material or nonionic gel. Without intending to be limiting, partially or totally neutralized crosslinked polyacrylic acid, hydroxypropyl cellulose, hydroxypropylmethyl cellulose and hydroxypropyl starch may be preferred materials. Other solid gel materials could include polymethacrylic acid and other ionic polymers. Copolymers of these monomers are also contemplated. The gel solid can be swollen with water or with saline solution or with other ionic solution. The ionic gel can be manufactured using a method similar to that outlined in U.S. Pat. Nos. 5,221,722, 4,783,510 and 5,856,410, all of which are incorporated herein in their entirety by reference except that the crosslinker level is adjusted to meet the needs of the application and the reactive mixture is placed in a mold or other method to give a solid block rather than a dispersion.

Example 16—The Flex Circuit/Block Combination without Pouch

Figure 69:
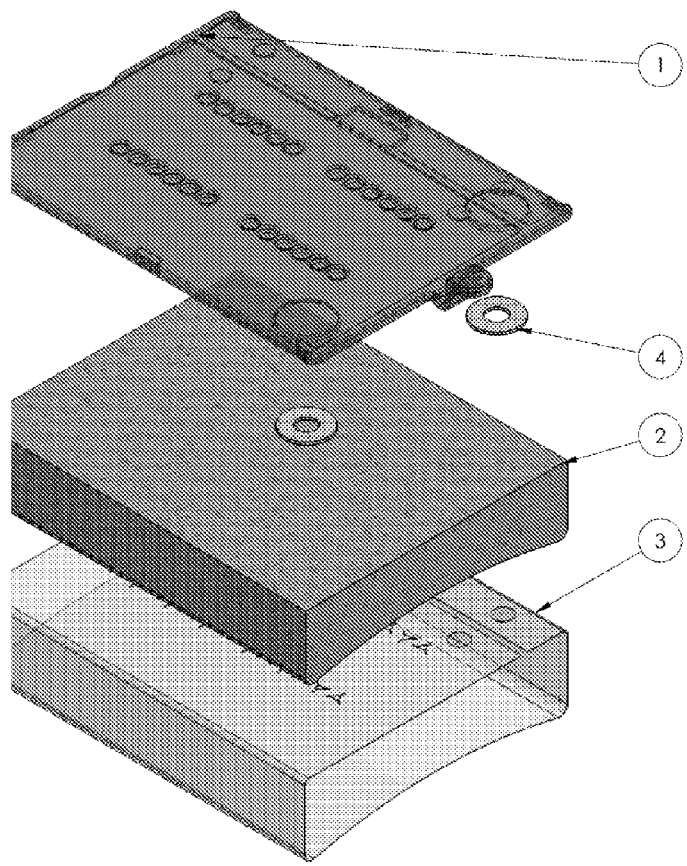
FIG. 69 shows an exploded view of the disposable sensor without saline pouch recess. Portions of the disposable sensor without saline pouch recess, at left, are not shown.

Without intending to be limiting, one design for the disposable sensor would have foam block or gel block from Examples 13 and 15 placed against the injection molded base plate from Example 11. The backing from the pressure sensitive adhesive layer of the flexible circuit of Example 12 may be removed and the flexible circuit wrapped around the foam block/molded base with the exposed pressure sensitive adhesive to the inside. The printed contacts which are applied to the patient are on the foam block side and the oval contacts are on the injection molded block side. An exploded view is shown in FIG. 69.

Example 17—The Flex Circuit/Block Combination with Pouch

Figure 68:
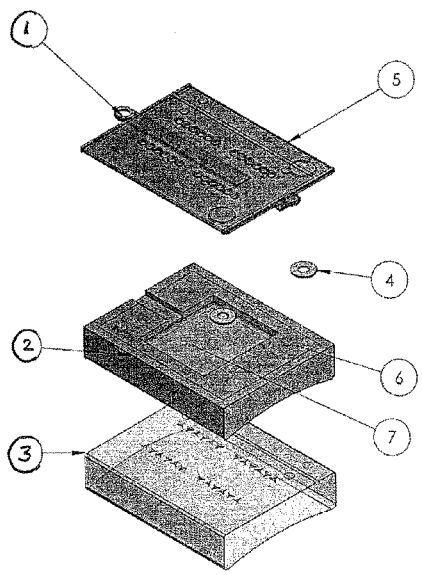
FIG. 68 shows another exploded view of the disposable sensor with saline pouch recess.

This design for the disposable sensor—flex circuit/block combination with pouch—is assembled in a manner similar to Example 16 except that the pouch of Example 13 or gel matrix of Example 15 is inserted into a recess in the foam block prior to assembly. Holes have been punched in the flex circuit during its manufacture or subsequent to its manufacture to allow release of the conductive fluid. An exploded view is shown in FIG. 68.

Example 18—Absorbent Fluid Reservoir

The absorbent fluid is a tray or dish which contains an absorbent block or blocks. The absorbent block or blocks are infused with saline solution. In use, the assembled device is placed on the absorbent fluid reservoir after a measurement on a patient. This holds the device in a safe, non-contaminating way and also coats the sensor face with an appropriate quantity of saline solution. The device is then removed from the absorbent fluid reservoir, used to make another measurement on a patient and then returned to the absorbent fluid reservoir. Since, over time, the absorbent fluid reservoir can lose fluid and not provide sufficient saline for a measurement, the device and electronic circuitry can have capability to measure electronically the moisture level of the absorbent fluid reservoir and communicate (as with a green light or other signal) that the wetting is sufficient.

Example 19—Packaging the Absorbent Fluid Reservoir and the Disposable Sensor The absorbent fluid reservoir can come packaged with the disposable sensor inserted. The two items can be packaged in a moisture barrier pouch. The user would then open the pouch, attach the device to the disposable sensor remove the assembled device from the absorbent fluid reservoir for the first application to the patient. To avoid lack of sterility, cross-contamination, etc. it can be desirable to verify that the absorbent fluid reservoir is not being reused but is a single use, disposable item. This could be effected. by a molded piece which is broken off and gives an authorizing signal to the chip in the flex circuit, inclusion of an RFID chip in the absorbent fluid reservoir which would send a single use authorization to the device upon first use, or other method.

Example 20—Using the Composite Assembly

Example 20A with Neither Fluid Pouch or Absorbent Fluid Reservoir

Figure 70:
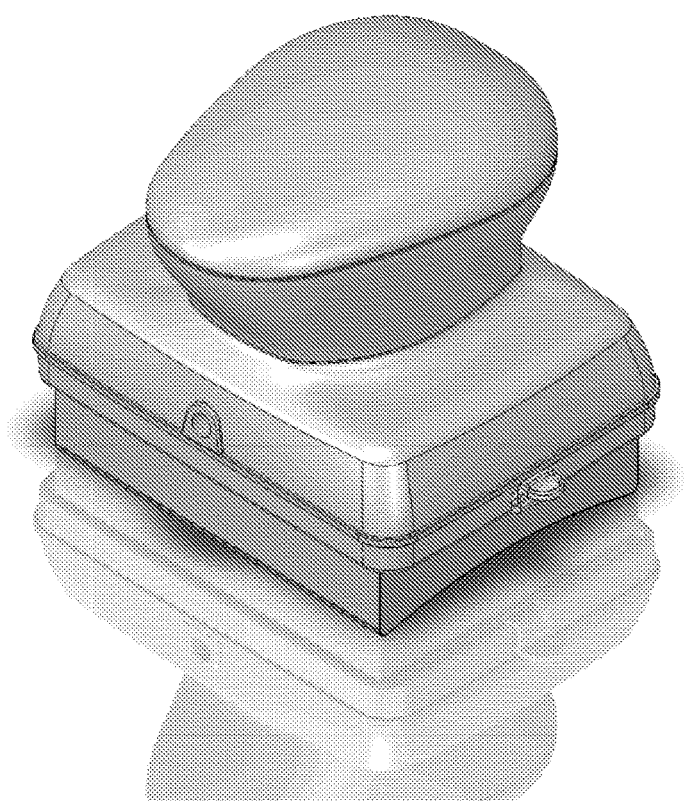
FIG. 70 shows the assembled device.
Figure 71:
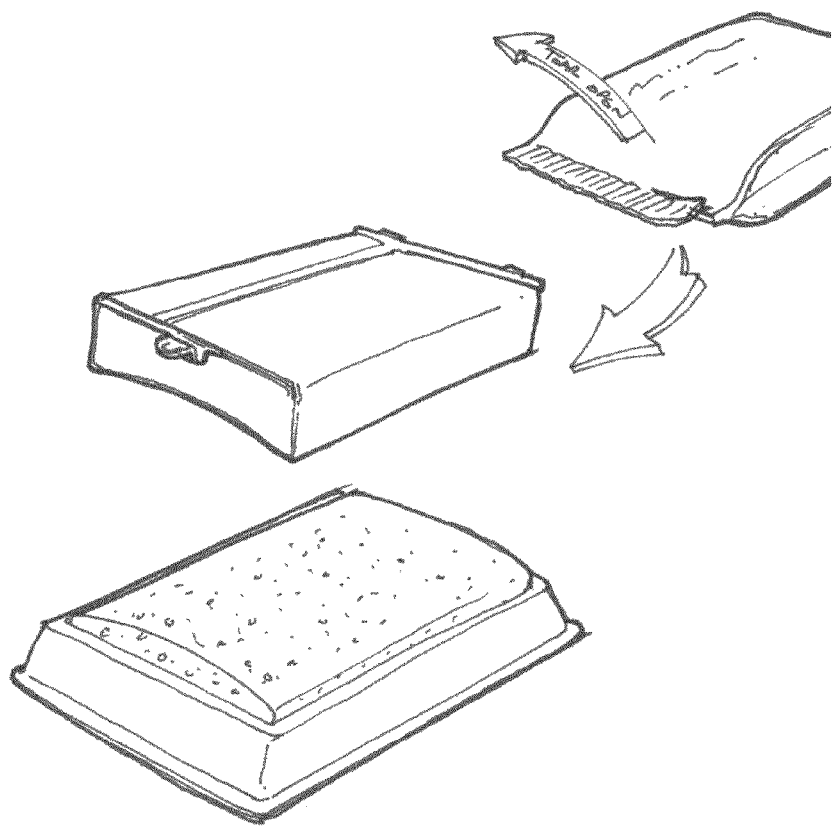
FIG. 71 shows the sensor, absorbent fluid reservoir and package. A portion of the package, at right, is not shown.
Figure 72:
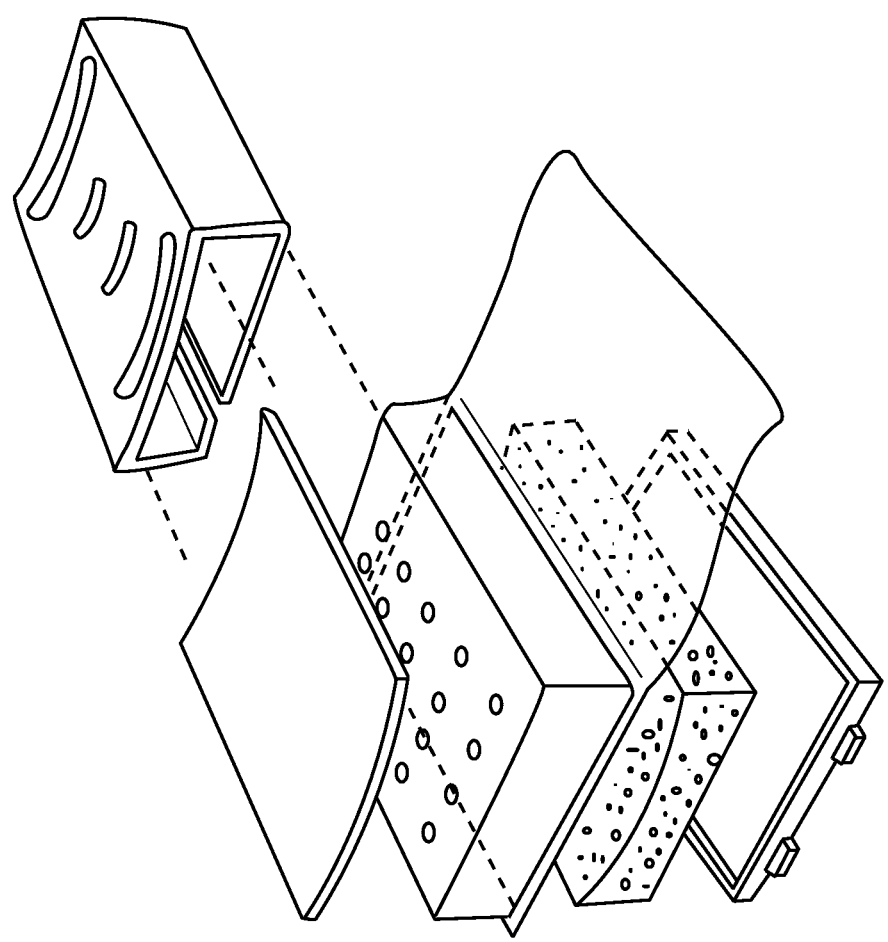
FIG. 72 shows an exploded view of the absorbent fluid reservoir and sensor.
Figure 73:
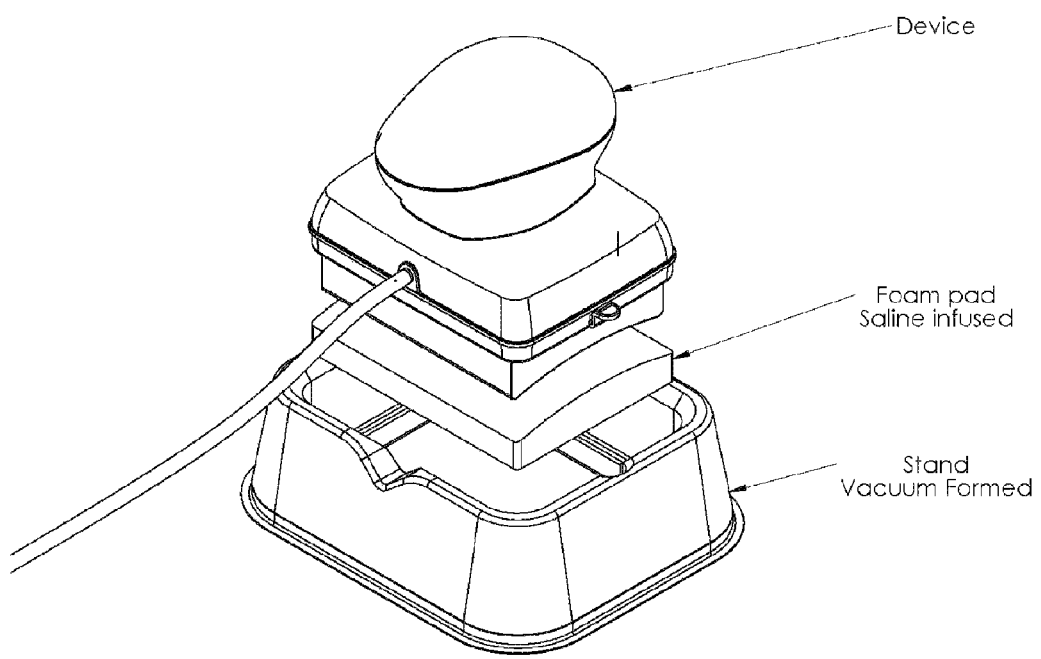
FIG. 73 the device with a sensor resting on a vacuum formed stand.
Figure 74:
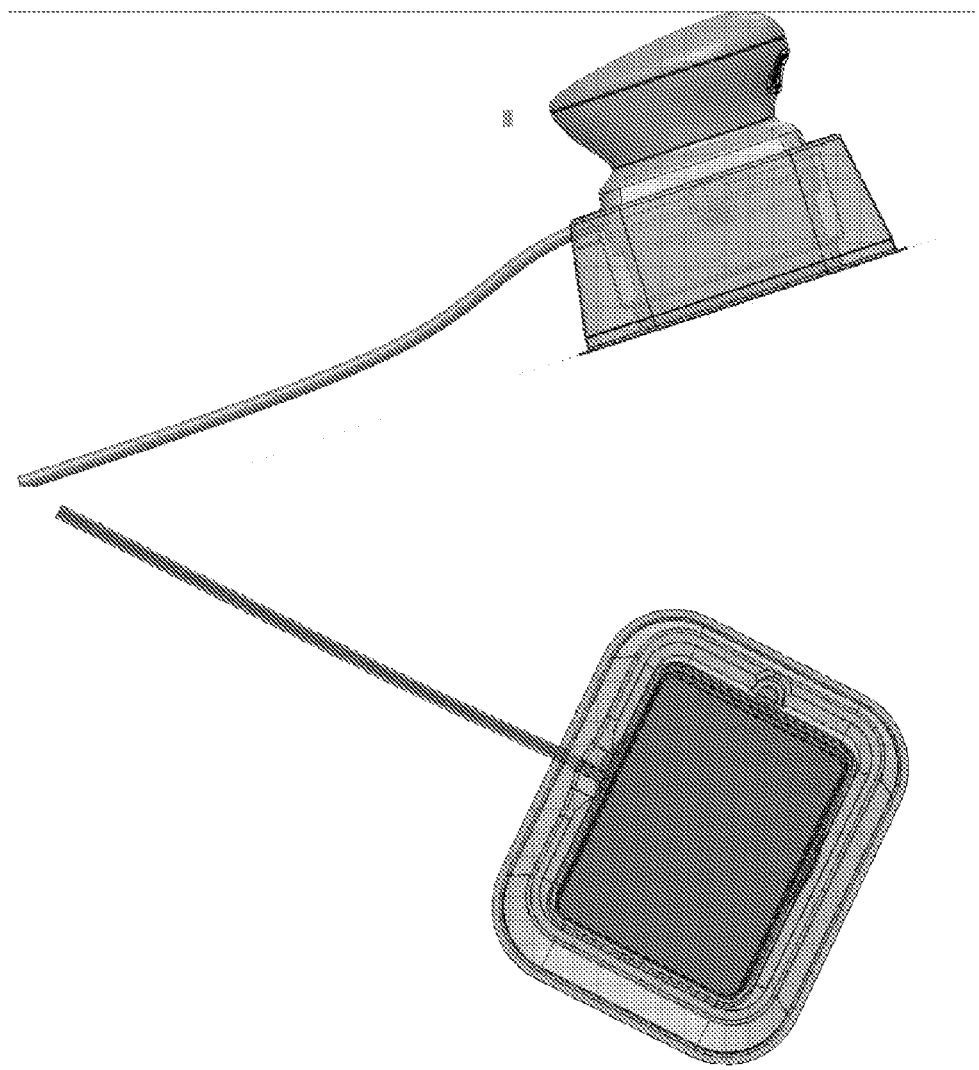
FIG. 74 shows two views of a device with a sensor and absorbent fluid reservoir resting on a stand.
Figure 75:
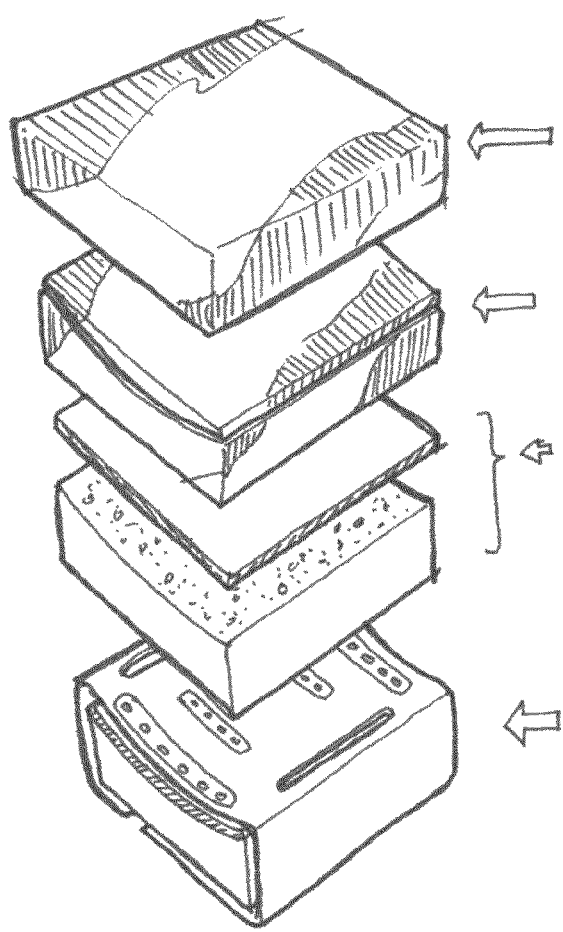
FIG. 75 shows an exploded view of—Foam—Pre wetted and skinned foam block.
Figure 76:
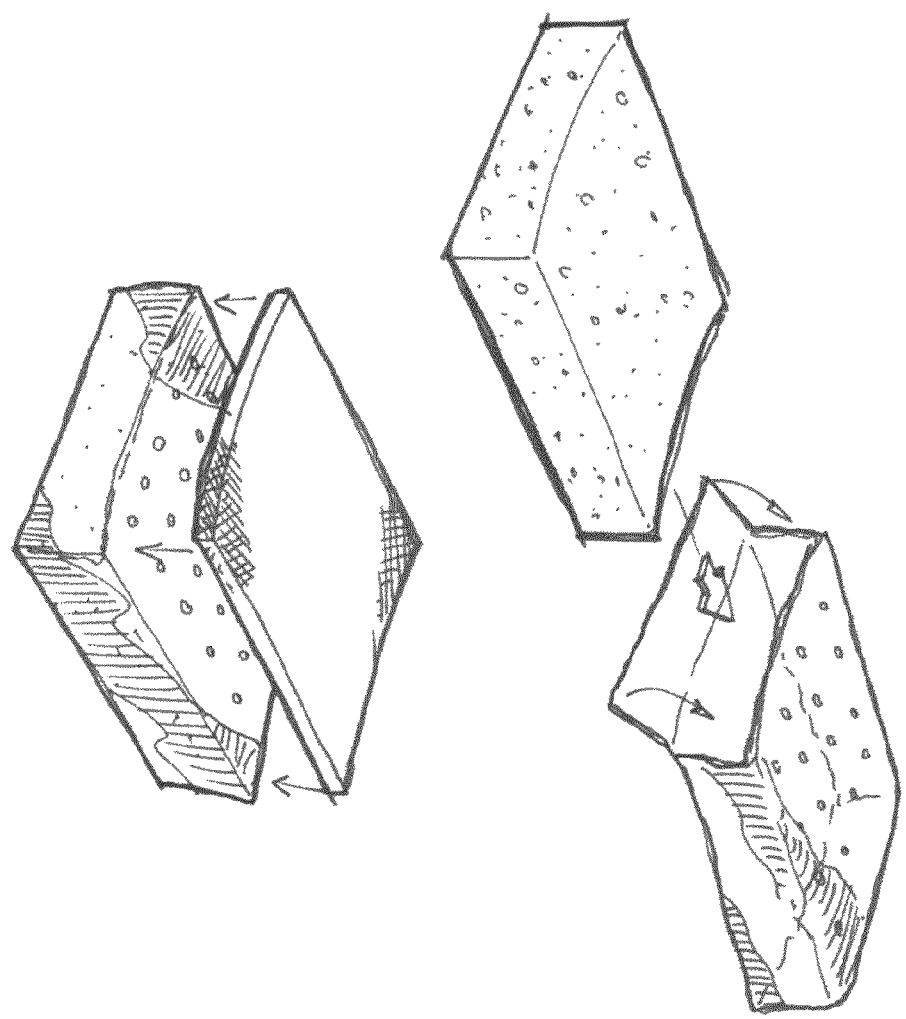
FIG. 76 shows foam prewetted and bagged.
Figure 77:
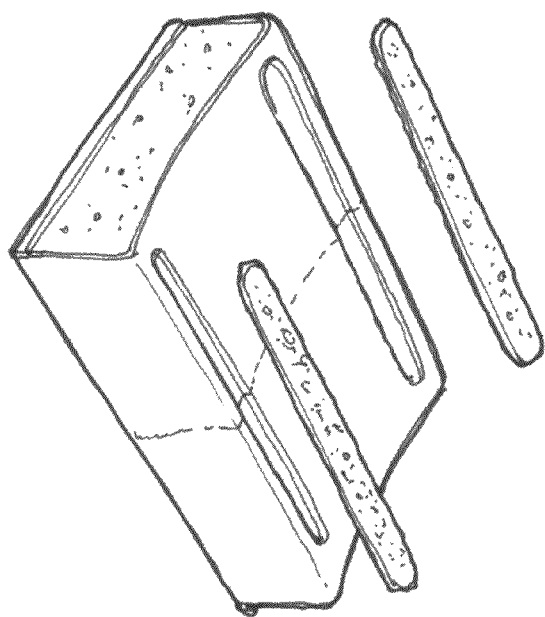
FIG. 77 shows surface strips/pads wipe.

The complete assembly (device plus disposable sensor) is connected to the electronics. The subject is wiped with saline solution on the desired place of contact. The disposable sensor is placed on the subject and measurements made. The disposable sensor is then removed from the subject. The composite assembly is shown in FIG. 70. The disposable sensor is on the bottom in the figure.

Example 20B with Fluid Pouch

Once the disposable sensor is removed from its packaging it is affixed to the handheld measurement device via means of either the built in plastic clip that is part of the disposable, or alternatively/additionally via a magnetic clasp (magnets in the handheld device work with steel elements embedded into the disposable sensor.) The disposable sensor is 'keyed' to ensure it can only be affixed to the handheld in one correct orientation.

With the disposable sensor affixed to the handheld device to form the composite assembly, the practitioner is now ready to begin the testing procedure. In order to activate the disposable sensor and release the included saline, the practitioner would be required to perform an action to open the included saline pouch. It is envisaged that there are a number of ways to achieve this as mentioned in the previous section.

(A) Puncture the pouch: The practitioner would 'arm' the disposable sensor by either removing a guard that shields the puncture needle(s), or would push an element on the disposable sensor or the device to expose the needles. Once 'armed' the user would then 'pump' the disposable sensor (mounted on the handheld) against the tissue that is to be tested. This pumping action is a compression that forces the disposable against the tissue, which in turn puts pressure on the foam and hence the saline reservoir pouch. Saline then flows from the pouch into the open cell 'sponge' foam and charges the disposable sensor. Small holes in the sensor surface allow saline to transfer from the foam through the holes onto the sensor surface and hence onto the patients skin. The action of pumping is then augmented with motion to spread the saline over the sensor and skin. Once sufficient saline is present on the skin, the sensor makes electrical contact and the system indicates the status of the signal via indicator lights on the device as well as in the software on the computer screen.

(B) Pull tab release: In the same manner as (A) the practitioner will arm the disposable sensor, however in this embodiment the arming will be done via the removal of a 'pull tab' (similar to those used on electronic devices to enable a battery to be connected). Removal of the pull tab exposes holes in the saline pouch membrane. The user then proceeds to 'pump' the device just like in option (A) to charge the foam reservoir.

Both option A & B are envisaged to have either a single saline pouch, or a segmented/multi pouch included. The goal of this inclusion is to provide a series of releases of saline to enable fine control over the amount of saline being released. When one reservoir has been exhausted, the next can be opened and so on.

Upon completion of the procedure, or use of that particular sensor (multiple sensors may be required) the disposable is simply removed and disposed of along with its packaging.

Example 20C with Absorbent Fluid Reservoir

The base plate of Example 11 and the Flex Circuit of Example 12 are assembled as in Example 16 to form the disposable sensor.

A foam substrate is used between the plastic base plate and the flex circuit sensor in order to facilitate a flexible and pliable assembly that when applied to the subject's anatomy can readily deform to provide a consistent contact between the sensor circuit and the subject's skin. This foam is injection molded from an open cell foam that will act as a sponge to create the fluid storage. Injection molding of the foam causes the outside surfaces to form a skin that is watertight.

Saline is not incorporated directly into the 'disposable' in this concept, instead a separate saline reservoir is supplied in the form of a device stand that includes a foam 'stamp pad' that is pre-wetted with saline.

The 'Stand' shown below is comprised of 2 parts, the stand itself is manufactured from a thermoformed plastic sheet in order to create a stable base for the registration and temporary storage of the complete assembly of the device and disposable. Contained within the stand there is the 'stamp pad reservoir', this is a simple die cut foam pad that is held into the stand via adhesive on the bottom of the foam. The adhesive could be double sided PSA or another adhesive that will allow the pad to bond to the stand.

Once the pad is installed into the stand, during assembly the pad is then pre-wetted with saline, the amount of saline is adjusted based on the desired life of the saline dispensing, factoring in the amount of saline transferred from the pad to the sensor, as well as evaporation.

The completed stand then is assembled with a sensor, and the entire assembly is bagged in a sealed pouch that does not permit any evaporation.

Example 21—Foam—the Composite Assembly

The electronic sensor portion of the disposable is applied to the base plate via means of registration features in both elements. The flex circuit is bonded to the base plate using pressure sensitive adhesive (PSA) that is a component of the laminate of the 'flex circuit sensor'. Assembly is done at the time of sensor manufacture, not by the practitioner. The flex circuit incorporates a 'petal' style of electrical connector that allows the sensor to form an electrical connection with the handheld device through a set of fixed pins in the handheld device. The 'petals' in the sensor allow for misalignment and tolerance stack-up between the device and the disposable to ensure a viable electrical connection.

A foam substrate is used between the plastic base plate and the flex circuit sensor in order to facilitate a flexible and pliable assembly that when applied to the patients anatomy can readily deform to provide a consistent contact between the sensor circuit and the patients skin.

Example 22—Foam—Prewetted and Skinned Foam Block

This foam is injection molded from an open cell foam that will act as a sponge to create the fluid storage. Injection molding of the foam causes the outside surfaces to form a skin that is watertight. The molded block is then hot wire or saw cut to create the curved surface that backs up the flex circuit sensor. When cut the open cell foam is exposed on that face.

A blotter layer is then laid onto the cut face of the foam. This blotter layer is intended to absorb the saline solution and create an intermediate layer between the foam block and the flex sensor, the purpose of which is to evenly distribute the saline and limit flow to the sensor from the foam reservoir. The layer is made from a suitable material such as cotton or similar synthetic alternative.

The Saline solution is infused into the foam block during assembly. Once assembly is complete the entire disposable sensor is packaged in a water and air tight package to ensure no evaporation of the solution during storage and shipping.

Saline travels from the foam, through the blotter layer and on to the flex sensor surface via a series of small holes punched into the flex sensor. The position of these holes is optimized to ensure saline is delivered to the appropriate areas to enable the best electrical properties to complete a test.

Optionally larger holes can be made in the sensor and foam transfer strips/pads can be included to store more saline at the sensor surface.

Example 23—Use Model for the Prewetted and Skinned Foam Block

This design would be supplied as a complete assembly in a sterile single use package, which would be assigned to the patient for one procedure and would be opened immediately prior to or during the setup for the procedure.

Once the disposable is removed from its packaging it would be affixed to the handheld measurement device via means of either the built in plastic clip that is part of the disposable, or alternatively/additionally via a magnetic clasp (magnets in the handheld device work with steel elements embedded into the disposable.) The disposable is 'keyed' to ensure it can only be affixed to the handheld in one correct orientation.

With the disposable affixed to the handheld the practitioner is now ready to begin the testing procedure. In order to activate the disposable device i.e. release the included saline, the practitioner is simply required to press the disposable against the patients tissue sufficiently to compress the foam block. The act of compressing this block forces saline out of the reservoir and into the blotter, and on to the sensor surface. At this time the practitioner would move the disposable sensor across the patients skin to spread the saline until a sufficiently good signal is achieved and indicated by the LED indicators in the handheld device.

Upon completion of the procedure, or use of that particular sensor (multiple sensors may be required) the disposable is simply removed and disposed of along with its packaging.

Example 24—Foam Pre Wetted and Bagged

Identical to Example 22, however instead of using a skinned foam, the foam block would be cut from a block of open cell foam, assembled to the blotter and then inserted into a preformed plastic bag (likely PET, PVC but any film polymer would work. The bag is then sealed around the foam via PSA adhesive already on the bag, or via ultrasonic/RF welding.

The sop surface of the bag that sits above the blotter would be pre punched with holes to allow saline to egress the bag and flood the sensor flex circuit.

Example 25—Foam—Pre Wetted and Vacuum Formed Container

Identical to Example 22, however instead of using a skinned foam, the foam block would be cut from a block of open cell foam, assembled to the blotter and then inserted into a vacuum formed carrier (without intending to be limiting, likely PET, PVC, PE, PP but any thermo formable film polymer would work). The carrier is then sealed around the foam via PSA adhesive already on the carrier, or via ultrasonic/RF welding or other method of joining.

The top surface of the bag that sits below the flex circuit would be pre punched with holes to allow saline to egress the bag and flood the sensor flex circuit.

Example 26—Use Model for the Absorbent Fluid Reservoir

This design would be supplied as a complete assembly in a sterile single use package, which would be assigned to the patient for one procedure and would be opened immediately prior to or during the setup for the procedure.

Once the disposable and flexible absorbent reservoir (stand/stamp pad) are removed from packaging, the stand is placed on a convenient work surface. The disposable sensor is affixed to the handheld measurement device via means of either the built in plastic clip that is part of the disposable, or alternatively/additionally via a magnetic clasp (magnets in the handheld device work with steel elements embedded into the disposable.) The sensor is 'keyed' to ensure it can only be affixed to the handheld in one correct orientation.

With the disposable sensor affixed to the handheld the practitioner is now ready to begin the testing procedure. In order to prepare the composite assembly for use, saline must be applied to the sensor by placing the device in the stand and pressing down. The action of pressing down causes saline to be transferred from the pad to the sensor.

It is envisaged that surface coatings may be employed on the sensor to promote adhesion of saline to the sensor pads, and not to the substrate. The appropriate hydrophilic and hydrophobic coatings can be used to affect the surface tension and wettability of the sensor.

Additionally electronic status indicators can be used in the composite assembly and/or in the system to signal the user when sufficient saline is present on the sensor while 'docked' in the stand.

Upon completion of the procedure, or use of that particular sensor (multiple sensors may be required) the disposable is simply removed and disposed of along with its packaging.

Example 27—Surface Strips/Pads Wipe

The base plate of Example 11 and the Flex Circuit of Example 12 are assembled as in Example 16.

A foam substrate is used between the plastic base plate and the flex circuit sensor in order to facilitate a flexible and pliable assembly that when applied to the patients anatomy can readily deform to provide a consistent contact between the sensor circuit and the patients skin. This foam is injection molded from an open cell foam that will act as a sponge to create the fluid storage. Injection molding of the foam causes the outside surfaces to form a skin that is watertight.

Saline is not incorporated directly into the 'disposable' foam block, instead a strip or pad or multiples of are included on the sensor surface. These pads contain saline much like a saline wipe. The action of rubbing the disposable on the patients skin transfers saline form the pads to the skin.

The completed stand then is assembled with a sensor, and the entire assembly is bagged in a sealed pouch that does not permit any evaporation.

Example 28—Use Model for the Surface Strips/Pads Wipe

This design would be supplied as a complete product in a sterile single use package, which would be assigned to the patient for one procedure and would be opened immediately prior to or during the setup for the procedure.

Once the disposable is removed from its packaging, the disposable sensor is affixed to the handheld measurement device via means of either the built in plastic clip that is part of the disposable, or alternatively/additionally via a magnetic clasp (magnets in the handheld device work with steel elements embedded into the disposable.) The disposable is 'keyed' to ensure it can only be affixed to the handheld in one correct orientation.

With the disposable affixed to the handheld the practitioner is now ready to begin the testing procedure. In order to prepare the disposable device for use, saline must be applied to the sensor by placing the device on the patients skin and moving it across the surface to transfer saline from the pads to the skin.

Upon completion of the procedure, or use of that particular sensor (multiple sensors may be required) the disposable is simply removed and disposed of along with its packaging.

We claim:

1. A method for measuring a localized biological transfer impedance (LBTI) of a tissue, using a device including a disposable sensor with a plurality of electrodes, the plurality of electrodes including at least a pair of current electrodes and a pair of voltage electrodes, with one or more of the plurality of electrodes comprising one or more sensor pads, the method comprising:
   positioning the plurality of electrodes of the device in contact with a portion of the tissue so that at least one sensor pad is in contact with the portion of tissue;
   passing a current through the tissue using the pair of current electrodes so that the current also passes through the at least one sensor pad which is in contact with the portion of tissue;
   measuring a signal across the pair of voltage electrodes, the signal corresponding to a voltage resulting from the current passed through the tissue;
   and analyzing the current passed through the tissue and the measured signal to determine the localized biological transfer impedance (LBTI) of the tissue.

2. The method of claim 1, in which at least one of the one or more sensor pads comprises a hydrophilic coating.

3. The method of claim 2, in which the hydrophilic coating on at least one of the sensor pads comprises one or more gel blocks.

4. The method of claim 2, in which the hydrophilic coating on at least one of the sensor pads is prewetted during the assembly process of the device.

5. The method of claim 2 in which the hydrophilic coating on at least one of the sensor pads is moistened immediately prior to use.

6. The method of claim 3 in which the gel block comprises an ionic gel.

7. The method of claim 3 in which the gel block comprises a non-ionic gel.

8. A device for measuring
   the localized biological transfer impedance (LBTI) of a tissue comprising:
   a disposable sensor with a plurality of electrodes, the plurality of electrodes including at least a pair of current electrodes and a pair of voltage electrodes, with one or more of the plurality of electrodes comprising one or more sensor pads,
   a power supply configured to be operably coupled to the plurality of electrodes to supply a signal through the tissue;
   analytical electronics configured to be operably coupled to the plurality of electrodes for analyzing a input current and resulting voltage to determine the electrical characteristics of the tissue; and
   electronics configured to communicate to a user a result of analysis performed by the analytical electronics.

9. The device of claim 8 in which at least one of the one or more sensor pads comprises a hydrophilic coating.

10. The device of claim 9 in which the hydrophilic coating on at least one of the sensor pads comprises one or more gel blocks.

11. The device of claim 9 in which the hydrophilic coating on at least one of the sensor pads is prewetted during the assembly process of the device.

12. The device of claim 9 in which the hydrophilic coating on at least one of the sensor pads is moistened immediately prior to use.

13. The device of claim 10 in which the gel block comprises an ionic gel.

14. The device of claim 10 in which the gel block comprises a non-ionic gel.

15. The method of claim 3 in which at least one gel block is prewetted during the assembly process of the device.

16. The method of claim 3 in which at least one gel block is moistened immediately prior to use.

17. The device of claim 10 in which at least one gel block is prewetted during the assembly process of the device.

18. The device of claim 10 in which at least one gel block is moistened immediately prior to use.

* * * * *